(12) United States Patent
Strong et al.

(10) Patent No.: US 11,397,173 B2
(45) Date of Patent: Jul. 26, 2022

(54) INTERCONNECTED CORRUGATED CARBON-BASED NETWORK

(71) Applicant: The Regents of the University of California, Oakland, CA (US)

(72) Inventors: Veronica Strong, Portland, OR (US); Maher F. El-Kady, Los Angeles, CA (US); Richard B. Kaner, Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/791,504

(22) Filed: Feb. 14, 2020

(65) Prior Publication Data
US 2020/0232960 A1    Jul. 23, 2020

Related U.S. Application Data

(60) Continuation of application No. 15/427,210, filed on Feb. 8, 2017, now Pat. No. 10,648,958, which is a
(Continued)

(51) Int. Cl.
*G01N 33/00* (2006.01)
*B32B 9/00* (2006.01)
(Continued)

(52) U.S. Cl.
CPC ........... *G01N 33/0037* (2013.01); *B32B 3/26* (2013.01); *B32B 3/28* (2013.01); *B32B 9/007* (2013.01);
(Continued)

(58) Field of Classification Search
CPC .. B32B 3/26; B32B 3/28; B32B 9/007; B32B 9/041; B32B 9/045; B32B 18/00;
(Continued)

(56) References Cited

U.S. PATENT DOCUMENTS

| 2,800,616 A | 7/1957 | Becker |
| 3,223,639 A | 12/1965 | Powers et al. |

(Continued)

FOREIGN PATENT DOCUMENTS

| CN | 1092208 A | 9/1994 |
| CN | 1253390 A | 5/2000 |

(Continued)

OTHER PUBLICATIONS

Zhang et al., Direct Imprinting of Microcircuits on Graphene Oxides Film by Femtosecond Laser Reduction, Nano Today, 2010 (5), p. 15-20.*
(Continued)

*Primary Examiner* — Brittany L Raymond
(74) *Attorney, Agent, or Firm* — Withrow & Terranova, P.L.L.C.

(57) ABSTRACT

An interconnected corrugated carbon-based network comprising a plurality of expanded and interconnected carbon layers is disclosed. In one embodiment, each of the expanded and interconnected carbon layers is made up of at least one corrugated carbon sheet that is one atom thick. In another embodiment, each of the expanded and interconnected carbon layers is made up of a plurality of corrugated carbon sheets that are each one atom thick. The interconnected corrugated carbon-based network is characterized by a high surface area with highly tunable electrical conductivity and electrochemical properties.

18 Claims, 23 Drawing Sheets

Related U.S. Application Data division of application No. 13/725,073, filed on Dec. 21, 2012, now abandoned.

(60) Provisional application No. 61/578,431, filed on Dec. 21, 2011.

(51) Int. Cl.

| | | |
|---|---|---|
| *B32B 9/04* | (2006.01) | |
| *B32B 27/32* | (2006.01) | |
| *B32B 3/28* | (2006.01) | |
| *H01B 1/04* | (2006.01) | |
| *C01B 32/23* | (2017.01) | |
| *B32B 3/26* | (2006.01) | |
| *B32B 18/00* | (2006.01) | |
| *G21K 5/02* | (2006.01) | |

(52) U.S. Cl.
CPC .............. *B32B 9/041* (2013.01); *B32B 9/045* (2013.01); *B32B 18/00* (2013.01); *B32B 27/32* (2013.01); *C01B 32/23* (2017.08); *G21K 5/02* (2013.01); *H01B 1/04* (2013.01); *B32B 2307/202* (2013.01); *B32B 2307/732* (2013.01); *B32B 2307/75* (2013.01); *B32B 2429/02* (2013.01); *B32B 2457/00* (2013.01); *B32B 2457/08* (2013.01); *B32B 2457/10* (2013.01); *B32B 2457/12* (2013.01); *B32B 2457/20* (2013.01); *C04B 2237/086* (2013.01); *C04B 2237/363* (2013.01); *C04B 2237/592* (2013.01); *C04B 2237/72* (2013.01); *Y02A 50/20* (2018.01)

(58) Field of Classification Search
CPC .............. B32B 27/32; B32B 2307/202; B32B 2307/732; B32B 2307/75; B32B 2429/02; B32B 2457/00; B32B 2457/08; B32B 2457/10; B32B 2457/12; B32B 2457/20; C01B 32/23; G01N 33/0037; G21K 5/02; H01B 1/04; Y02A 50/20
See application file for complete search history.

(56) References Cited

U.S. PATENT DOCUMENTS

| | | |
|---|---|---|
| 3,288,641 A | 11/1966 | Rightmire |
| 3,536,963 A | 10/1970 | Boos |
| 3,652,902 A | 3/1972 | Hart et al. |
| 3,749,608 A | 7/1973 | Sarbacher |
| 4,327,157 A | 4/1982 | Himy et al. |
| 4,645,713 A | 2/1987 | Shioya et al. |
| 5,143,709 A | 9/1992 | Labes |
| 5,225,296 A | 7/1993 | Ohsawa et al. |
| 5,442,197 A | 8/1995 | Andrieu et al. |
| 5,744,258 A | 4/1998 | Bai et al. |
| 6,043,630 A | 3/2000 | Koenck et al. |
| 6,117,585 A | 9/2000 | Anani et al. |
| 6,252,762 B1 | 6/2001 | Amatucci |
| 6,356,433 B1 | 3/2002 | Shi et al. |
| 6,451,074 B2 | 9/2002 | Bluvstein et al. |
| 6,510,043 B1 | 1/2003 | Shiue et al. |
| 6,522,522 B2 | 2/2003 | Yu et al. |
| 6,982,517 B2 | 1/2006 | Reineke et al. |
| 7,623,340 B1 | 11/2009 | Song et al. |
| 7,833,663 B2 | 11/2010 | Phillips et al. |
| 7,875,219 B2 | 1/2011 | Zhamu et al. |
| 8,315,039 B2 | 11/2012 | Zhamu et al. |
| 8,503,161 B1 | 8/2013 | Chang et al. |
| 8,593,714 B2 | 11/2013 | Agrawal et al. |
| 8,753,772 B2 | 6/2014 | Liu et al. |
| 8,771,630 B2 | 7/2014 | Wu et al. |
| 8,828,608 B2 | 9/2014 | Sun et al. |
| 8,906,495 B2 | 12/2014 | Chen |
| 8,951,675 B2 | 2/2015 | Bhardwaj et al. |
| 9,118,078 B2 | 8/2015 | Huang et al. |
| 9,295,537 B2 | 3/2016 | Cao |
| 9,437,372 B1 | 9/2016 | Zhamu et al. |
| 2002/0136881 A1 | 9/2002 | Yanagisawa et al. |
| 2002/0160257 A1 | 10/2002 | Lee et al. |
| 2003/0013012 A1 | 1/2003 | Ahn et al. |
| 2003/0169560 A1 | 9/2003 | Welsch et al. |
| 2004/0090736 A1 | 5/2004 | Bendale et al. |
| 2004/0099641 A1 | 5/2004 | Mathieu et al. |
| 2004/0131889 A1 | 7/2004 | Leddy et al. |
| 2005/0153130 A1 | 7/2005 | Long et al. |
| 2006/0121342 A1 | 6/2006 | Sano et al. |
| 2006/0201801 A1 | 9/2006 | Bartlett et al. |
| 2006/0207878 A1 | 9/2006 | Myung et al. |
| 2006/0269834 A1 | 11/2006 | West et al. |
| 2007/0172739 A1 | 7/2007 | Visco et al. |
| 2007/0204447 A1 | 9/2007 | Bernstein et al. |
| 2008/0090141 A1 | 4/2008 | Meitav et al. |
| 2008/0158778 A1 | 7/2008 | Lipka et al. |
| 2008/0180883 A1 | 7/2008 | Palusinski et al. |
| 2008/0199737 A1 | 8/2008 | Kazaryan et al. |
| 2008/0220293 A1 | 9/2008 | Marmaropoulos et al. |
| 2008/0265219 A1 | 10/2008 | Whitehead et al. |
| 2008/0316678 A1 | 12/2008 | Ehrenberg et al. |
| 2009/0059474 A1 | 3/2009 | Zhamu et al. |
| 2009/0061312 A1 | 3/2009 | Zhamu et al. |
| 2009/0117467 A1 | 5/2009 | Zhamu et al. |
| 2009/0289328 A1 | 11/2009 | Tanioku |
| 2009/0290287 A1 | 11/2009 | Lipka et al. |
| 2010/0003598 A1 | 1/2010 | Nakamura |
| 2010/0159346 A1 | 6/2010 | Hinago et al. |
| 2010/0159366 A1 | 6/2010 | Shao-Horn et al. |
| 2010/0195269 A1 | 8/2010 | Kim et al. |
| 2010/0203362 A1 | 8/2010 | Lam et al. |
| 2010/0221508 A1* | 9/2010 | Huang .................. G03F 7/0042 428/195.1 |
| 2010/0226066 A1 | 9/2010 | Sweeney et al. |
| 2010/0237296 A1 | 9/2010 | Gilje |
| 2010/0266964 A1* | 10/2010 | Gilje .................. C01B 32/192 430/322 |
| 2010/0273051 A1 | 10/2010 | Choi et al. |
| 2010/0317790 A1 | 12/2010 | Jang et al. |
| 2011/0026189 A1 | 2/2011 | Wei et al. |
| 2011/0075323 A1 | 3/2011 | Kawakami et al. |
| 2011/0079748 A1 | 4/2011 | Ruoff et al. |
| 2011/0111283 A1 | 5/2011 | Rust, III et al. |
| 2011/0111299 A1* | 5/2011 | Liu .................. B82Y 30/00 429/221 |
| 2011/0143101 A1* | 6/2011 | Sandhu .................. B82Y 30/00 428/195.1 |
| 2011/0159372 A1 | 6/2011 | Zhamu et al. |
| 2011/0163274 A1 | 7/2011 | Plee et al. |
| 2011/0163699 A1 | 7/2011 | Elder et al. |
| 2011/0183180 A1 | 7/2011 | Yu et al. |
| 2011/0227000 A1 | 9/2011 | Ruoff et al. |
| 2011/0242730 A1 | 10/2011 | Zhou et al. |
| 2011/0256454 A1 | 10/2011 | Nicolas et al. |
| 2011/0280787 A1 | 11/2011 | Chen et al. |
| 2011/0318257 A1* | 12/2011 | Sokolov .................. C01B 32/192 423/448 |
| 2012/0111730 A1 | 5/2012 | Choi et al. |
| 2012/0129736 A1 | 5/2012 | Tour et al. |
| 2012/0134072 A1 | 5/2012 | Bae et al. |
| 2012/0145234 A1* | 6/2012 | Roy-Mayhew ...... H01G 9/2022 136/256 |
| 2012/0187906 A1 | 7/2012 | Martienssen et al. |
| 2012/0300364 A1 | 11/2012 | Cai et al. |
| 2012/0313591 A1 | 12/2012 | Brambilla et al. |
| 2013/0026409 A1 | 1/2013 | Baker et al. |
| 2013/0048949 A1* | 2/2013 | Xia .................. H01L 51/0537 257/29 |
| 2013/0056346 A1 | 3/2013 | Sundara et al. |
| 2013/0056703 A1 | 3/2013 | Elian et al. |
| 2013/0100581 A1 | 4/2013 | Jung et al. |
| 2013/0148265 A1 | 6/2013 | Okuno et al. |
| 2013/0155578 A1 | 6/2013 | Tsai et al. |
| 2013/0161570 A1 | 6/2013 | Hwang et al. |
| 2013/0168611 A1 | 7/2013 | Zhou et al. |

(56) References Cited

U.S. PATENT DOCUMENTS

| | | |
|---|---|---|
| 2013/0171502 A1 | 7/2013 | Chen et al. |
| 2013/0180912 A1 | 7/2013 | Li |
| 2013/0182373 A1 | 7/2013 | Yu et al. |
| 2013/0189602 A1 | 7/2013 | Lahiri et al. |
| 2013/0217289 A1 | 8/2013 | Nayfeh et al. |
| 2013/0230747 A1 | 9/2013 | Patolsky et al. |
| 2013/0264041 A1 | 10/2013 | Zhamu et al. |
| 2013/0266858 A1 | 10/2013 | Inoue et al. |
| 2013/0280601 A1 | 10/2013 | Geramita et al. |
| 2013/0314844 A1 | 11/2013 | Chen et al. |
| 2013/0323159 A1 | 12/2013 | Lee et al. |
| 2013/0330617 A1 | 12/2013 | Yoshimura et al. |
| 2014/0029161 A1 | 1/2014 | Beidaghi et al. |
| 2014/0030590 A1 | 1/2014 | Wang et al. |
| 2014/0045058 A1 | 2/2014 | Zhao et al. |
| 2014/0050947 A1 | 2/2014 | Donnelly |
| 2014/0065447 A1 | 3/2014 | Liu et al. |
| 2014/0099558 A1 | 4/2014 | Itakura et al. |
| 2014/0118883 A1 | 5/2014 | Xie |
| 2014/0120453 A1 | 5/2014 | Ajayan et al. |
| 2014/0134503 A1 | 5/2014 | Lockett et al. |
| 2014/0146439 A1 | 5/2014 | Choi et al. |
| 2014/0154164 A1 | 6/2014 | Chen et al. |
| 2014/0170476 A1 | 6/2014 | Tan et al. |
| 2014/0178763 A1 | 6/2014 | Mettan |
| 2014/0205841 A1 | 7/2014 | Qiu et al. |
| 2014/0255776 A1 | 9/2014 | Song et al. |
| 2014/0255785 A1 | 9/2014 | Do et al. |
| 2014/0287308 A1 | 9/2014 | Okada et al. |
| 2014/0306858 A1 | 10/2014 | Tsai et al. |
| 2014/0313636 A1 | 10/2014 | Tour et al. |
| 2014/0323596 A1 | 10/2014 | Jeong et al. |
| 2015/0044560 A1 | 2/2015 | Ogino |
| 2015/0050554 A1 | 2/2015 | Fukumine et al. |
| 2015/0098167 A1 | 4/2015 | El-Kady et al. |
| 2015/0103469 A1 | 4/2015 | Lee et al. |
| 2015/0111449 A1 | 4/2015 | Cruz-Silva et al. |
| 2015/0218002 A1 | 8/2015 | Plomb et al. |
| 2015/0218003 A1 | 8/2015 | Zhamu et al. |
| 2015/0235776 A1 | 8/2015 | Miller |
| 2015/0259212 A1 | 9/2015 | Li et al. |
| 2015/0287544 A1 | 10/2015 | Irazoqui et al. |
| 2015/0298977 A1 | 10/2015 | Yoon |
| 2015/0311504 A1 | 10/2015 | Hong et al. |
| 2015/0332868 A1 | 11/2015 | Jung et al. |
| 2015/0340171 A1 | 11/2015 | Li et al. |
| 2015/0364738 A1 | 12/2015 | Pope et al. |
| 2015/0364755 A1 | 12/2015 | Liu et al. |
| 2016/0035498 A1 | 2/2016 | Honma et al. |
| 2016/0055983 A1 | 2/2016 | Kurungot et al. |
| 2016/0077074 A1 | 3/2016 | Strong et al. |
| 2016/0099116 A1 | 4/2016 | Yang |
| 2016/0133396 A1 | 5/2016 | Hsieh |
| 2016/0148759 A1 | 5/2016 | El-Kady et al. |
| 2017/0062821 A1 | 3/2017 | Tour et al. |
| 2017/0149107 A1 | 5/2017 | El-Kady et al. |
| 2017/0178824 A1 | 6/2017 | Kaner et al. |
| 2017/0213657 A1 | 7/2017 | Kaner et al. |
| 2017/0240424 A1 | 8/2017 | Roberts et al. |
| 2017/0271093 A1 | 9/2017 | El-Kady et al. |
| 2017/0278643 A1 | 9/2017 | El-Kady et al. |
| 2017/0287650 A1 | 10/2017 | Kaner et al. |
| 2017/0299563 A1 | 10/2017 | Strong et al. |
| 2017/0338472 A1 | 11/2017 | Zhamu et al. |
| 2017/0369323 A1 | 12/2017 | Kowal et al. |
| 2018/0062159 A1 | 3/2018 | El-Kady et al. |
| 2018/0323016 A1 | 11/2018 | El-Kady et al. |
| 2018/0366280 A1 | 12/2018 | Hwang et al. |
| 2019/0006675 A1 | 1/2019 | Cheng et al. |
| 2019/0019630 A1 | 1/2019 | Strauss et al. |
| 2019/0088420 A1 | 3/2019 | Tour et al. |
| 2019/0123409 A1 | 4/2019 | El-Kady et al. |
| 2019/0237752 A1 | 8/2019 | El-Kady et al. |
| 2019/0284403 A1 | 9/2019 | Kaner et al. |
| 2020/0090880 A1 | 3/2020 | Kaner et al. |

FOREIGN PATENT DOCUMENTS

| | | |
|---|---|---|
| CN | 100372035 C | 2/2008 |
| CN | 101723310 A | 6/2010 |
| CN | 101894679 A | 11/2010 |
| CN | 102187413 A | 9/2011 |
| CN | 102275896 A | 12/2011 |
| CN | 102491318 A | 6/2012 |
| CN | 102509632 A | 6/2012 |
| CN | 102543483 A | 7/2012 |
| CN | 102923698 A | 2/2013 |
| CN | 103208373 A | 7/2013 |
| CN | 103508450 A | 1/2014 |
| CN | 103715393 A | 4/2014 |
| CN | 103723715 A | 4/2014 |
| CN | 203631326 U | 6/2014 |
| CN | 203839212 U | 9/2014 |
| CN | 104229777 A | 12/2014 |
| CN | 104299794 A | 1/2015 |
| CN | 104355306 A | 2/2015 |
| CN | 104617300 A | 5/2015 |
| CN | 104637694 A | 5/2015 |
| CN | 104892935 A | 9/2015 |
| CN | 105062074 A | 11/2015 |
| CN | 105217621 A | 1/2016 |
| CN | 105585003 A | 5/2016 |
| EP | 1137081 A1 | 9/2001 |
| EP | 1262579 A2 | 12/2002 |
| EP | 1843362 A1 | 10/2007 |
| EP | 2088637 A2 | 8/2009 |
| EP | 2933229 A1 | 10/2015 |
| EP | 2958122 A1 | 12/2015 |
| EP | 2980891 A1 | 2/2016 |
| JP | S61010855 A | 1/1986 |
| JP | S62287568 A | 12/1987 |
| JP | 2002063894 A | 2/2002 |
| JP | 2003217575 A | 7/2003 |
| JP | 2004039491 A | 2/2004 |
| JP | 2004055541 A | 2/2004 |
| JP | 2004046297 A | 2/2004 |
| JP | 2004519841 A | 7/2004 |
| JP | 2005138204 A | 6/2005 |
| JP | 2005199267 A | 7/2005 |
| JP | 2005317902 A | 10/2005 |
| JP | 2006252902 A | 11/2005 |
| JP | 2007160151 A | 6/2007 |
| JP | 2008300467 A | 12/2008 |
| JP | 2009525247 A | 7/2009 |
| JP | 2010222245 A | 10/2010 |
| JP | 2011026153 A | 2/2011 |
| JP | 2011165680 A | 8/2011 |
| JP | 2012169576 A | 9/2012 |
| JP | 2012188484 A | 10/2012 |
| JP | 2013534686 A | 9/2013 |
| JP | 2014053209 A | 3/2014 |
| JP | 2014201492 A | 10/2014 |
| JP | 2015218085 A | 12/2015 |
| KR | 1020040079226 A | 9/2004 |
| KR | 20070083691 A | 8/2007 |
| KR | 20080064967 A | 7/2008 |
| KR | 10-2009-0107498 A | 10/2009 |
| KR | 20140012464 A | 2/2014 |
| KR | 1020100114827 A | 4/2017 |
| WO | 9632618 A1 | 10/1996 |
| WO | 2011019431 A1 | 2/2011 |
| WO | 2011021982 A1 | 2/2011 |
| WO | 2011072213 A2 | 6/2011 |
| WO | WO 2011-072213 * | 6/2011 |
| WO | 2012006657 A1 | 1/2012 |
| WO | 2012087698 A1 | 6/2012 |
| WO | 2012138302 A1 | 10/2012 |
| WO | 2013024727 A1 | 2/2013 |
| WO | 2013040636 A1 | 3/2013 |
| WO | 2013066474 A2 | 5/2013 |
| WO | 2013070989 A1 | 5/2013 |
| WO | 2013128082 A1 | 9/2013 |
| WO | 2013155276 A1 | 10/2013 |
| WO | 2014011722 A2 | 1/2014 |
| WO | 2014028978 A1 | 2/2014 |

(56) References Cited

FOREIGN PATENT DOCUMENTS

| | | | |
|---|---|---|---|
| WO | 2014062133 | A1 | 4/2014 |
| WO | 2014072877 | A2 | 5/2014 |
| WO | 2014134663 | A1 | 9/2014 |
| WO | 2014138721 | A1 | 9/2014 |
| WO | 2014181763 | A1 | 11/2014 |
| WO | 2015023974 | A1 | 2/2015 |
| WO | 2015069332 | A | 5/2015 |
| WO | 2015153895 | A1 | 10/2015 |
| WO | 2015195700 | A1 | 12/2015 |
| WO | 2016053956 | A1 | 4/2016 |
| WO | 2016094551 | A1 | 6/2016 |
| WO | 2016133571 | A2 | 8/2016 |
| WO | 2016190225 | A1 | 12/2016 |
| WO | 2017035462 | A1 | 3/2017 |

OTHER PUBLICATIONS

Author Unknown, "Sulfuric Acid—Density," The Engineering ToolBox, www.engineeringtoolbox.com/indsulfuric-acid-density-d_2163.html, accessed Oct. 2, 2020, 3 pages.
Reexamination Decision for Chinese Patent Application No. 201280070343.4, dated Aug. 31, 2020, 19 pages.
Notice of Allowability for U.S. Appl. No. 16/223,869, dated Sep. 15, 2020, 5 pages.
Non-Final Office Action for U.S. Appl. No. 16/428,409, dated Oct. 1, 2020, 14 pages.
Notice of Allowance for U.S. Appl. No. 16/692,123, dated Oct. 21, 2020, 8 pages.
Examination Report for Taiwanese Patent Application No. 106111115, dated Aug. 25, 2020, 17 pages.
Non-Final Office Action for U.S. Appl. No. 15/630,758, dated Oct. 1, 2020, 14 pages.
Notice of Allowance and Examiner-Initiated Interview Summary for U.S. Appl. No. 16/784,578, dated Oct. 15, 2020, 9 pages.
Notice of Allowance for U.S. Appl. No. 16/223,869, dated Jul. 9, 2020, 9 pages.
Official Action for Eurasian Patent Application No. 201791078, dated Jun. 23, 2020, 4 pages.
Examination Report for Indian Patent Application No. 201717016755, dated Jul. 2, 2020, 6 pages.
Examination Report for Indian Patent Application No. 201817020826, dated Jul. 13, 2020, 7 pages.
Notice of Allowance for U.S. Appl. No. 16/692,123, dated Jul. 15, 2020, 9 pages.
First Office Action and Search Report for Chinese Patent Application No. 2017800273161, dated Jun. 5, 2020, 15 pages.
Extended European Search Report for European Patent Application No. 17847303.9, dated Jul. 13, 2020, 9 pages.
Official Notification for Eurasian Patent Application No. 201990068, dated Jun. 23, 2020, 5 pages.
Advisory Action for U.S. Appl. No. 15/466,425, dated Jul. 7, 2020, 3 pages.
Non-Final Office Action for U.S. Appl. No. 15/466,425, dated Jul. 28, 2020, 8 pages.
Luo, Zhi-Jia et al., "A timesaving, low-cost, high-yield method for the synthesis of ultrasmall uniform graphene oxide nanosheets and their application in surfactants," Nanotechnology, vol. 27, Issue 5, Dec. 16, 2015, IOP Publishing Ltd, pp. 1-8.
Maiti, Sandipan et al., "Interconnected Network of $MnO_2$ Nanowires with a "Cocoonlike" Morphology: Redox Couple-Mediated Performance Enhancement in Symmetric Aqueous Supercapacitor," ACS Applied Materials & Interfaces, vol. 6, Issue 13, Jun. 16, 2014, American Chemical Society, pp. 10754-10762.
Maiti, Uday Narayan et al., "Three-Dimensional Shape Engineered, Interfacial Gelation of Reduced Graphene Oxide for High Rate, Large Capacity Supercapacitors," vol. 26, Issue 4, Jan. 29, 2014, WILEY-VCH Verlag GmbH & Co., pp. 615-619.
Mao, Lu et al., "Surfactant-stabilized graphene/polyaniline nanofiber composites for high performance supercapacitor electrode," Journal of Materials Chemistry, vol. 22, Issue 1, Oct. 12, 2011, The Royal Society of Chemistry, pp. 80-85.
Marcano, Daniela C. et al., "Improved Synthesis of Graphene Oxide," ACS Nano, vol. 4, Issue 8, Jul. 22, 2010, American Chemical Society, pp. 4806-4814.
Miller, John R. et al., "Electrochemical Capacitors for Energy Management," Materials Science, vol. 321, Aug. 1, 2008, AAAS, pp. 651-652.
Moosavifard, Seyyed E. et al., "Designing 3D highly ordered nanoporous CuO electrodes for high-performance asymmetric supercapacitors," ACS Applied Materials & Interfaces, vol. 7, Issue 8, American Chemical Society, 13 pages.
Moussa, Mahmoud et al., "Free-Standing Composite Hydrogel Film for Superior Volumetric Capacitance," Journal of Materials Chemistry A, vol. 3, Issue 30, Jun. 19, 2015, The Royal Society of Chemistry, pp. 1-8.
Naoi, Katsuhiko et al., "Second generation 'nanohybrid supercapacitor': Evolution of capacitive energy storage devices," Energy & Environmental Science, vol. 5, Issue 11, Sep. 14, 2012, The Royal Society of Chemistry, pp. 9363-9373.
Nathan, Arokia et al., "Flexible Electronics: The Next Ubiquitous Platform," Proceedings of the IEEE, vol. 100, Special Centennial Issue, May 13, 2012, IEEE, pp. 1486-1517.
Niu, Zhiqiang et al., "A Leavening Strategy to Prepare Reduced Graphene Oxide Foams," Advanced Materials, vol. 24, Issue 30, Aug. 8, 2012, WILEY-VCH Verlag GmbH & Co., pp. 1-7.
Oudenhoven, Jos F. M. et al., "All-Solid-State Lithium-Ion Microbatteries: A Review of Various Three-Dimensional Concepts," Advanced Energy Matterials, vol. 1, Issue 1, WILEY-VCH Verlag GmbH & Co. KGaA, Weinheim, pp. 10-33.
Paravannoor, Anjali et al., "High voltage supercapacitors based on carbon-grafted NiO nanowires interfaced with an aprotic ionic liquid," Chemical Communications, vol. 51, Issue 28, Feb. 26, 2015, The Royal Society of Chemistry, pp. 1-4.
Patel, Mehul N. et al., "Hybrid $MnO_2$-disordered mesoporous carbon nanocomposites: synthesis and characterization as electrochemical pseudocapacitor electrodes," Journal of Materials Chemistry, vol. 20, Issue 2, Nov. 11, 2009, The Royal Society of Chemistry, pp. 390-398.
Pech, David et al, "Ultrahigh-power micrometre-sized supercapacitors based on onion-like carbon," Nature Nanotechnology, vol. 5, Sep. 2010, Macmillan Publishers Limited, 10 pages.
Pendashteh, Afshin et al., "Fabrication of anchored copper oxide nanoparticles on graphene oxide nanosheets via an electrostatic coprecipitation and its application as supercapacitor," Electrochimica Acta, vol. 88, Oct. 29, 2012, Elsevier Ltd., pp. 347-357.
Pendashteh, Afshin et al., "Facile synthesis of nanostructured $CuCo_2O_4$ as a novel electrode material for high-rate supercapacitors," vol. 50, Issue 16, Dec. 17, 2013, The Royal Society of Chemistry, 4 pages.
Pendashteh, Afshin et al., "Highly Ordered Mesoporous $CuCo_2O_4$ Nanowires, a Promising Solution for High-Performance Supercapacitors," Chemistry of Materials, vol. 27, Issue 11, Apr. 20, 2015, American Chemical Society, pp. 1-11.
Qing, Xutang et al., "P/N/O co-doped carbonaceous materials based supercapacitor with voltage up to 1.9 V in the aqueous electrolyte," RSC Advances, vol. 4, Issue 99, Oct. 21, 2014, Royal Society of Chemistry, pp. 1-22.
Qiu, Ling et al., "Controllable Corrugation of Chemically Converted Graphene Sheets in Water and Potential Application for Nanofiltration," Chemical Communications, vol. 47, 2011, pp. 5810-5812.
Qu, Qunting et al., "Core-Shell Structure of Polypyrrole Grown on $V_2O_5$ Nanoribbon as High Performance Anode Material for Supercapacitors," Advanced Energy Materials, vol. 2, Issue 8, 2012, WILEY-VCH Verlag GmbH & Co., pp. 1-6.
Raccichini, Rinaldo et al., "The role of graphene for electrochemical energy storage," Nature Materials, vol. 14, Issue 3, Dec. 22, 2014, Macmillan Publishers Limited, pp. 1-9.
Samitsu, Sadaki et al., "Flash freezing route to mesoporous polymer nanofibre networks," Nature Communications, vol. 4, Issue 2653, Oct. 22, 2013, Macmillan Publishers Limited, pp. 1-7.

(56) References Cited

OTHER PUBLICATIONS

Shao, Yuanlong et al., "Fabrication of large-area and high-crystallinity photoreduced graphene oxide films via reconstructed two-dimensional multilayer structures," NPG Asia Materials, vol. 6, Issue 8, e119, Aug. 15, 2014, Nature Publishing Group, pp. 1-9.
Shao, Yuanlong et al., "Graphene-based materials for flexible supercapacitors," Chemical Society Review, vol. 44, Issue 11, Apr. 22, 2015, The Royal Society of Chemistry, 27 pages.
Shao, Yuanlong et al., "High-performance flexible asymmetric supercapacitors based on 3D porous graphene/$MnO_2$ nanorod and graphene/Ag hybrid thin-film electrodes," Journal of Materials Chemistry C, vol. 1, Dec. 5, 2012, The Royal Society of Chemistry, pp. 1245-1251.
Sheats, James R., "Manufacturing and commercialization issues in organic electronics," Journal of Materials Research, vol. 19, Issue 7, Jul. 2004, Materials Research Society, pp. 1974-1989.
Shen, Caiwei et al., "A high-energy-density micro supercapacitor of asymmetric $MnO_2$-carbon configuration by using micro-fabrication technologies," Journal of Power Sources, vol. 234, Feb. 9, 2013, Elsevier B.V., pp. 302-309.
Shen, Jiali et al., "High-Performance Asymmetric Supercapacitor Based on Nano-architectured Polyaniline/Graphene/Carbon Nanotube and Activated Graphene Electrodes," ACS Applied Materials & Interfaces, vol. 5, Issue 17, Aug. 9, 2013, American Chemical Society, 36 pages.
Shown, Indrajit et al., "Conducting polymer-based flexible supercapacitor," Energy Science & Engineering, vol. 3, Issue 1, Nov. 19, 2014, Society of Chemical Industry and John Wiley & Sons Ltd , pp. 1-25.
Simon, P. et al., "Capacitive Energy Storage in Nanostructured Carbon-Electrolyte Systems," Accounts of Chemical Research, vol. 46, Issue 5, Jun. 6, 2012, American Chemical Society, 10 pages.
Simon, Patrice et al., "Materials for electrochemical capacitors," Nature Materials, vol. 7, Issue 11, Nov. 2008, Macmillan Publishers Limited, pp. 845-854.
Simon, Patrice et al., "Where Do Batteries End and Supercapacitors Begin?" Science, vol. 343, Issue 6176, Mar. 14, 2014, American Association for the Advancement of Science, 3 pages.
Snook, Graeme A. et al., "Conducting-polymer-based supercapacitor devices and electrodes," Journal of Power Sources, vol. 196, Jul. 15, 2010, Elsevier B V., pp. 1-12.
Stoller, Meryl D. et al., "Graphene-Based Ultracapacitors," Nano Letters, vol. 8, Issue 10, Sep. 13, 2008, American Chemical Society, pp. 3498-3502.
Strong, Veronica et al., "Patterning and Electronic Tuning of Laser Scribed Graphene for Flexible All-Carbon Devices," ACS Nano, vol. 6, Issue 2, Jan. 13, 2012, American Chemical Society, p. 1395-1403.
Su, Zujin et al., "Scalable fabrication of $MnO_2$ nanostructure deposited on free-standing Ni nanocone arrays for ultrathin, flexible, high-performance micro-supercapacitor," Energy and Environmental Science, vol. 7, May 28, 2014, The Royal Society of Chemistry, pp. 2652-2659.
Sumboja, Afriyanti et al., "Large Areal Mass, Flexible and Free-Standing Reduced Graphene Oxide/Manganese Dioxide Paper for Asymmetric Supercapacitor Device," Advanced Materials, vol. 25, Issue 20, May 28, 2013, WILEY-VCH Verlag GmbH & Co. KGaA, Weinheim, pp. 2809-2815.
Tian, Yuyu et al., "Synergy of $W_{18}O_{49}$ and Polyaniline for Smart Supercapacitor Electrode Integrated with Energy Level Indicating Functionality," Nano Letters, vol. 14, Issue 4, Mar. 4, 2014, American Chemical Society, pp. 2150-2156.
Toupin, Mathieu et al., "Charge Storage Mechanism of $MnO_2$ Electrode Used in Aqueous Electrochemical Capacitor," Chemistry of Materials, vol. 16, Issue 16, Jul. 16, 2004, American Chemical Society, pp. 3184-3190.
Tran, Henry D. et al.,"The oxidation of aniline to produce "polyaniline": a process yielding many different nanoscale structures," Journal of Materials Chemistry, vol. 21, Issue 11, Nov. 25, 2010, The Royal Society of Chemistry, pp. 3534-3550.
Viculis, Lisa M. et al., "A Chemical Route to Carbon Nanoscrolls," Science, vol. 299, Issue 5611, Feb. 28, 2003, American Association for the Advancement of Science, 2 pages.
Vonlanthen, David et al., "A Stable Polyaniline-Benzoquinone-Hydroquinone Supercapacitor," Advanced Materials, vol. 26, Issue 30, Jun. 13, 2014, WILEY-VCH Verlag GmbH & Co., pp. 1-6.
Wallace, Gordon G. et al., "Processable aqueous dispersions of graphene nanosheets," Nature Nanotechnology, vol. 3, Issue 2, 2008, Nature Publishing Group, pp. 101-105.
Wang, Gongkai et al., "Flexible Pillared Graphene-Paper Electrodes for High-Performance Electrochemical Supercapacitors," Small, vol. 8, Issue 3, Dec. 8, 2011, pp. 452-459.
Wang, Guoping et al., "A review of electrode materials for electrochemical supercapacitors," Chemical Society Reviews, vol. 41, Jul. 21, 2011, The Royal Society of Chemistry, pp. 797-828.
Wang, Guoxiu et al., "Graphene nanosheets for enhanced lithium storage in lithium ion batteries," Carbon, vol. 47, Issue 8, Apr. 1, 2009, Elsevier Ltd., pp. 2049-2053.
Wang, Hailiang et al., "$Mn_3O_4$-Graphene Hybrid as a High-Capacity Anode Material for Lithium Ion Batteries," Journal of the American Chemical Society, vol. 132, Issue 40, Oct. 13, 2010, American Chemical Society, pp. 13978-13980.
Wang, Huanlei et al., "Graphene-Nickel Cobaltite Nanocomposite Asymmetrical Supercapacitor with Commercial Level Mass Loading," Nano Research, vol. 5, Issue 9, Sep. 2012, Tsinghua University Press and Springer-Verlag Berlin Heidelberg, pp. 605-617.
Wang, Kai et al., "Flexible supercapacitors based on cloth-supported electrodes of conducting polymer nanowire array/SWCNT composites," Journal of Materials Chemistry, vol. 21, Issue 41, Sep. 20, 2011, The Royal Society of Chemistry, pp. 16373-16378.
Office Action for Mexican Patent Application No. MX/a/2016/016239, dated Feb. 26, 2020, 5 pages.
Supplemental Notice of Allowability for U.S. Appl. No. 14/945,232, dated Feb. 26, 2020, 5 pages.
Notification of Reasons for Rejection for Japanese Patent Application No. 2017-526533, dated Mar. 16, 2020, 7 pages.
Second Office Action for Chinese Patent Application No. 2016800753323, dated Mar. 5, 2020, 15 pages.
Non-Final Office Action for U.S. Appl. No. 16/692,123, dated Dec. 27, 2019, 11 pages.
Non-Final Office Action for U.S. Appl. No. 15/688,342, dated Apr. 9, 2020, 10 pages.
Office Action for Eurasian Patent Application No. 201990587/31, dated Mar. 26, 2020, 4 pages.
Partial Supplemental European Search Report for European Patent Application No. 17847303.9, dated Apr. 3, 2020, 10 pages.
First Office Action for Chinese Patent Application No. 2017800249783, dated Jan. 6, 2020, 15 pages.
Final Office Action for U.S. Appl. No. 15/630,758, dated Apr. 15, 2020, 13 pages.
Author Unknown, "Sulfuric Acid—Density," The Engineering Toolbox, accessed Apr. 10, 2020 at https://www.engineeringtoolbox.com/indsulfuric-acid-density-d_2163.html, 6 pages.
Kang, J.H et al., "Hidden Second Oxidation Step of Hummers Method," Chemistry of Materials, vol. 28, 2016, American Chemical Society, pp. 756-764.
Dubal, D. P., et al., "Hybrid energy storage: the merging of battery and supercapacitor chemistries," Chemical Society Review, vol. 44, No. 7, 2015, pp. 1777-1790.
Garg, R. et al., "Nanowire Mesh Templated Growth of Out-of-Plane Three-Dimensional Fuzzy Graphene," ACS Nano, vol. 11, 2017, American Chemical Society, pp. 6301-6311.
Gong, M., et al., "Ultrafast high-capacity NiZn battery with NiAlCo-layered double hydroxide," Energy & Environmenta Science, vol. 7, No. 6, 2014, pp. 2025-2032.
Humble, P. H., et al., "Microscopic nickel-zinc batteries for use in autonomous microsystems," Journal of the Electrochemical Society, vol. 148, No. 12, 2001, pp. A1357-A1361.
Li, Qintao et al., "Carbon nanotubes coated by carbon nanoparticles of turbostratic stacked graphenes," Carbon, vol. 46, 2008, Elsevier Ltd., pp. 434-439.

(56) References Cited

OTHER PUBLICATIONS

Mishra, G., et al., "Layered double hydroxides: A brief review from fundamentals to application as evolving biomaterials," Applied Clay Science, vol. 153, 2018, Elsevier B.V., pp. 172-186.
Parker, J. F., et al. "Rechargeable nickel-3D zinc batteries: An energy-dense, safer alternative to lithium-ion," Science, vol. 356, No. 6336, 2017, American Association for the Advancement of Science, pp. 415-418.
Examination Report No. 1 for Australian Patent Application No. 2019250120, dated Apr. 24, 2020, 4 pages.
Non-Final Office Action for U.S. Appl. No. 16/033,266, dated Apr. 29, 2020, 12 pages.
Office Action for Eurasian Patent Application No. 201790003, dated Feb. 26, 2020, 6 pages.
First Office Action and Search Report for Chinese Patent Application No. 201811438766.2, dated Mar. 31, 2020, 32 pages.
Office Action for Vietnamese Patent Application No. 1-2016-05086, dated May 29, 2020, 2 pages.
Decision of Rejection for Chinese Patent Application No. 201580072540.3, dated Apr. 22, 2020, 8 pages.
Notice of Allowance for U.S. Appl. No. 15/319,286, dated Oct. 1, 2018, 8 pages.
Corrected Notice of Allowability for U.S. Appl. No. 15/319,286, dated Oct. 29, 2018, 5 pages.
Corrected Notice of Allowability for U.S. Appl. No. 15/319,286, dated Nov. 30, 2018, 5 pages.
Corrected Notice of Allowability for U.S. Appl. No. 15/319,286, dated Jan. 18, 2019, 5 pages.
Notification of the First Office Action for Chinese Patent Application No. 201580043429.1, dated Oct. 29, 2018, 19 pages.
Advisory Action for U.S. Appl. No. 14/945,232, dated Oct. 15, 2018, 3 pages.
Non-Final Office Action for U.S. Appl. No. 14/945,232, dated Jan. 9, 2019, 7 pages.
Extended European Search Report for European Patent Application No. 15861794.4, dated Oct. 2, 2018, 13 pages.
Final Office Action for U.S. Appl. No. 15/382,871, dated Jan. 25, 2019, 16 pages.
Non-Final Office Action for U.S. Appl. No. 15/410,404, dated Sep. 27, 2018, 9 pages.
Final Office Action for U.S. Appl. No. 15/472,409, dated Jan. 18, 2019, 12 pages.
International Preliminary Report on Patentability for International Patent Application No. PCT/US2017/024716, dated Oct. 11, 2018, 10 pages.
International Preliminary Report on Patentability for International Patent Application No. PCT/US2017/038992, dated Jan. 3, 2019, 10 pages.
International Preliminary Report on Patentability for International Patent Application No. PCT/US2017/023632, dated Oct. 4, 2018, 8 pages.
Invitation to Pay Additional Fees for International Patent Application No. PCT/US2018/041728, dated Sep. 12, 2018, 2 pages.
International Search Report and Written Opinion for International Patent Application No. PCT/US2018/041728, dated Nov. 9, 2018, 10 pages.
Huang, L. et al., "Pulsed laser assisted reduction of graphene oxide," Carbon, vol. 49, 2011, Elsevier, pp. 2431-2436.
Kumar, P. et al., "Graphene produced by radiation-induced reduction of graphene oxide," Sep. 26, 2010, DOI: DOI:10.1142/S0219581X11008824, 23 pages.
Park, S. et al., "Colloidal Suspensions of Highly Reduced Graphene Oxide in a Wide Variety of Organic Solvents," Nano Letters, vol. 9, No. 4, 2009, American Chemical Society, pp. 1593-1597.
Non-Final Office Action for U.S. Appl. No. 15/427,210, dated Feb. 28, 2019, 17 pages.
Applicant-Initiated Interview Summary for U.S. Appl. No. 15/427,210, dated May 29, 2019, 3 pages.
Notice of Reexamination for Chinese Patent Application No. 201280070343.4, dated Jun. 27, 2019, 14 pages.
Examination Report for European Patent Application No. 12874989.2, dated Mar. 5, 2019, 5 pages.
Notice of Preliminary Rejection for Korean Patent Application No. 10-2014-7020353, dated Apr. 15, 2019, 11 pages.
Non-Final Office Action for U.S. Appl. No. 15/612,405, dated Jun. 18, 2019, 12 pages.
Non-Final Office Action for U.S. Appl. No. 16/029,930, dated Apr. 3, 2019, 13 pages.
Examination Report No. 1 for Australian Patent Application No. 2015277264, dated Mar. 7, 2019, 4 pages.
Notification of the Second Office Action for Chinese Patent Application No. 201580043429.1, dated Jun. 20, 2019, 9 pages.
Notice of Reasons for Rejection for Japanese Patent Application No. 2016-573846, dated Feb. 26, 2019, 8 pages.
Search Report for Japanese Patent Application No. 2016-573846, dated Feb. 28, 2019, 44 pages.
Interview Summary for U.S. Appl. No. 14/945,232, dated Apr. 11, 2019, 3 pages.
Final Office Action for U.S. Appl. No. 14/945,232, dated Jul. 17, 2019, 8 pages.
Examination Report No. 1 for Australian Patent Application No. 2015349949, dated Mar. 8, 2019, 4 pages.
Notice of Acceptance for Australian Patent Application No. 2015349949, dated Jul. 12, 2019, 3 pages.
Notification of the Second Office Action for Chinese Patent Application No. 201580072540.3, dated Mar. 7, 2019, 12 pages.
Official Action for Eurasian Patent Application No. 201791078, dated Mar. 27, 2019, 5 pages.
Interview Summary for U.S. Appl. No. 15/382,871, dated Apr. 1, 2019, 10 pages.
Advisory Action for U.S. Appl. No. 15/382,871, dated Apr. 24, 2019, 3 pages.
Notice of Allowance for U.S. Appl. No. 15/382,871, dated May 17, 2019, 10 pages.
Extended European Search Report for European Patent Application No. 16879927.8, dated Jul. 9, 2019, 14 pages.
Final Office Action for U.S. Appl. No. 15/410,404, dated Feb. 21, 2019, 9 pages.
Non-Final Office Action for U.S. Appl. No. 15/410,404, dated May 24, 2019, 9 pages.
Applicant-Initiated Interview Summary for U.S. Appl. No. 16/029,930, dated Jul. 29, 2019, 4 pages.
Partial Supplementary European Search Report for European Patent Application No. 17741923.1, dated Jul. 23, 2019, 13 pages.
Non-Final Office Action for U.S. Appl. No. 15/472,409, dated May 31, 2019, 12 pages.
Non-Final Office Action for U.S. Appl. No. 15/688,342, dated Mar. 26, 2019, 9 pages.
International Preliminary Report on Patentability for International Patent Application No. PCT/US2017/048883, dated Mar. 14, 2019, 7 pages.
Non-Final Office Action for U.S. Appl. No. 15/466,425, dated Jul. 10, 2019, 8 pages.
Notification of the Third Office Action for Chinese Patent Application No. 201580072540.3, dated Jul. 17, 2019, 9 pages.
Applicant-Initiated Interview Summary for U.S. Appl. No. 15/410,404, dated Aug. 2, 2019, 3 pages.
Wikipedia, "Ferromagnetism," Feb. 13, 2017, Retrieved Aug. 7, 2018 from https://en.wikipedia.org/w/index.php?title=Ferromagnetism&oldid=765289868, 1 page.
Grosu, Yaroslav et al., "Natural Magnetite for thermal energy storage: Excellent thermophysical properties, reversible latent heat transition and controlled thermal conductivity," Solar Energy Materials & Solar Cells, vol. 161, Available online Dec. 6, 2016, Elsevier B.V., pp. 170-176.
Hwang, J. Y., et al., "Boosting the Capacitance and Voltage of Aqueous Supercapacitors via Redox Charge Contribution from both Electrode and Electrolyte," Nano Today, vol. 15, Available online Jul. 22, 2017, pp. 15-25.
Karami, Hassan et al., "Sodium Sulfate Effects on the Electrochemical Behaviors of Nanostructured Lead Dioxide and Commercial Positive Plates of Lead-Acid Batteries," International Journal of Electrochemical Science, vol. 5, 2010, ESG, pp. 1046-1059.

(56) References Cited

OTHER PUBLICATIONS

Lee, Juhan, et al., "High Performance Hybrid Energy Storage with Potassium Ferricyanide Redox Electrolyte," Applications of Materials and Interfaces, vol. 8, Aug. 2016, ACS, pp. 23676-23687.
Notice of Allowance for U.S. Appl. No. 15/612,405, dated Sep. 8, 2020, 7 pages.
Examination Report for Indian Patent Application No. 201817023184, dated Aug. 13, 2020, 6 pages.
Examination Report for Indian Patent Application No. 201817034180, dated Aug. 13, 2020, 6 pages.
Examination Report for European Patent Application No. 17816292.1, dated Aug. 24, 2020, 4 pages.
Examination Report for Indian Patent Application No. 201817033309, dated Aug. 28, 2020, 6 pages.
Invitation to Pay Additional Fees for International Patent Application No. PCT/US2018/036846, dated Aug. 24, 2018, 2 pages.
International Search Report and Written Opinion for International Patent Application No. PCT/US2018/036846, dated Nov. 9, 2018, 14 pages.
International Preliminary Report on Patentability for International Patent Application No. PCT/US2018/036846, dated Dec. 26, 2019, 10 pages.
Non-Final Office Action for U.S. Appl. No. 16/0004,818, dated Jun. 24, 2020, 18 pages.
Wang, Xu et al., "Manganese Oxide Micro-Supercapacitors with Ultra-high Areal Capacitance," Electronic Supplementary Material (ESI) for Nanoscale, vol. 5, Mar. 21, 2013, The Royal Society of Chemistry, 6 pages.
Wang, Xuebin et al., "Three-dimensional strutted graphene grown by substrate-free sugar blowing for high-power-density supercapacitors," Nature Communications, vol. 4, Issue 2905, Dec. 16, 2013, Macmillan Publishers Limited, pp. 1-8.
Wassei, Jonathan K. et al., "Oh the Places You'll Go with Graphene", Accounts of Chemical Research, Dec. 20, 2012, Vers. 9, 11 pages.
Weng, Zhe et al., "Graphene-Cellulose Paper Flexible Supercapacitors," Advanced Energy Materials, vol. 1, Issue 5, Aug. 10, 2011, WILEY-VCH Verlag GmbH & Co., pp. 917-922.
Wu, Zhong-Shuai et al., "Graphene Anchored with $Co_3O_4$ Nanoparticles as Anode of Lithium Ion Batteries with Enhanced Reversible Capacity and Cyclic Performance," ACS Nano, vol. 4, Issue 6, May 10, 2010, American Chemical Society, pp. 3187-3194.
Xie, Guoxin, "Direct Electrochemical Synthesis of Reduced Graphene Oxide (rGO)/Copper Composite Films and Their Electrical/Electroactive Properties," Applied Materials & Interfaces, vol. 6, Issue 10, May 1, 2014, American Chemical Society, pp. 7444-7455.
Xu, Bin et al., "Sustainable nitrogen-doped porous carbon with high surface areas prepared from gelatin for supercapacitors," Journal of Materials Chemistry, vol. 22, Issue 36, Jul. 25, 2012, The Royal Society of Chemistry, pp. 19088-19093.
Xu, Jing et al., "Flexible Asymmetric Supercapacitors Based upon $Co_9S_8$ Nanorod//$Co_3O_4$@$RuO_2$ Nanosheet Arrays on Carbon Cloth," ACS Nano, vol. 7, Issue 6, May 6, 2013, American Chemical Society, pp. 5453-5462.
Xu, Yuxi et al., "Flexible Solid-State Supercapacitors Based on Three-Dimensional Graphene Hydrogel Films," ACS Nano, vol. 7, Issue 5, Apr. 4, 2013, American Chemical Society, 8 pages.
Xu, Zhanwei et al., "Electrochemical Supercapacitor Electrodes from Sponge-like Graphene Nanoarchitectures with Ultrahigh Power Density," The Journal of Physical Chemistry Letters, vol. 3, Issue 20, Sep. 25, 2012, American Chemical Society, pp. 2928-2933.
Yan, Jun et al., "Fast and reversible surface redox reaction of graphene-MnO2composites as supercapacitor electrodes," Carbon, vol. 48, Issue 13, Jun. 25, 2010, Elsevier Ltd., pp. 3825-3833.
Yan, Jun et al., "Recent Advances in Design and Fabrication of Electrochemical Supercapacitors with High Energy Densities," Advanced Energy Materials, vol. 4, Issue 4, 1300816, Dec. 23, 2013, WILEY-VCH Verlag GmbH & Co., pp. 1-43.
Yang, Xiaowei et al, "Bioinspired Effective Prevention of Restacking in Multilayered Graphene Films: Towards the Next Generation of High-Performance Supercapacitors," Advanced Materials, vol. 23, Issue 25, May 10, 2011, WILEY-VCH Verlag GmbH & Co., pp. 2833-2838.
Yang, Peihua et al., "Low-Cost High-Performance Solid-State Asymmetric Supercapacitors Based on $MnO_2$ Nanowires and $Fe_2O_3$ Nanotubes," Nano Letters, vol. 14, Issue 2, Jan. 1, 2014, American Chemical Society, pp. 731-736.
Yang, Xiaowei et al, "Liquid-Mediated Dense Integration of Graphene Materials for Compact Capacitive Energy Storage," Science, vol. 341, Issue 6145, Aug. 2, 2013, American Association for the Advancement of Science, 5 pages.
Yoo, Eunjoo et al., "Large Reversible Li Storage of Graphene Nanosheet Families for Use in Rechargeable Lithium Ion Batteries," Nano Letters, vol. 8, Issue 8, Jul. 24, 2008, American Chemical Society, pp. 2277-2282.
Yoo, Jung Joon et al., "Ultrathin Planar Graphene Supercapacitors," Nano Letters, vol. 11, Issue 4, Mar. 7, 2011, American Chemical Society, pp. 1423-1427.
Yu, Dingshan et al., "Scalable synthesis of hierarchically structured carbon nanotube-graphene fibres for capacitive energy storage," Nature Nanotechnology, vol. 9, Issue 7, May 11, 2014, Macmillan Publishers Limited, pp. 1-8.
Yu, Guihua et al., "Solution-Processed Graphene/$MnO_2$ Nanostructured Textiles for High-Performance Electrochemical Capacitors," Nano Letters, vol. 11, Issue 7, Jun. 13, 2011, American Chemical Society, pp. 2905-2911.
Yu, Pingping et al., "Graphene-Wrapped Polyaniline Nanowire Arrays on Nitrogen-Doped Carbon Fabric as Novel Flexible Hybrid Electrode Materials for High-Performance Supercapacitor," Langmuir, vol. 30, Issue 18, Apr. 24, 2014, American Chemical Society, pp. 5306-5313.
Yu, Pingping et al., "Polyaniline Nanowire Arrays Aligned on Nitrogen-Doped Carbon Fabric for High-Performance Flexible Supercapacitors," Langmuir, vol. 29, Issue 38, Aug. 28, 2013, American Chemical Society, 8 pages.
Yu, Zenan et al., "Supercapacitor electrode materials: nanostructures from 0 to 3 dimensions," Energy & Environmental Science, vol. 8, Issue 3, Dec. 3, 2014, The Royal Society of Chemistry, pp. 702-730.
Zhang, Jintao et al., "A high-performance asymmetric supercapacitor fabricated with graphene-based electrodes," Energy & Environmental Science, vol. 4, Issue 10, Aug. 2, 2011, The Royal Society of Chemistry, pp. 4009-4015.
Zhang, Li et al., "High Voltage Super-capacitors for Energy Storage Devices Applications," 14th Symposium on Electromagnetic Launch Technology, Jun. 10-13, 2008, IEEE, pp. 1-4.
Zhang, Long et al., "Porous 3D graphene-based bulk materials with exceptional high surface area and excellent conductivity for supercapacitors," Scientific Reports, vol. 3, Issue 1408, Mar. 11, 2013, Nature Publishing Group, pp. 1-9.
Zhang, Yonglai et al., "Direct imprinting of microcircuits on graphene oxides film by femtosecond laser reduction," Nano Today, vol. 5, Issue 1, Jan. 19, 2010, Elsevier Ltd., pp. 15-20.
Zhang, Zheye et al., "Facile Synthesis of 3D $MnO_2$-Graphene and Carbon Nanotube-Graphene Composite Networks for High-Performance, Flexible, All-Solid-State Asymmetric Supercapacitors," Advanced Energy Materials, vol. 4, Issue 10, Jul. 15, 2014, WILEY-VCH Verlag GmbH & Co. KGaA, Weinheim, pp. 1-9.
Zhang, Zhongsheng et al., "A New-Type Ordered Mesoporous Carbon/Polyaniline Composites Prepared by a Two-step Nanocasting Method for High Performance Supercapacitor Applications," Journal of Materials Chemistry A, vol. 2, Issue 39, Aug. 13, 2014, Royal Society of Chemistry, pp. 1-25.
Zhao, Xin et al., "Incorporation of Manganese Dioxide within Ultraporous Activated Graphene for High-Performance Electrochemical Capacitors," ACS Nano, vol. 6, Issue 6, May 3, 2012, American Chemical Society, pp. 5404-5412.
Zhi, Mingjia et al, "Nanostructured carbon-metal oxide composite electrodes for supercapacitors: a review," Nanoscale, vol. 5, Issue 1, Oct. 23, 2012, The Royal Society of Chemistry, pp. 72-88.
Zhou, Chuanqiang et al., "Synthesis of Polyaniline Hierarchical Structures in a Dilute SDS/HCl Solution Nanostructure-Covered Rectangular Tubes," Macromolecules, vol. 42, Issue 4, Jan. 27, 2009, American Chemical Society, pp. 1252-1257.

(56) References Cited

OTHER PUBLICATIONS

Zhou, Guangmin et al., "Graphene-Wrapped $Fe_3O_4$ Anode Material with Improved Reversible Capacity and Cyclic Stability for Lithium Ion Batteries," Chemistry of Materials, vol. 22, Issue 18, Aug. 26, 2010, American Chemical Society, pp. 5306-5313.

Zhu, Xianjun et al., "Nanostructured Reduced Graphene Oxide/$Fe_2O_3$ Composite as a High-Performance Anode Material for Lithium Ion Batteries," ACS Nano, vol. 5, Issue 4, Mar. 28, 2011, American Chemical Society, pp. 3333-3338.

Zhu, Yanwu et al., "Carbon-Based Supercapacitors Produced by Activation of Graphene," Science, vol. 332, May 12, 2011, www.sciencemag.org, pp. 1537-1541.

Zoski, Cynthia G., "Handbook of Electrochemistry," First Edition, 2007, Las Cruces, New Mexico, USA, Elsevier B.V., 935 pages.

Non-Final Office Action for U.S. Appl. No. 13/725,073, dated Apr. 15, 2016, 32 pages.

Final Office Action for U.S. Appl. No. 13/725,073, dated Oct. 4, 2016, 38 pages.

First Examination Report for Australian Patent Application No. 2012378149, dated Jul. 28, 2016, 3 pages.

First Office Action for Chinese Patent Application No. 201280070343.4, dated Jul. 23, 2015, 29 pages.

Second Office Action for Chinese Patent Application No. 201280070343.4, dated Apr. 6, 2016, 8 pages.

Third Office Action for Chinese Patent Application No. 201280070343.4, dated Sep. 7, 2016, 25 pages.

Extended European Search Report for European Patent Application No. 12874989.2, dated Jun. 17, 2015, 6 pages.

Notice of Reason for Rejection for Japanese Patent Application No. 2014-548972, dated Feb. 7, 2017, 5 pages.

International Search Report and Written Opinion for PCT/US2012/071407, dated Nov. 12, 2013, 9 pages.

International Preliminary Report on Patentability for PCT/US2012/071407 dated Jul. 3, 2014, 6 pages.

Non-Final Office Action for U.S. Appl. No. 14/382,463, dated Jan. 6, 2017, 23 pages.

Notice of Allowance for U.S. Appl. No. 14/382,463, dated Apr. 6, 2017, 7 pages.

First Examination Report for Australian Patent Application No. 2013230195, dated May 27, 2016, 4 pages.

First Office Action and Search Report for Chinese Patent Application No. 201380023699.7, dated Nov. 21, 2016, 21 pages.

Extended European Search Report for European Patent Application No. 13757195.6, dated Jul. 1, 2015, 9 pages.

Gao, Yu et al., "High power supercapcitor electrodes based on flexible TiC-CDC nano-felts," Journal of Power Sources, vol. 201, Issue 1, Mar. 2012, Elsevier B.V., pp. 368-375.

Gao, Lijun et al., "Power Enhancement of an Actively Controlled Battery/Ultracapacitor Hybrid," IEEE Transactions on Power Electronics, vol. 20, Issue 1, Jan. 2005, IEEE, pp. 236-243.

Ghasemi, S. et al., "Enhancement of electron transfer kinetics on a polyaniline-modified electrode in the presence of anionic dopants," Journal of Solid State Electrochemistry, vol. 12, Issue 3, Jul. 28, 2007, Springer-Verlag, pp. 259-268.

Ghidiu, Michael et al., "Conductive two-dimensional titanium carbide 'clay' with high volumetric capacitance," Nature, vol. 516, Dec. 4, 2014, Macmillan Publishers Limited, pp. 78-81.

Gilje, Scott et al., "A Chemical Route to Graphene for Device Applications," Nano Letters, vol. 7, Issue 11, Oct. 18, 2007, American Chemical Society, pp. 3394-3398.

Gilje, Scott et al., "Photothermal Deoxygenation of Graphene Oxide for Patterning and Distributed Ignition Applications," Advanced Materials, vol. 22, Issue 3, Oct. 26, 2009, WILEY-VCH Verlag GmbH & Co. KGaA, Weinheim, Germany, pp. 419-423.

Glavin, M.E. et al., "A Stand-alone Photovoltaic Supercapacitor Battery Hybrid Energy Storage System," Proceedings of the 13th International Power Electronics and Motion Control Conference (EPE-PEMC), Sep. 1-3, 2008, Poznań, Poland, IEEE, pp. 1688-1695.

Gogotsi, Y. et al., "True Performance Metrics in Electrochemical Energy Storage," Science Magazine, vol. 334, Issue 6058, Nov. 18, 2011, 4 pages.

Gracia, J. et al., "Corrugated layered heptazine-based carbon nitride: the lowest energy modifications of $C_3N_4$ ground state," Journal of Materials Chemistry, vol. 19, 2009, pp. 3013-3019.

Griffiths, Katie et al., "Laser-scribed graphene presents an opportunity to print a new generation of disposable electrochemical sensors," Nanoscale, vol. 6, Sep. 22, 2014, The Royal Society of Chemistry, pp. 13613-13622.

Guardia, L. et al., "UV light exposure of aqueous graphene oxide suspensions to promote their direct reduction, formation of graphene-metal nanoparticle hybrids and dye degradation," Carbon, vol. 50, Issue 3, Oct. 12, 2011, Elsevier Ltd., pp. 1014-1024.

Guerrero-Contreras, Jesus et al., "Graphene oxide powders with different oxidation degree, prepared by synthesis variations of the Hummers method," Materials Chemistry and Physics, vol. 153, Mar. 1, 2015, Elsevier B.V., pp. 1-12.

Günes, Hethullah et al., "Layer-by-Layer Doping of Few-Layer Graphene Film," ACS Nano, vol. 4, Issue 8, Jul. 27, 2010, American Chemical Society, pp. 4595-4600.

He, Xinping et al., "A new nanocomposite: Carbon cloth based polyaniline for an electrochemical supercapacitor," Electrochimica Acta, vol. 111, Aug. 17, 2013, Elsevier Ltd., pp. 210-215.

Hu, Liangbing et al., "Symmetrical $MnO_2$-Carbon Nanotube-Textile Nanostructures for Wearable Pseudocapacitors with High Mass Loading," ACS Nano, vol. 5, Issue 11, Sep. 16, 2011, American Chemical Society, pp. 8904-8913.

Huang, Yi et al., "An Overview of the Applications of Graphene-Based Materials in Supercapacitors," Small, vol. 8, Issue 12, Jun. 25, 2012, Wiley-VCH Verlag GmbH & Co. KGaA, Weinheim, pp. 1-30.

Huang, Ming et al., "Self-Assembly of Mesoporous Nanotubes Assembled from Interwoven Ultrathin Birnessite-type $MnO_2$ Nanosheets for Asymmetric Supercapacitors," Scientific Reports, vol. 4, Issue 3878, Jan. 27, 2014, ww.nature.com/scientificreports, pp. 1-8.

Hwang, Jee Y. et al., "Direct preparation and processing of graphene/RuO2 nanocomposite electrodes for high-performance capacitive energy storage," Nano Energy, vol. 18, Sep. 25, 2015, Elsevier B V., pp. 57-70.

Jana, Milan et al., "Non-covalent functionalization of reduced graphene oxide using sulfanilic acid azocromotrop and its application as a supercapacitor electrode material," Journal of Materials Chemistry A, vol. 3, Issue 14, Feb. 24, 2015, The Royal Society of Chemistry, pp. 7323-7331.

Ji, Junyi et al., "Nanoporous $Ni(OH)_2$ Thin Film on 3D Ultrathin-Graphite Foam for Asymmetric Supercapacitor," ACS Mano, vol. 7, Issue 7, Jun. 11, 2013, American Chemical Society, pp. 6237-6243.

Jimbo, "Transistors," Sparkfun, https://learn.sparkfun.com/tutorials/transistors/extending-the-water-analogy, accessed Dec. 14, 2015, SparkFun Electronics, 3 pages.

Jin, H. Y. et al., "Controllable functionalized carbon fabric for high-performance all-carbon-based supercapacitors," RSC Advances, vol. 4, Issue 62, Jul. 15, 2014, The Royal Society of Chemistry, pp. 33022-33028.

Kang, Yu Jin et al., "All-solid-state flexible supercapacitors based on papers coated with carbon nanotubes and ionic-liquid-based gel electrolytes," Nanotechnology, vol. 23, Issue 6, Jan. 17, 2012, IOP Publishing Ltd, pp. 1-6.

Khaligh, Alireza et al., "Battery, Ultracapacitor, Fuel Cell, and Hybrid Energy Storage Systems for Electric, Hybrid Electric, Fuel Cell, and Plug-In Hybrid Electric Vehicles: State of the Art," IEEE Transactions on Vehicular Technology, vol. 59, Issue 6, Jul. 2010, IEEE, pp. 2806-2814.

Khomenko, V. et al., "Optimisation of an asymmetric manganese oxide/activated carbon capacitor working at 2 V in aqueous medium," Journal of Power Sources, vol. 153, Issue 1, Mar. 14, 2005, Elsevier B.V., pp. 183-190.

Kiani, Mohammad Ali et al., "Fabrication of High Power LiNi0.5Mn1.5O4 Battery Cathodes by Nanostructuring of Electrode Materials," RSC Advances, vol. 5, Issue 62, May 26, 2015, The Royal Society of Chemistry, pp. 1-6.

(56) References Cited

OTHER PUBLICATIONS

Kiani, M.A. et al., "Size effect investigation on battery performance: Comparison between micro- and nano-particles of β-Ni(OH)$_2$ as nickel battery cathode material," Journal of Power Sources, vol. 195, Issue 17, Apr. 2, 2010, Elsevier B.V., pp. 5794-5800.

Kiani, M.A. et al., "Synthesis of Nano- and Micro-Particles of LiMn$_2$O$_4$: Electrochemical Investigation and Assessment as a Cathode in Li Battery," International Journal of Electrochemical Science, vol. 6, Issue 7, Jul. 1, 2011, ESG, pp. 2581-2595.

Kovtyukhova, Nina, I. et al., "Layer-by-Layer Assembly of Ultrathin Composite Films from Micron-Sized Graphite Oxide Sheets and Polycations," Kovtyukhova, et al, Chemistry of Materials, vol. 11, Issue 3, Jan. 28, 1999, American Chemical Society, pp. 771-778.

Lam, L.T. et al., "Development of ultra-battery for hybrid-electric vehicle applications," Journal of Power Sources, vol. 158, Issue 2, May 2, 2006, Elsevier B.V., pp. 1140-1148.

Lang, Xingyou et al., "Nanoporous metal/oxide hybrid electrodes for electrochemical supercapacitors," Nature Nanotechnology, vol. 6, Apr. 2011, Macmillan Publishers Limited, pp. 232-236.

Lee, Kyu Hyung et al., "Large scale production of highly conductive reduced graphene oxide sheets by a solvent-free low temperature reduction," Carbon, vol. 69, Dec. 16, 2013, Elsevier Ltd., pp. 327-335.

Lee, Kyoung, G. et al, "Sonochemical-assisted synthesis of 3D graphene/nanoparticle foams and their application in supercapacitor," Ultrasonics Sonochemistry, vol. 22, May 2, 2014, Elsevier B V., pp. 422-428.

Lee, Seung Woo et al., "Carbon Nanotube/Manganese Oxide Ultrathin Film Electrodes for Electrochemical Capacitors," ACS Nano, vol. 4, Issue 7, Jun. 16, 2010, American Chemical Society, pp. 3889-3896.

Lei, Zhibin et al., "Platelet CMK-5 as an Excellent Mesoporous Carbon to Enhance the Pseudocapacitance of Polyaniline," ACS Applied Materials & Interfaces, vol. 5, Issue 15, Jul. 12, 2013, American Chemical Society, pp. 7501-7508.

Li, Dan et al., "Processable aqueous dispersions of graphene nanosheets," Nature Nanotechnology, vol. 3, Feb. 2008, Nature Publishing Group, pp. 101-105.

Li, Lei et al., "Nanocomposite of Polyaniline Nanorods Grown on Graphene Nanoribbons for Highly Capacitive Pseudocapacitors," ACS Applied Materials and Interfaces, vol. 5, Issue 14, Jun. 21, 2013, American Chemical Society, 6 pages.

Li, Peixu et al., "Core-Double-Shell, Carbon Nanotube@Polypyrrole@MnO$_2$ Sponge as Freestanding, Compressible Supercapacitor Electrode," ACS Applied Materials and Interfaces, vol. 6, Issue 7, Mar. 12, 2014, American Chemical Society, pp. 5228-5234.

Li, Qi et al., "Design and Synthesis of MnO$_2$/Mn/MnO$_2$ Sandwich-Structured Nanotube Arrays with High Supercapacitive Performance for Electrochemical Energy Storage," Nano Letters, vol. 12, Issue 7, Jun. 25, 2012, American Chemical Society, pp. 3803-3807.

Li, Yingzhi et al., "Oriented Arrays of Polyaniline Nanorods Grown on Graphite Nanosheets for an Electrochemical Supercapacitor," Langmuir, vol. 29, Issue 1, Dec. 3, 2012, American Chemical Society, 8 pages.

Li, Zhe-Fei et al., "Fabrication of high-surface-area graphene/polyaniline nanocomposites and their application in supercapacitors," ACS Applied Materials & Interfaces, vol. 5, Issue 7, Mar. 12, 2013, American Chemical Society, pp. 1-25.

Lin, Jian et al., "3-Dimensional Graphene Carbon Nanotube Carpet-Based Microsupercapacitors with High Electrochemical Performance," Nano Letters, vol. 13, Issue 1, Dec. 13, 2012, American Chemical Society, pp. 72-78.

Linden, David et al., "Handbook of Batteries," McGraw-Hill Handbooks, Third Edition, 2010, New York, The McGraw-Hill Companies, Inc., 1,454 pages.

Liu, Wenwen et al., "Novel and high-performance asymmetric micro-supercapacitors based on graphene quantum dots and polyaniline nanofibers," Nanoscale, vol. 5, Apr. 24, 2013, The Royal Society of Chemistry, pp. 6053-3062.

Liu, Wen-Wen et al., "Superior Micro-Supercapacitors Based on Graphene Quantum Dots," Advanced Functional Materials, vol. 23, Issue 33, Mar. 26, 2013, WILEY-VCH Verlag GmbH & Co. KGaA, Weinheim, pp. 4111-4122.

Liu, Yongfeng et al., "Advanced hydrogen storage alloys for Ni/MH rechargeable batteries," Journal of Materials Chemistry, vol. 21, Issue 11, Dec. 15, 2010, The Royal Society of Chemistry, pp. 4743-4755.

Long, Jeffrey W. et al., "Asymmetric electrochemical capacitors—Stretching the limits of aqueous electrolytes," MRS Bulletin, vol. 36, Jul. 2011, Materials Research Society, pp. 513-522.

Lu, Xihong et al., "Stabilized TiN Nanowire Arrays for High-Performance and Flexible Supercapacitors," Nano Letters, vol. 12, Issue 10, Sep. 4, 2012, American Chemical Society, 6 pages.

Lukatskaya, Maria R. et al., "Cation Intercalation and High Volumetric Capacitance of Two-Dimensional Titanium Carbide," Science, vol. 341, Issue 6153, Sep. 27, 2013, American Association for the Advancement of Science, pp. 1502-1505.

Lukic, Srdjam, M. et al., "Power Management of an Ultracapacitor/Battery Hybrid Energy Storage System in an HEV," IEEE Vehicle Power and Propulsion Conference (VPPC), Sep. 6-8, 2006, IEEE, 6 pages.

Notice of Reasons for Rejection for Japanese Patent Application No. 2014-561017, dated Mar. 21, 2017, 10 pages.

International Search Report and Written Opinion for PCT/US2013/029022, dated Jun. 26, 2013, 13 pages.

International Preliminary Report on Patentability for PCT/US2013/029022 dated Sep. 18, 2014, 9 pages.

International Search Report and Written Opinion for International Patent Application No. PCT/US2015/036082, dated Aug. 27, 2015, 15 pages.

International Preliminary Report on Patentability for International Patent Application No. PCT/US2015/036082, dated Dec. 29, 2016, 12 pages.

International Search Report and Written Opinion for International Patent Application No. PCT/US2015/061400, dated Mar. 29, 2016, 20 pages.

Invitation to Pay Additional Fees for International Patent Application No. PCT/US2016/067468, dated Feb. 13, 2017, 2 pages.

Conway, B. E., "Chapter 2: Similarities and Differences between Supercapacitors and Batteries for Storing Electrical Energy," Electrochemical Supercapacitors: Scientific Fundamentals and Technological Applications (book), 1999, New York, Springer Science + Business Media, pp. 11-12.

Conway, B. E., "Chapter 3: Energetics and Elements of the Kinetics of Electrode Processes," Electrochemical Supercapacitors: Scientific Fundamentals and Technological Applications (book), 1999, New York, Springer Science + Business Media, pp. 33-34.

Ozawa, Kazunori, "Lithium-Cell System—Nonaqueous Electrolyte System," Lithium Ion Rechargeable Batteries (book), Chapter 1: General Concepts, Section 1.1.2, 2009, WILEY-VCH Verlag GmbH & Co. KGaA, 5 pages.

Root, Michael, "Electric Vehicles," The TAB™ Battery Book: An In-Depth Guide to Construction, Design, and Use (book), Chapter 2: The Many Uses of Batteries, 2011, The McGraw-Hill Companies, 4 pages.

Kaewsongpol, Tanon et al., "High-performance supercapacitor of electrodeposited porous 3Dpolyaniline nanorods on functionalized carbon fiber paper: Effects of hydrophobic and hydrophilic surfaces of conductive carbon paper substrates," Materials Today Communications, vol. 4, Aug. 19, 2015, Elsevier Ltd., pp. 176-185.

Yan, Jun et al., "Preparation of graphene nanosheet/carbon nanotube/polyaniline composite as electrode material for supercapacitors," Journal of Power Sources, vol. 195, Issue 9, Nov. 11, 2009, Elsevier B.V., pp. 3041-3045.

Non-Final Office Action for U.S. Appl. No. 13/725,073, dated Aug. 28, 2017, 41 pages.

Fourth Office Action for Chinese Patent Application No. 201280070343. 4, dated Apr. 26, 2017, 22 pages.

Examination Report for European Patent Application No. 12874989. 2, dated Jul. 24, 2017, 5 pages.

Notice of Reason for Rejection for Japanese Patent Application No. 2014-548972, dated May 23, 2017, 4 pages.

(56) References Cited

OTHER PUBLICATIONS

Second Office Action for Chinese Patent Application No. 201380023699.7, dated Aug. 9, 2017, 8 pages.
Communication pursuant to Article 94(3) EPC for European Patent Application No. 13757195.6, dated Jul. 6, 2017, 3 pages.
International Preliminary Report on Patentability for International Patent Application No. PCT/US2015/061400, dated Jun. 1, 2017, 16 pages.
International Search Report and Written Opinion for International Patent Application No. PCT/US2016/067468, dated Apr. 21, 2017, 10 pages.
International Search Report and Written Opinion for International Patent Application No. PCT/US2017/014126, dated Apr. 20, 2017, 13 pages.
International Search Report and Written Opinion for International Patent Application No. PCT/US2017/024716, dated Jun. 20, 2017, 13 pages.
International Search Report and Written Opinion for International Patent Application No. PCT/US2017/023632, dated May 31, 2017, 11 pages.
International Search Report and Written Opinion for International Patent Application No. PCT/US2017/038992, dated Sep. 21, 2017, 12 pages.
Invitation to Pay Additional Fees for International Patent Application No. PCT/US2017/048883, dated Sep. 29, 2017, 2 pages.
International Search Report and Written Opinion for International Patent Application No. PCT/US2017/048883, dated Dec. 26, 2017, 10 pages.
Non-Final Office Action for U.S. Appl. No. 14/945,232, dated Jan. 29, 2018, 9 pages.
Extended European Search Report for European Patent Application No. 15809519.0, dated Feb. 5, 2018, 10 pages.
Decision on Rejection for Chinese Patent Application No. 201280070343.4, dated Jan. 5, 2018, 18 pages.
Non-Final Office Action for U.S. Appl. No. 15/612,405, dated Feb. 9, 2018, 9 pages.
Decision to Grant a Patent for Japanese Patent Application No. 2014-561017, dated Mar. 13, 2018, 4 pages.
Final Office Action for U.S. Appl. No. 13/725,073, dated Apr. 6, 2018, 37 pages.
Notice of Allowance for U.S. Appl. No. 15/612,405, dated May 16, 2018, 8 pages.
Third Office Action and Search Report for Chinese Patent Application No. 201380023699.7, dated Mar. 9, 2018, 16 pages.
Examination Report for European Patent Application No. 13757195.6, dated Jun. 13, 2018, 7 pages.
Non-Final Office Action for U.S. Appl. No. 15/319,286, dated Jun. 27, 2018, 9 pages.
Final Office Action for U.S. Appl. No. 14/945,232, dated Aug. 10, 2018, 7 pages.
Notification of the First Office Action for Chinese Patent Application No. 201580072540.3, dated Jun. 25, 2018, 14 pages.
Partial Supplementary European Search Report for European Patent Application No. 15861794.4, dated Jun. 28, 2018, 16 pages.
Non-Final Office Action for U.S. Appl. No. 15/382,871, dated Jun. 27, 2018, 11 pages.
International Preliminary Report on Patentability for International Patent Application No. PCT/US2016/067468, dated Jul. 5, 2018, 7 pages.
International Preliminary Report on Patentability for International Patent Application No. PCT/US2017/014126, dated Aug. 2, 2018, 10 pages.
Non-Final Office Action for U.S. Appl. No. 15/472,409, dated Jun. 29, 2018, 11 pages.
Decision on Rejection for Chinese Patent Application No. 201380023699.7, dated Aug. 16, 2018, 11 pages.
Braz, Elton P., et al., "Effects of Gamma Irradiation in Graphene/Poly(ethylene Oxide) Nanocomposites," 2013 International Nuclear Atlantic Conference—INAC 2013, Nov. 24-29, 2013, Recife, PE, Brazil, 7 pages.

Hu, Liangbing, et al., "Lithium-Ion Textile Batteries with Large Areal Mass Loading," Advanced Energy Materials, vol. 1, Issue 6, Oct. 6, 2011, pp. 1012-1017.
First Office Action for Canadian Patent Application No. 2,862,806, dated Nov. 22, 2018, 5 pages.
Non-Final Office Action for U.S. Appl. No. 16/029,930, dated Jan. 14, 2019, 8 pages.
Office Action for Canadian Patent Application No. 2,866,250, dated Jan. 11, 2019, 3 pages.
Acerce, Muharrem et al., "Metallic 1T phase $MoS_2$ nanosheets as supercapacitor electrode materials," Nature Nanotechnology, vol. 10, Mar. 23, 2015, Macmillan Publishers Limited, pp. 1-6.
Allen, Matthew J. et al., "Honeycomb Carbon: A Review of Graphene," Chemical Reviews, vol. 110, Issue 1, Jul. 17, 2009, American Chemical Society, pp. 132-145.
Augustyn, Veronica et al., "High-rate electrochemical energy storage through $Li^+$ intercalation pseudocapacitance," Nature Materials, vol. 12, Jun. 2013, www.nature.com/naturematerials, Macmillan Publishers Limited, pp. 518-522.
Author Unknown, "125 Volt Transportation Module," Maxwell Technologies, retrieved Apr. 13, 2016, website last modified Mar. 14, 2013, www.maxwell.com/products/ultracapacitors/125v-tranmodules, Maxwell Technologies, Inc., 2 pages.
Author Unknown, "ELTON: Super Capactiors," www.elton-cap.com/, Retrieved Apr. 15, 2016, ELTON, 1 page.
Author Unknown, "ELTON: Products and Technology," https://web.archive.org/web/20160306044847/http:/www.elton-cap.com/products/, dated Mar. 6, 2016, retrieved Mar. 15, 2017, ELTON, 2 pages.
Author Unknown, "Monthly battery sales statistics," Battery Association of Japan (BAJ), retrieved Apr. 13, 2016, website last modified Dec. 2010, web.archive.org/web/20110311224259/http://www.baj.or.jp/e/statistics/02.php, Battery Association of Japan, 1 page.
Author Unknown, "Turnigy Graphene Batteries," Batteries & Accessories, https://hobbyking.com/en_us/batteries-accessories/turnigy-graphene-2.html, retrieved Apr. 3, 2017, HobbyKing, 39 pages.
Arthur, Timothy, S. et al., "Three-dimensional electrodes and battery architectures," MRS Bulletin, vol. 36, Jul. 2011, Materials Research Society, pp. 523-531.
Bai, Ming-Hua et al., "Electrodeposition of vanadium oxide-polyaniline composite nanowire electrodes for high energy density supercapacitors," Journal of Materials Chemistry A, vol. 2, Issue 28, Jan. 29, 2014, The Royal Society of Chemistry, pp. 10882-10888.
Beidaghi, Majid, et al., "Capacitive energy storage in micro-scale devices: recent advances in design and fabrication of micro-supercapacitors," Energy and Environmental Science, vol. 7, Issue 3, Jan. 2, 2014, Royal Society of Chemistry, pp. 867-884.
Beidaghi, Majid et al., "Micro-Supercapacitors Based on Interdigital Electrodes of Reduced Graphene Oxide and Carbon Nanotube Composites with Ultra high Power Handling Performance," Advanced Functional Materials, vol. 22, Issue 21, Nov. 2, 2012, WILEY-VCH Verlag GmbH & Co. KGaA, Weinheim, pp. 4501-4510.
Beidaghi, Majid et al.,"Micro-supercapacitors based on three dimensional interdigital polypyrrole/C-MEMS electrodes," Electrochimica Acta, vol. 56, Issue 25, Oct. 30, 2011, Elsevier Ltd., pp. 9508-9514.
Bélanger, Daniel et al., "Manganese Oxides: Battery Materials Make the Leap to Electrochemical Capacitors," Electrochemical Society Interface, vol. 17, Issue 1, Spring 2008, The Electrochemical Society, pp. 49-52.
Bian, Li-Jun et al., "Self-doped polyaniline on functionalized carbon cloth as electroactive materials for supercapacitor," Electrochimica Acta, vol. 64, Dec. 29, 2011, Elsevier Ltd , pp. 17-22.
Bouville, Florian et al., "Strong, tough and stiff bioinspired ceramics from brittle constituents," Nature Materials, vol. 13, Issue 5, Mar. 23, 2014, Macmillan Publishers Limited, pp. 1-7.
Brain, Marshall et al., "How Batteries Work," Battery Arrangement and Power—HowStuffWorks, http://electronics.howstuffworks.com/everyday-tech/battery6.htm/printable, accessed Dec. 14, 2015, HowStuffWorks, 4 pages.
Brodie, B.C., "Ueber das Atomgewicht des Graphits," Justus Liebigs Annalen der Chemie, vol. 114, Issue 1, 1860, WILEY-VCH Verlag GmbH & Co. KGaA, Weinheim, pp. 6-24.

(56) References Cited

OTHER PUBLICATIONS

Burke, Andrew, "R&D considerations for the performance and application of electrochemical capacitors," Electrochimica Acta, vol. 53, Jan. 26, 2007, Elsevier Ltd., pp. 1083-1091.

Cao, Liujun et al., "Direct Laser-Patterned Micro-Supercapacitors from Paintable $MoS_2$ Films," Small, vol. 9, Issue 17, Apr. 16, 2013, WILEY-VCH Verlag GmbH & Co. KGaA, Weinheim, pp. 2905-2910.

Chan, Candace K. et al., "High-performance lithium battery anodes using silicon nanowires," Nature Nanotechnology, vol. 3, Issue 1, Jan. 2008, Nature Publishing Group, pp. 31-35.

Chen, Cheng-Meng et al., "Macroporous 'bubble' graphene film via template-directed ordered-assembly for high rate supercapacitors," Chemical Communications, vol. 48, Issue 57, May 15, 2012, The Royal Society of Chemistry, pp. 1-3.

Chen, Ji et al., "High-yield preparation of graphene oxide from small graphite flakes via an improved Hummers method with a simple purification process," Carbon, vol. 81, Jan. 2015, Elsevier Ltd., pp. 1-9.

Chen, L. Y. et al., "Toward the Theoretical Capacitance of $RuO_2$ Reinforced by Highly Conductive Nanoporous Gold," Advanced Energy Materials, vol. 3, Issue 7, Jul. 2014, WILEY-VCH Verlag GmbH & Co. KGaA, Weinheim, pp. 851-856.

Chen, Wei et al., "High-Performance Nanostructured Supercapacitors on a Sponge," Nano Letters, vol. 11, Issue 12, Sep. 16, 2011, American Chemical Society, 22 pages.

Chen, Zongping et al, "Three-dimensional flexible and conductive interconnected graphene networks grown by chemical vapour deposition," Nature Materials, vol. 10, Issue 6, Jun. 2011, Macmillan Publishers Limited, pp. 424-428.

Cheng, Yingwen et al., "Synergistic Effects from Graphene and Carbon Nanotubes EnableFlexible and Robust Electrodes for High-PerformanceSupercapacitors," Nano Letters, vol. 12, Issue 8, Jul. 23, 2012, American Chemical Society, pp. 4206-4211.

Chi, Kai et al., "Freestanding Graphene Paper Supported Three-Dimensional Porous Graphene-Polyaniline Nanocomposite Synthesized by Inkjet Printing and in Flexible All-Solid-State Supercapacitor," ACS Applied Materials & Interfaces, vol. 6, Issue 18, Sep. 10, 2014, American Chemical Society, 8 pages.

Chmiola, John et al., "Monolithic Carbide-Derived Carbon Films for Micro-Supercapacitors," Science, vol. 328, Issue 5977, Apr. 2010, American Association for the Advancement of Science, 4 pages.

Choi, Bong Gill et al., "3D Macroporous Graphene Frameworks for Supercapacitors with High Energy and Power Densities," ACS Nano, vol. 6, Issue 5, Apr. 23, 2012, American Chemical Society, pp. 4020-4028.

Cooper, A. et al., "The UltraBattery—A new battery design for a new beginning in hybrid electric vehicle energy storage," Journal of Power Sources, vol. 188, Issue 2, Dec. 6, 2008, Elsevier B.V. pp. 642-649.

Deville, Sylvain, "Freeze-Casting of Porous Ceramics: A Review of Current Achievements and Issues," Advanced Engineering Materials, vol. 10, Issue 3, Mar. 20, 2008, WILEY-VCH Verlag GmbH & Co., pp. 155-169.

Deville, Sylvain, "Metastable and unstable cellular solidification of colloidal suspensions," Nature Materials, vol. 8, Dec. 2009, Macmillan Publishers Limited, pp. 966-972.

De Volder, Michaël et al., "Corrugated Carbon Nanotube Microstructures with Geometrically Tunable Compliance," ACS NANO, vol. 5, Issue 9, Aug. 1, 2011, pp. 7310-7317.

Dunn, Bruce et al., "Electrical Energy Storage for the Grid: A Battery of Choices," Science, vol. 334, Issue 928, Nov. 18, 2011, American Association for the Advancement of Science, pp. 928-935.

Eda, Goki et al., "Chemically Derived Graphene Oxide: Towards Large-Area Thin-Film Electronics and Optoelectronics," Advanced Materials, vol. 22, Issue 22, Apr. 28, 2010, WILEY-VCH Verlag GmbH & Co., pp. 2392-2415.

El-Kady, Maher F. et al., "Engineering Three-Dimensional Hybrid Supercapacitors and Micro-Supercapacitors for High-Performance Integrated Energy Storage," Proceedings of the National Academy of Sciences of the United States of America, vol. 112, Issue 14, Apr. 7, 2015, National Academy of Sciences, pp. 4233-4238.

El-Kady, Maher F. et al., "Laser Scribing of High-Performance and Flexible Graphene-Based Electrochemical Capacitors," Science Magazine, Mar. 16, 2012, vol. 335, No. 6074, 6 pages.

El-Kady, Maher F. et al., "Laser Scribing of High-Performance and Flexibile Graphene-Based Electrochemical Capacitors," Science, vol. 335, Issue 6074, Mar. 16, 2012, www.sciencemag.org/cgi/content/full/335/6074/1326/DC1, American Association for the Advancement of Science, 25 pages.

El-Kady, Maher F. et al., "Scalable Fabrication of High-Power Graphene Micro-Supercapacitors for Flexible and On-Chip Energy Storage," Nature Communications, vol. 4, Issue 1475, Feb. 12, 2013, Macmillan Publishers Limited, pp. 1-9.

El-Kady, Maher F. et al., "Supplementary Information: Scalable Fabrication of High-Power Graphene Micro-Supercapacitors for Flexible and On-Chip Energy Storage", Nature Communications, Submitted for Publication: Oct. 1, 2012, 23 pages.

Fan, Zhuangjun et al., "Asymmetric Supercapacitors Based on Graphene/$MnO_2$ and Activated Carbon Nanofiber Electrodes with High Power and Energy Density," Advanced Functional Materials, vol. 21, Issue 12, Jun. 21, 2011, WILEY-VCH Verlag GmbH & Co. KGaA, Weinheim, pp. 2366-2375.

Feng, Jun et al., "Metallic Few-Layered $VS_2$ Ultrathin Nanosheets: High Two-Dimensional Conductivity for In-Plane Supercapacitors," Journal of the American Chemical Society, vol. 133, Issue 44, Sep. 27, 2011, American Chemical Society, pp. 17832-17838.

Fischer, Anne E. et al., "Incorporation of Homogeneous, Nanoscale $MnO_2$ within Ultraporous Carbon Structures via Self-Limiting Electroless Deposition: Implications for Electrochemical Capacitors," Nano Letters, vol. 7, Issue 2, Jan. 13, 2007, American Chemical Society, pp. 281-286.

Foo, Ce Yao et al., "Flexible and Highly Scalable $V_2O_5$-rGO Electrodes in an Organic Electrolyte for Supercapacitor Devices," Advanced Energy Materials, vol. 4, Issue 12, Aug. 26, 2014, WILEY-VCH Verlag GmbH & Co. KGaA, Weinheim, pp. 1-7.

Gan, Shiyu et al., "Spontaneous and Fast Growth of Large-Area Graphene Nanofilms Facilitated by Oil/Water Interfaces," Advanced Materials, vol. 24, Issue 29, Jun. 12, 2012, WILEY-VCH Verlag GmbH & Co, pp. 3958-3964.

Gao, Wei et al., "Direct laser writing of micro-supercapacitors on hydrated graphite oxide films," Nature Nanotechnology, vol. 6, Issue 8, Jul. 2011, Macmillan Publishers Limited, p. 496-500.

Gao, Wei et al., "Direct laser writing of micro-supercapacitors on hydrated graphite oxide films," Supplementary Information, Nature Nanotechnology, vol. 6, Issue 8, Jul. 2011, Macmillan Publishers Limited, 15 pages.

Gao, Hongcai et al., "Flexible All-Solid-State Asymmetric Supercapacitors Based on Free-Standing Carbon Nanotube/Graphene and $Mn_3O_4$ Nanoparticle/Graphene Paper Electrodes," Applied Materials & Interfaces, vol. 4, Issue 12, Nov. 20, 2012, American Chemical Society, pp. 7020-7026.

Gao, Hongcai et al., "High-Performance Asymmetric Supercapacitor Based on Graphene Hydrogel and Nanostructured $MnO_2$," ACS Applied Materials and Interfaces, vol. 4, Issue 5, Apr. 30, 2012, American Chemical Society, pp. 2801-2810.

Notice of Acceptance for Australian Patent Application No. 2015277264, dated Jul. 31, 2019, 3 pages.

Cannarella et al., "Mechanical Properties of a Battery Separator under Compression and Tension," Journal of the Electrochemical Society, vol. 161, No. 11, Sep. 26, 2014, pagesp. F3117-F3122.

Fernandez-Merino, M.J. et al., "Vitamin C Is an Ideal Substitute for Hydrazine in the Reduction of Graphene Oxide Suspensions," The Journal of Physical Chemistry C, vol. 114, No. 14, Mar. 4, 2010, American Chemical Society, pp. 6426-6432.

Gao, C. et al., "Superior Cycling Performance of SiOx/C Composite with Arrayed Mesoporous Architecture as Anode Material for Lithium-Ion Batteries," Journal of The Electrochemical Society, vol. 161, No. 14, 2014, The Electrochemical Society, pp. A2216-A2221.

(56) References Cited

OTHER PUBLICATIONS

Lu, J. et al., "Advanced applications of ionic liquids in polymer science," Progress in Polymer Science, vol. 34, 2009, Elsevier Ltd., pp. 431-448.
Vranes, M. et al., "Physicochemical Characterization of 1-Butyl-3-methylimidazolium and 1-Butyl-1-methylpyrrolidinium Bis{trifluoromethylsulfonyl}imide," Journal of Chemical & Engineering Data, vol. 57, Mar. 7, 2012, American Chemical Society, pp. 1072-1077.
Yan, Jun et al., "High-performance supercapacitor electrodes based on highly corrugated graphene sheets," Carbon, vol. 50, 2012, Elsevier Ltd., pp. 2179-2188.
Non-Final Office Action for U.S. Appl. No. 15/427,210, dated Sep. 3, 2019, 16 pages.
Notice of Allowance for U.S. Appl. No. 15/427,210, dated Dec. 18, 2019, 9 pages.
Office Action for Canadian Patent Application No. 2,862,806, dated Sep. 30, 2019, 3 pages.
Grant of Patent for Korean Patent Application No. 10-2014-7020353, dated Oct. 29, 2019, 3 pages.
Final Office Action for U.S. Appl. No. 15/612,405, dated Dec. 27, 2019, 17 pages.
Final Office Action for U.S. Appl. No. 16/029,930, dated Nov. 15, 2019, 16 pages.
Office Action for Canadian Patent Application No. 2,866,250, dated Dec. 17, 2019, 3 pages.
Examination Report for European Patent Application No. 13757195.6, dated Jan. 29, 2020, 4 pages.
Notice of Preliminary Rejection for Korean Patent Application No. 10-2014-7028084, dated Aug. 22, 2019, 30 pages.
Office Action for Brazilian Patent Application No. 112016029468, dated Jan. 21, 2020, 6 pages.
Third Office Action for Chinese Patent Application No. 201580043429.1, dated Jan. 3, 2020, 20 pages.
Examination Report for European Patent Application No. 15809519.0, dated Dec. 9, 2019, 7 pages.
Office Action for Israeli Patent Application No. 249506, dated Dec. 3, 2019, 8 pages.
Decision of Rejection for Japanese Patent Application No. 2016-573846, dated Oct. 29, 2019, 9 pages.
Non-Final Office Action for U.S. Appl. No. 14/945,232, dated Sep. 3, 2019, 8 pages.
Notice of Allowance for U.S. Appl. No. 14/945,232, dated Dec. 20, 2019, 9 pages.
Supplemental Notice of Allowability for U.S. Appl. No. 14/945,232, dated Feb. 12, 2020, 5 pages.
Office Action for Brazilian Patent Application No. 112017010257, dated Jan. 28, 2020, 7 pages.
Official Action for Eurasian Patent Application No. 201791078, dated Nov. 6, 2019, 4 pages.
Notification of Reasons for Rejection for Japanese Patent Application No. 2017-526533, dated Aug. 20, 2019, 4 pages.
Non-Final Office Action for U.S. Appl. No. 15/382,871, dated Sep. 16, 2019, 9 pages.
Applicant-Initiated Interview Summary for U.S. Appl. No. 15/382,871, dated Dec. 31, 2019, 5 pages.
Non-Final Office Action for U.S. Appl. No. 16/428,409, dated Sep. 16, 2019, 12 pages.
First Office Action for Chinese Patent Application No. 2016800753323, dated Aug. 27, 2019, 15 pages.
Notice of Allowance and Examiner-Initiated Interview Summary for U.S. Appl. No. 15/410,404, dated Oct. 25, 2019, 11 pages.
Corrected Notice of Allowability for U.S. Appl. No. 15/410,404, dated Dec. 3, 2019, 6 pages.
International Preliminary Report on Patentability for International Patent Application No. PCT/US2018/041728, dated Jan. 23, 2020, 7 pages.
First Office Action for Chinese Patent Application No. 2017800076125, dated Nov. 28, 2019, 20 pages.

Extended European Search Report for European Patent Application No. 17741923.1, dated Nov. 15, 2019, 18 pages.
Notice of Allowance for U.S. Appl. No. 15/472,409, dated Dec. 11, 2019, 11 pages.
Official Action for Eurasian Patent Application No. 201892199, dated Nov. 28, 2019, 6 pages.
Extended European Search Report for European Patent Application No. 17776536.9, dated Oct. 30, 2019, 8 pages.
Final Office Action for U.S. Appl. No. 15/688,342, dated Oct. 17, 2019, 11 pages.
Non-Final Office Action for U.S. Appl. No. 15/630,758, dated Oct. 11, 2019, 11 pages.
Extended European Search Report for European Paetnt Application No. 17816292.1, dated Jan. 7, 2020, 9 pages.
Examination Report for Indian Patent Application No. 201817044642, dated Nov. 26, 2019, 7 pages.
Applicant-Initiated Interview Summary for U.S. Appl. No. 15/466,425, dated Oct. 22, 2019, 3 pages.
Final Office Action for U.S. Appl. No. 15/466,425, dated Jan. 28, 2020, 8 pages.
Official Action for Eurasian Patent Application No. 201892118, dated Nov. 28, 2019, 4 pages.
Extended European Search Report for European Patent Application No. 17771081.1, dated Oct. 22, 2019, 6 pages.
Notice of Reexamination for Chinese Patent Application No. 201280070343.4, dated Feb. 3, 2020, 7 pages.
Notice of Preliminary Rejection for Korean Patent Application No. 10-2014-7028084, dated Feb. 17, 2020, 5 pages.
Examination Report for Indian Patent Application No. 201617042976, dated Mar. 13, 2020, 7 pages.
Advisory Action for U.S. Appl. No. 15/612,405, dated Jun. 24, 2020, 3 pages.
Non-Final Office Action for U.S. Appl. No. 16/029,930, dated Jun. 24, 2020, 16 pages.
Final Office Action for U.S. Appl. No. 16/428,409, dated Jun. 24, 2020, 16 pages.
Zhang, Luojiang, et al., "3D porous layered double hydroxides grown on graphene as advanced electrochemical pseudocapacitor materials," Journal of Materials Chemistry A, vol. 1, 2013, pp. 9046-9053.
Notice of Acceptance for Australian Patent Application No. 2019250120, dated Nov. 11, 2020, 3 pages.
Notification of Decision of Rejection for Japanese Patent Application No. 2017-526533, dated Nov. 17, 2020, 6 pages.
Official Notification for Eurasion Patent Application No. 20182199, dated Dec. 11, 2020, 6 pages.
Notification of the Second Office Action for Chinese Patent Application No. 2017800249783, dated Dec. 2, 2020, 9 pages.
Official Action for Eurasion Patent Application No. 201892118, dated Dec. 11, 2020, 6 pages.
Invitation to Pay Additional Fees and Partial Search for International Patent Application No. PCT/US2020/052618, dated Nov. 30, 2020, 2 pages.
Non-Final Office Action for U.S. Appl. No. 16/791,517, dated Apr. 1, 2021, 16 pages.
Applicant-Initiated Interview Summary for U.S. Appl. No. 16/428,409, dated Mar. 19, 2021, 2 pages.
Applicant-Initiated Interview Summary for U.S. Appl. No. 16/033,266, dated Apr. 8, 2021, 3 pages.
Notification of Reasons for Rejection for Japanese Patent Application No. 2018-538110, dated Jan. 20, 2021, 9 pages.
Notification of Reasons for Rejection for Japanese Patent Application No. 2018-550836, dated Feb. 12, 2021, 6 pages.
Examination Report for Taiwanese Patent Application No. 106121056, dated Feb. 3, 2021, 10 pages.
Notice of Preliminary Rejection for Korean Patent Application No. 10-2018-7030385, dated Mar. 13, 2021, 10 pages.
Notice of Reasons for Rejection for Japanese Patent Application No. 2018-549538, dated Feb. 15, 2021, 6 pages.
Partial Supplementary European Search Report for European Patent Application No. 18832324.0, dated Mar. 12, 2021, 15 pages.
Second Office Action for Chinese Patent Application No. 201811438766.2, dated Oct. 28, 2020, 10 pages.

(56) References Cited

OTHER PUBLICATIONS

Notification of Reexamination for Chinese Patent Application No. 2015800725403, dated Oct. 12, 2020, 9 pages.
Office Action for Israeli Patent Application No. 252320, dated Sep. 17, 2020, 11 pages.
Examination Report for Australian Patent Application No. 2016378400, dated Sep. 22, 2020, 5 pages.
Examination Report for Taiwanese Patent Application No. 105142233, dated Sep. 25, 2020, 19 pages.
Examination Report for Australian Patent Application No. 2017209117, dated Oct. 5, 2020, 5 pages.
Examination Report for Taiwanese Patent Application No. 106109733, dated Oct. 20, 2020, 11 pages.
Notice of Allowance for U.S. Appl. No. 15/612,405, dated Dec. 17, 2020, 8 pages.
Non-Final Office Action for U.S. Appl. No. 16/029,930, dated Jan. 6, 2021, 15 pages.
Final Office Action for U.S. Appl. No. 16/033,266, dated Jan. 6, 2021, 10 pages.
Notice of Allowance for U.S. Appl. No. 15/466,425, dated Mar. 10, 2021, 9 pages.
Final Office Action for U.S. Appl. No. 16/004,818, dated Feb. 25, 2021, 24 pages.
Yang, Wanlu, et al., "Solvothermal One-Step Synthesis of Ni—Al Layered Double Hydroxide/Carbon Nanotube/Reduced Graphene Oxide Sheet Ternary Nanocomposite with Ultrahigh Capacitance for Supercapacitors," Applied Materials and Interfaces, vol. 5, 2013, American Chemical Society, pp. 5443-5454.
Decision of Reexamination for Chinese Patent Application No. 201580072540.3, dated Feb. 2, 2021, 18 pages.
Notification of Reasons for Rejection for Japanese Patent Application No. 2018-532233, dated Dec. 15, 2020, 8 pages.
Examination Report for Australian Patent Application No. 185870, dated Jan. 28, 2021, 5 pages.
Official Notification for Eurasian Patent Application No. 201990068, dated Jan. 14, 2021, 6 pages.
Notice of Preliminary Rejection for Korean Patent Application No. 10-2018-7029515, dated Jan. 21, 2021, 9 pages.
International Search Report and Written Opinion for International Patent Application No. PCT/US2020/052618, dated Feb. 17, 2021, 19 pages.
Chen, DA, et al., "Graphene-based materials in electrochemistry," Chemical Society Reviews, vol. 39, Issue 8, Jun. 2010, 24 pages.
Paik, Pradip, et al., "Polyaniline nanotubes with rectangular-hollow-core- and its self-assembled surface decoration: high conductivity and dielectric properties," RSC Advances, vol. 4, Issue 24, 2014, pp. 12342-12352.
Summons to Attend Oral Proceedings for European Patent No. 13757195.6, mailed Oct. 13, 2021, 6 pages.
Examination Report for European Patent Application No. 15809519.0, dated Oct. 12, 2021, 5 pages.
Examination Report for Australian Patent Application No. 2968139, dated Oct. 6, 2021, 5 pages.
Office Action for Vietnamese Patent Application No. 1-2017-01911, dated Oct. 7, 2021, 3 pages.
Notification of Reasons for Rejection for Japanese Patent Application No. 2018-532233, dated Oct. 26, 2021, 6 pages.
Examination Report for European Patent Application No. 17741923.1, dated Oct. 22, 2021, 5 pages.
Examination Report for Australian Patent Application No. 2017245151, dated Nov. 2, 2021, 5 pages.
Office Action for Israeli Patent Application No. 261928, dated Oct. 12, 2021, 6 pages.
First Office Action for Chinese Patent Application No. 201780063416.X, dated Sep. 1, 2021, 14 pages.
Notice of Acceptance for Australian Patent Application No. 2017281543, dated Nov. 9, 2021, 3 pages.
Office Action for Israeli Patent Application No. 263442, dated Sep. 30, 2021, 8 pages.
Office Action for Korean Patent Application No. 10-2019-7001932, dated Oct. 25, 2021, 5 pages.
Office Action for Israeli Patent Application No. 261620, dated Aug. 31, 2021, 6 pages.
Lin, Jian, et al., "Laser-induced porous graphene films from commercial polymers," Nature Communications, Dec. 2014, 8 pages.
Notice of Reasons for Refusal for Japanese Patent Application No. 2020-034093, dated Jun. 1, 2021, 10 pages.
Ntention to Grant for European Patent Application No. 16879927.8, dated Jun. 9, 2021, 5 pages.
Official Notification for Eurasion Patent No. 20182199, dated Jun. 4, 2021, 12 pages.
Ntention to Grant for European Patent Application No. 17776536.9, dated Jul. 2, 2021, 7 pages.
Request for additional materials for Eurasian Patent Application No. 201990587, dated May 21, 2021, 6 pages.
Written Opinion for Brazilian Patent Application No. 112018076559, dated Jun. 8, 2021, 6 pages.
Notification of the Third Office Action for Chinese Patent Application No. 2017800249783, dated May 21, 2021, 8 pages.
Official Notification for Eurasian Patent Application No. 201892118, dated Jun. 18, 2021, 8 pages.
Examination Report for European Patent Application No. 17771081.1, dated Jun. 17, 2021, 4 pages.
Extended European Search Report for European Patent Application No. 18832324.0, dated Jun. 24, 2021, 15 pages.
Office Action for Canadian Patent Application No. 2,952,233, dated Jun. 29, 2021, 4 pages.
Office Action for Eurasian Patent Application No. 201790003, dated May 20, 2021, 7 pages.
Written Opinion for Brazilian Patent Application No. 112019004128, dated Jun. 25, 2021, 6 pages.
Notice of Acceptance for Australian Patent Application No. 2016378400, dated Jul. 30, 2021, 3 pages.
Applicant-Initiated Interview Summary for U.S. Appl. No. 16/791,517, dated Aug. 27, 2021, 2 pages.
Non-Final Office Action for U.S. Appl. No. 16/0004,818, dated Sep. 17, 2021, 20 pages.
Examination Report for European Patent Application No. 15861794.4, dated Apr. 14, 2021, 4 pages.
Examination Report for Australian Patent Application No. 2017245151, dated Mar. 25, 2021, 5 pages.
Second Office Action for Chinese Patent Application No. 2017800273161, dated Apr. 6, 2021, 8 pages.
Notification of Reasons for Rejection for Japanese Patent Application No. 2018-567030, dated Apr. 5, 2021, 8 pages.
Examination Report for Australian Patent Application No. 2017238201, dated Mar. 17, 2021, 4 pages.
Notice of Allowance for U.S. Appl. No. 16/029,930, dated Oct. 20, 2021, 7 pages.
Final Office Action for U.S. Appl. No. 16/791,517, dated Oct. 18, 2021, 11 pages.
An, et al., "Fabrication of graphene/polypyrrole nanotube/MnO2 nanotube composite and its supercapacitor application," European Physical Journal, Applied Physics, vol. 58, 2012, 9 pages.
Gu, et al., "Synthesis of polyaniline nanotubes with controlled rectangular or square pore shape," Materials Letters, vol. 121, 2014, pp. 12-14.
Liu, Jianhua, et al., "Synthesis of a Graphene-Polypyrrole Nanotube Composite and Its Application in Supercapaciton Electrode," Journal of The Electrochemical Society, vol. 159, Issue 6, Apr. 2012, 6 pages.
Wang, et al., "Polyaniline nanotube arrays as high-performance flexible electrodes for electrochemical energy storage devices," Journal of Materials Chemistry, vol. 22, 2012, pp. 2401-2404.
Non-Final Office Action for U.S. Appl. No. 16/751,314, dated Jul. 13, 2021, 13 pages.
Notice of Allowance for U.S. Appl. No. 16/033,266, dated Jun. 3, 2021, 9 pages.
Corrected Notice of Allowability for U.S. Appl. No. 16/033,266, dated Jun. 4, 2021, 7 pages.
Office Action for Eurasion Patent Application No. 201990068, dated Aug. 30, 2021, 7 pages.

(56) References Cited

OTHER PUBLICATIONS

Notice of Preliminary Rejection for Korean Patent Application No. 10-2017-7000924, dated Aug. 25, 2021, 11 pages.
Office Action for Israeli Patent Application No. 260398, dated Jul. 20, 2021, 7 pages.
Examination Report for Australian Patent Application No. 2017321294, dated Aug. 24, 2021, 2 pages.
Notification of Reasons for Rejection for Japanese Patent Application No. 2019511650, dated Aug. 19, 2021, 13 pages.
Examination Report for Australian Patent Application No. 185870, dated Aug. 20, 2021, 2 pages.
Examination Report for Indian Patent Application No. 202017002602, dated Sep. 9, 2021, 6 pages.
Shao, et al., "3D Freeze-Casting of Cellular Graphene Films for Ultrahigh-Power-Density Supercapacitors," Advanced Materials, vol. 28, 2016, 8 pages.
Notice of Allowance for U.S. Appl. No. 16/428,409, dated May 14, 2021, 10 pages.
Notice of Allowance for U.S. Appl. No. 15/630,758, dated May 14, 2021, 11 pages.
Notice of Acceptance for Australian Patent Application No. 2017209117, dated Oct. 6, 2021, 3 pages.
Notification of Decision of Rejection for Japanese Patent Application No. 2018-550836, dated Sep. 10, 2021, 6 pages.
Examination Report for Taiwanese Patent Application No. 106129539, dated Sep. 3, 2021, 10 pages.
Notice of Preliminary Rejection for Korean Patent Application No. 10-2017-7015753, dated Nov. 17, 2021, 9 pages.
Notification of Reasons for Rejection for Japanese Patent Application No. 2018-538110, dated Oct. 29, 2021, 12 pages.
Third Office Action for Chinese Patent Application No. 2017800273161, dated Nov. 2, 2021, 17 pages.
Notice of Acceptance for Australian Patent Application No. 2017321294, dated Nov. 30, 2021, 3 pages.
Office Action for Eurasian Patent Application No. 201990587, dated Dec. 10, 2021, 4 pages.
First Office Action for Chinese Patent Application No. 2017800441862, dated Dec. 10, 2021, 17 pages.
Hearing Notice for Indian Patent Application No. 201817044642, dated Jan. 18, 2022, 2 pages.
Grant of Patent for Korean Patent Application No. 10-2018-7029515, dated Nov. 25, 2021, 4 pages.
Office Action for Canadian Patent Application No. 2952233, dated Jan. 6, 2022, 4 pages.
Hearing Notice for Indian Patent Application No. 201817044642, dated Dec. 27, 2021, 2 pages.
First Office Action for Chinese Patent Application No. 2018800459108, dated Oct. 29, 2021, 18 pages.
Office Action for Eurasian Patent Application No. 201790003, dated Dec. 9, 2021, 5 pages.
Decision to Grant for Japanese Patent Application No. 2020-034093, dated Feb. 8, 2022, 5 pages.
Notice of Allowance for Korean Patent Application No. 10-2018-7030385, dated Jan. 27, 2022, 5 pages.
Examination Report for European Patent Application No. 17847303.9, dated Jan. 26, 2022, 6 pages.
Hearing Notice for Indian Patent Application No. 201817044642, dated Feb. 18, 2022, 2 pages.
Notice of Acceptance for Australian Patent Application No. 2017238201, dated Jan. 14, 2022, 3 pages.
Final Office Action for U.S. Appl. No. 16/004,818, dated Feb. 2, 2022, 21 pages.
Patil, Dipali, et al., "Investigations on silver/polyaniline electrodes for electrochemical supercapacitors," Physical Chemistry Chemical Physics, vol. 14, 2012, pp. 11886-11895.
Shao, et al., "Fabrication of polyaniline nanowire/TiO2 nanotube array electrode for supercapacitors," Energy, vol. 87, 2015, Elsevier Ltd., pp. 578-585.
Final Office Action for U.S. Appl. No. 16/751,314, dated Jan. 19, 2022, 19 pages.
Advisory Action for U.S. Appl. No. 16/791,517, dated Mar. 23, 2022, 3 pages.
Decision to Grant for European Patent Application No. 16879927.8, dated Mar. 24, 2022, 2 pages.
Examination Report for Taiwanese Patent Application No. 106102134, dated Jan. 26, 2022, 44 pages.
Notice of Acceptance for Australian Patent Application No. 2017245151, dated Mar. 4, 2022, 3 pages.
Notification of Reasons for Rejection for Japanese Patent Application No. 2018-567030, dated Feb. 24, 2022, 4 pages.
Decision of Rejection for Chinese Patent Application No. 2017800249783, dated Jan. 18, 2022, 7 pages.
Examination Report for European Patent Application No. 15809519.0, dated May 17, 2022, 6 pages.
Non-Final Office Action for U.S. Appl. No. 16/791,517, dated Apr. 27, 2022, 12 pages.
Office Action for Brazilian Patent Application No. 112017010257, dated Apr. 12, 2022, 7 pages.
Notice of Allowance for Israeli Patent Application No. 259749, dated Apr. 28, 2022, 3 pages.
Notification to Grant for Chinese Patent Application No. 201780027316.1, dated Apr. 15, 2022, 4 pages.
Notice of Reasons for Refusal for Japanese Patent Application No. 2019511650, dated Mar. 28, 2022, 5 pages.
Examination Report for Taiwanese Patent Application No. 106129539, dated Mar. 9, 2022, 4 pages.
Grant of Patent for Korean Patent Application No. 10-2019-7001932, dated Apr. 18, 2022, 5 pages.
Examination Report for Indian Patent Application No. 201917053095, dated Mar. 28, 2022, 5 pages.
Notification of Reasons for Rejection for Japanese Patent Application No. 2021-041173, dated Mar. 11, 2022, 6 pages.
Notification of Reasons for Rejection for Japanese Patent Application No. 2018-532233, dated Apr. 1, 2022, 6 pages.

* cited by examiner

INTERCONNECTED CORRUGATED CARBON-BASED NETWORK

CROSS-REFERENCE

This application is a continuation of U.S. patent application Ser. No. 15/427,210, filed Feb. 8, 2017, now U.S. Pat. No. 10,648,958, which is a divisional application of U.S. application Ser. No. 13/725,073, filed Dec. 21, 2012, which claims the benefit of U.S. Provisional Application Ser. No. 61/578,431, filed Dec. 21, 2011, each of which is incorporated herein by reference in its entirety, and to which applications we claim priority under 35 USC § 121.

STATEMENT AS TO FEDERALLY SPONSORED RESEARCH

This invention was made with government support under Grant Number HR0011-10-3-0002, awarded by the U.S. Department of Defense, Defense Advanced Research Projects Agency, Microsystems Technology Office. The government has certain rights in the invention.

BACKGROUND OF THE INVENTION

The present disclosure provides an interconnected corrugated carbon-based network and an inexpensive process for making, patterning, and tuning the electrical, physical and electrochemical properties of the interconnected corrugated carbon-based network.

In the pursuit of producing high quality bulk carbon-based devices such as organic sensors, a variety of syntheses now incorporate graphite oxide (GO) as a precursor for the generation of large scale carbon-based materials. Inexpensive methods for producing large quantities of GO from the oxidation of graphitic powders are now available. In addition, the water dispersibility of GO combined with inexpensive production methods make GO an ideal starting material for producing carbon-based devices. In particular, GO has water dispersible properties. Unfortunately, the same oxygen species that give GO its water dispersible properties also create defects in its electronic structure, and as a result, GO is an electrically insulating material. Therefore, the development of device grade carbon-based films with superior electronic properties requires the removal of these oxygen species, re-establishment of a conjugated carbon network, as well as a method for controllably patterning carbon-based device features.

Methods for reducing graphite oxide have included chemical reduction via hydrazine, hydrazine derivatives, or other reducing agents, high temperature annealing under chemical reducing gases and/or inert atmospheres, solvothermal reduction, a combination of chemical and thermal reduction methods, flash reduction, and most recently, laser reduction of GO. Although several of these methods have demonstrated relatively high quality graphite oxide reduction, many have been limited by expensive equipment, high annealing temperatures and nitrogen impurities in the final product. As a result, of these difficulties, a combination of properties that includes high surface area and high electrical conductivity in an expanded interconnected carbon network has remained elusive. In addition, large scale film patterning via an all-encompassing step for both GO reduction and patterning has proven difficult and has typically been dependent on photo-masks to provide the most basic of patterns. Therefore, what is needed is an inexpensive process for making and patterning an interconnected corrugated carbon-based network having a high surface area with highly tunable electrical conductivity and electrochemical properties.

SUMMARY OF THE INVENTION

The present disclosure provides a method of producing an interconnected corrugated carbon-based network. The interconnected corrugated carbon-based network produced has a combination of properties that includes high surface area and high electrical conductivity in an expanded network of interconnected carbon layers.

In one embodiment, the method produces a patterned interconnected corrugated carbon-based network. In that particular embodiment, an initial step receives a substrate having a carbon-based oxide film. Once the substrate is received, a next step involves generating a light beam having a power density sufficient to reduce portions of the carbon-based oxide film to an interconnected corrugated carbon-based network. Another step involves directing the light beam across the carbon-based oxide film in a predetermined pattern via a computerized control system while adjusting the power density of the light beam via the computerized control system according to predetermined power density data associated with the predetermined pattern.

In one embodiment, the substrate is a disc-shaped, digital versatile disc (DVD) sized thin plastic sheet removably adhered to a DVD sized plate that includes a DVD centering hole. The DVD sized plate carrying the disc-shaped substrate is loadable into a direct-to-disc labeling enabled optical disc drive. A software program executed by the computerized control system reads data that defines the predetermined pattern. The computerized control system directs a laser beam generated by the optical disc drive onto the disc-shaped substrate, thereby reducing portions of the carbon-based oxide film to an electrically conductive interconnected corrugated carbon-based network that matches shapes, dimensions, and conductance levels dictated by the data of the predetermined pattern.

Those skilled in the art will appreciate the scope of the disclosure and realize additional aspects thereof after reading the following detailed description in association with the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The accompanying drawings incorporated in and forming a part of this specification illustrate several aspects of the disclosure, and together with the description serve to explain the principles of the disclosure.

DETAILED DESCRIPTION OF THE INVENTION

Figure 1:
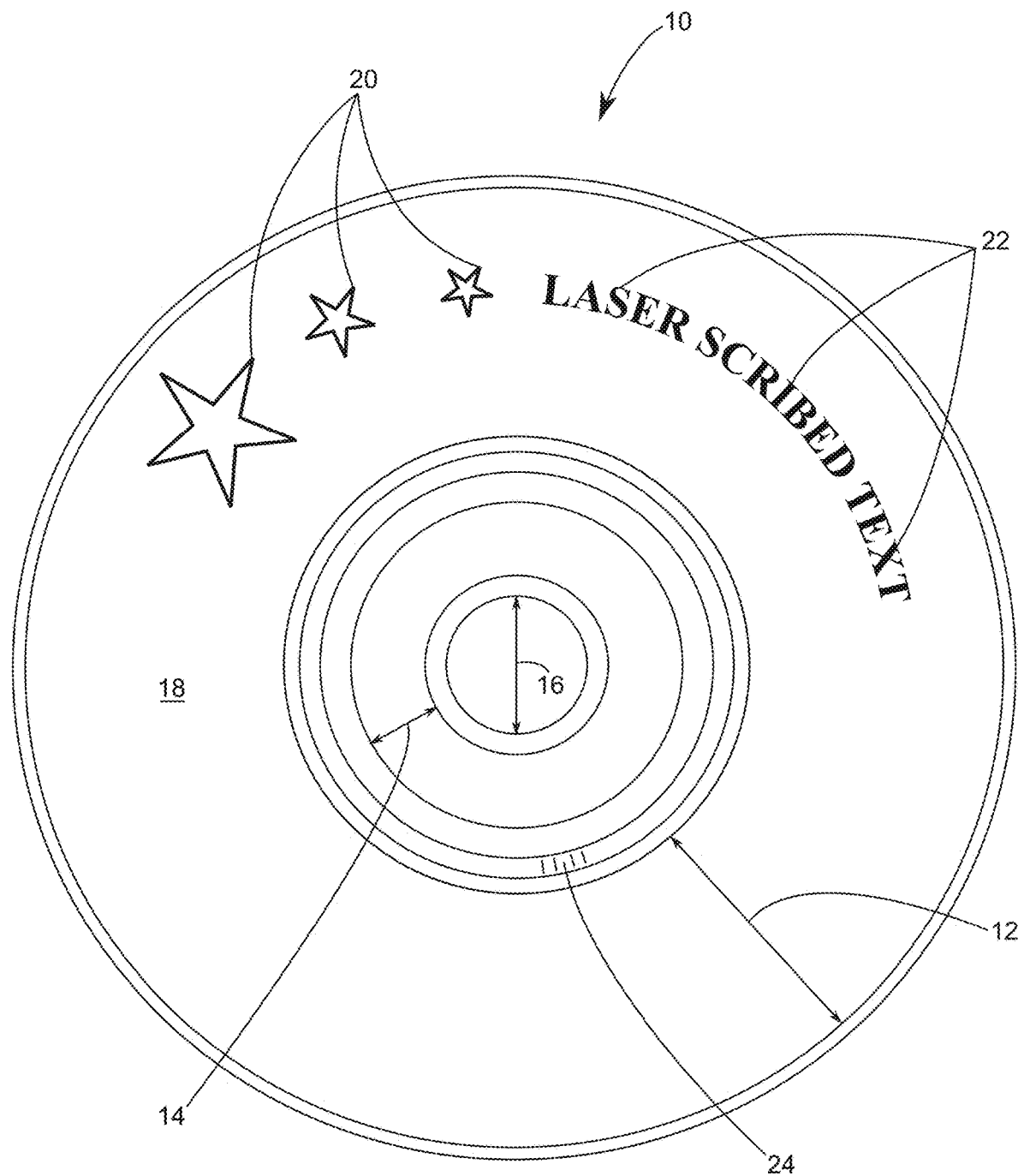
FIG. 1 depicts the label side of a prior art direct-to-disc labeling type CD/DVD disc.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

The present disclosure provides an inexpensive process for making and patterning an interconnected corrugated carbon-based network having stringent requirements for a high surface area with highly tunable electrical conductivity and electrochemical properties. The embodiments described herein not only meet these stringent requirements, but provide direct control over the conductivity and patterning of interconnected corrugated carbon-based networks while creating flexible electronic devices in a single step process. Moreover, the production of these interconnected corrugated carbon-based networks does not require reducing agents, or expensive equipment. The simple direct fabrication of interconnected corrugated carbon-based networks on flexible substrates therefore simplifies the development of lightweight electronic devices. The interconnected corrugated carbon-based networks can be synthesized on various substrates, such as plastic, metal, and glass. Herein an all-organic $NO_2$ gas sensor, a fast redox active electrode, and a scaffold for the direct growth of platinum (Pt) nanoparticles are demonstrated.

In at least one embodiment, the interconnected corrugated carbon-based networks are conducting films produced using a common and inexpensive infrared laser that fits inside a compact disc/digital versatile disc (CD/DVD) optical drive unit that provides a direct-to-disc label writing function. LightScribe (Registered Trademark of Hewlett Packard Corporation) and LabelFlash (Registered Trademark of Yamaha Corporation) are exemplary direct-to-disc labeling technologies that pattern text and graphics onto the surface of a CD/DVD disc. LightScribe DVD drives are commercially available for around $20 and the LightScribing process is controlled using a standard desktop computer.

FIG. 1 depicts the label side of a standard direct-to-disc labeling type CD/DVD disc 10 that includes a label area 12 and a clamping area 14 that surrounds a centering hole 16. A dye film 18 covers the label area 12 and is sensitive to laser energy that is typically directed onto the label area 12 to produce a permanent visible image that may comprise graphics 20 and text 22. A position tracking indicia 24 is usable by an optical disc drive (not shown) to accurately locate an absolute angular position of the CD/DVD disc 10 within the optical disc drive so that the graphics 20 and/or text 22 can be re-written to provide increased contrast. Moreover, the position tracking indicia 24 is usable by the optical disc drive to allow additional graphics and/or text to be written without undesirably overwriting the graphics 20 and/or text 22.

Figure 2:
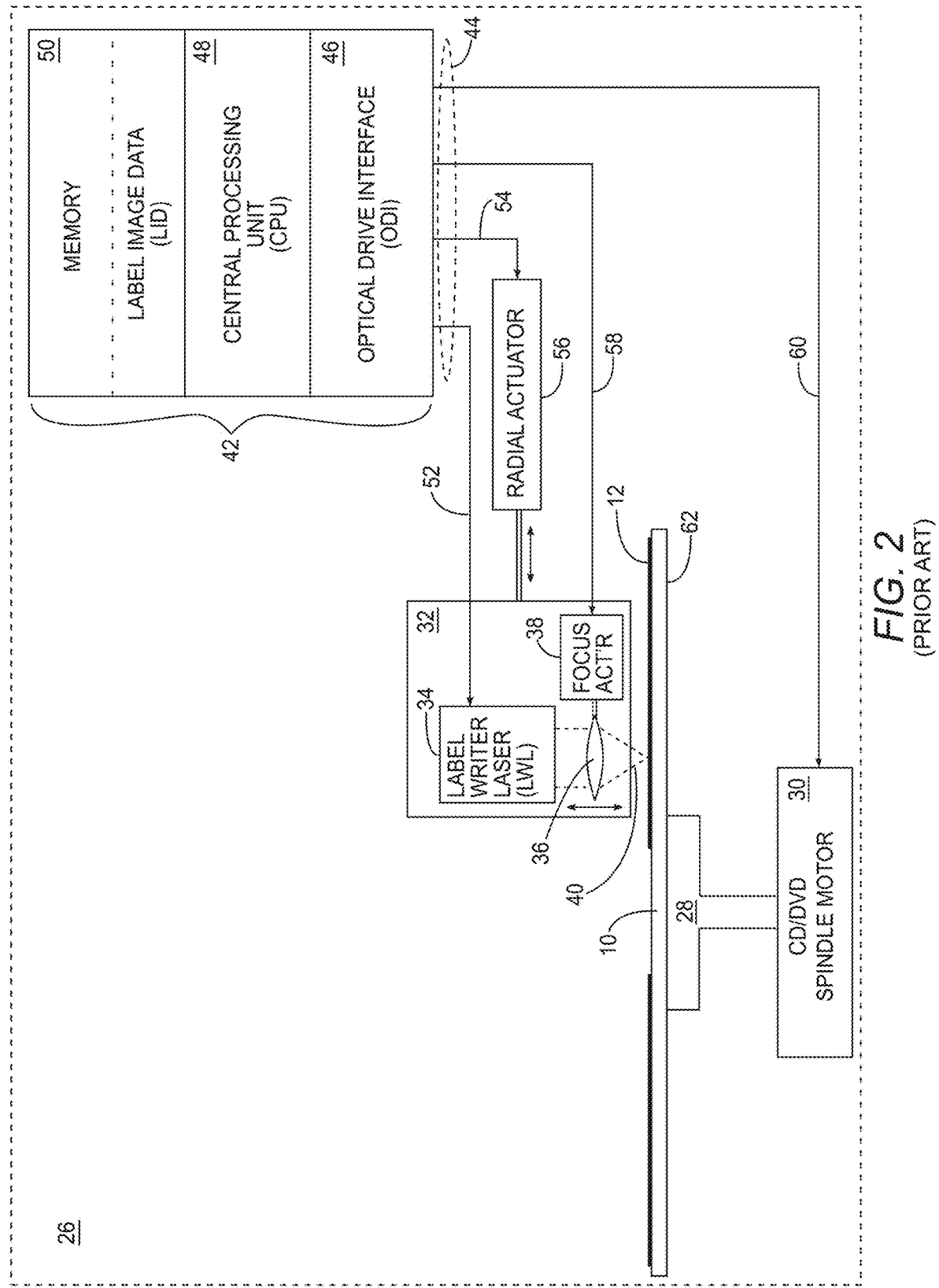
FIG. 2 is a schematic of a prior art direct-to-disc labeling type optical disc drive.

FIG. 2 is a schematic of a prior art direct-to-disc labeling type optical disc drive system 26. In this exemplary case, the CD/DVD disc 10 is depicted in cross-section and loaded onto a spindle assembly 28 that is driven by a CD/DVD spindle motor 30. The label area 12 is shown facing a laser assembly 32 that includes a label writer laser (LWL) 34, a lens 36, and a focus actuator 38. The LWL 34 is typically a laser diode. Exemplary specifications for the LWL 34 includes a maximum pulse optical power of 350 mW at 780 nm emission and a maximum pulse output power of 300 mW at 660 nm emission. A laser beam 40 emitted by the LWL 34 is focused by the lens 36 that is alternately translated towards and away from the LWL 34 by the focus actuator 38 in order to maintain focus of the laser beam 40 onto the label area 12 of the CD/DVD disc 10. The laser beam 40 is typically focused to a diameter that ranges from around 0.7 µm to around 1 µm.

The laser assembly 32 is responsive to a control system 42 that provides control signals 44 through an optical drive interface (ODI) 46. The control system 42 further includes a central processor unit (CPU) 48 and a memory 50. Label image data (LID) having information needed to realize a permanent image to be written onto the label area 12 of the CD/DVD disc 10 is processed by the CPU 48, which in turn provides an LID stream signal 52 that pulses the LWL 34 on and off to heat the dye film 18 to realize the image defined by the LID.

The CPU 48 also processes the LID through the ODI 46 to provide a position control signal 54 to a radial actuator 56 that translates the laser assembly 32 in relation to the label area 12 in response to position information contained in the LID. In some versions of the present embodiments, the optical disc drive system 26 monitors the focus of the laser beam 40 with an optical receiver (not shown), so that the ODI 46 can generate a focus control signal 58 for the focus actuator 38. The ODI 46 also provides a motor control signal 60 for the CD/DVD spindle motor 30 that maintains an appropriate rotation speed of the CD/DVD disc 10 while a label writing process is ongoing.

In some versions of the optical disc drive system 26 the LWL 34 is used exclusively for label writing directly to the label area 12 of the CD/DVD disc 10 and a separate laser diode (not shown) is used to write and/or read data to/from a data side 62 of the CD/DVD disc 10. In other versions of the optical disc drive system 26, the LWL 34 is used for label writing and data reading and/or writing. When the LWL 34 is used for data reading and/or writing, the CD/DVD disc 10 is flipped over to expose the data side 62 of the CD/DVD disc 10 to the laser beam 40. In versions wherein the LWL 34 is also used as a data read/write laser, the laser assembly 32 includes optical pick-up components (not shown) such as a beam splitter and at least one optical receiver. The output power of the LWL 34 is typically around 3 mW during data read operations.

In order to use the optical disc drive system 26 to realize an inexpensive process for making and patterning an interconnected corrugated carbon-based network having a high surface area with highly tunable electrical conductivity and electrochemical properties, a carbon-based film is substituted for the dye film 18 (FIG. 1). In one embodiment, graphite oxide (GO) is synthesized from high purity graphite powder using a modified Hummer's method. Dispersions of GO in water (3.7 mg/mL) are then used to make GO films on various substrates. Exemplary substrates include but are not limited to polyethylene terephthalate (PET), nitrocellulose membrane (with 0.4 µm pore size), aluminum foil, carbonized aluminum, copper foil, and regular copier paper.

Figure 3:
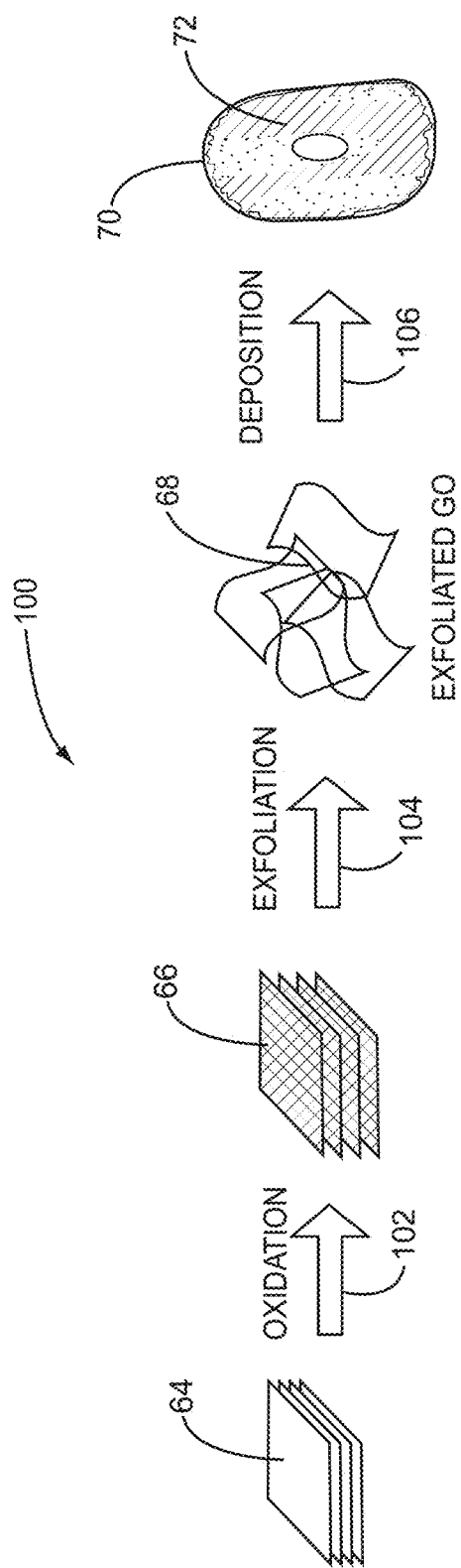
FIG. 3 is a process diagram for an exemplary process for providing graphite oxide (GO) films on a substrate.

Referring to FIG. 3, a process 100 begins with providing graphite powder 64. The graphite powder 64 undergoes an oxidation reaction using the modified Hummer's method to become GO 66 (step 102). However, it is to be understood that other oxidation methods for producing GO are available and such methods are within the scope of the present disclosure. An exfoliation procedure produces exfoliated GO 68 (step 104). The exfoliation procedure may be accomplished via ultrasonication. It is to be understood that the exfoliated GO 68 results from a partial exfoliation and not a complete exfoliation to a single layer of GO. The partial exfoliation is used to create a high accessible surface area that enables a fast redox response which enables a fast sensor response. Additionally, the partial exfoliation of GO 68 provides the high surface area for growing metal nanoparticles that could then be used in catalysis. A substrate 70 carries a GO film 72 that is produced by a deposition procedure that deposits the exfoliated GO 68 onto the substrate 70 (step 106). In at least some embodiments, a GO film 72 is made by either drop-casting or vacuum filtering GO dispersions onto the substrate 70 that is the size of a CD/DVD disc. The GO film 72 is typically allowed to dry for 24 hours under ambient conditions. However, controlling conditions to expose the GO film 72 to a relatively lower humidity and relatively higher temperature will dry the GO film 72 relatively quickly. The term GO herein refers to graphite oxide.

Figure 4:
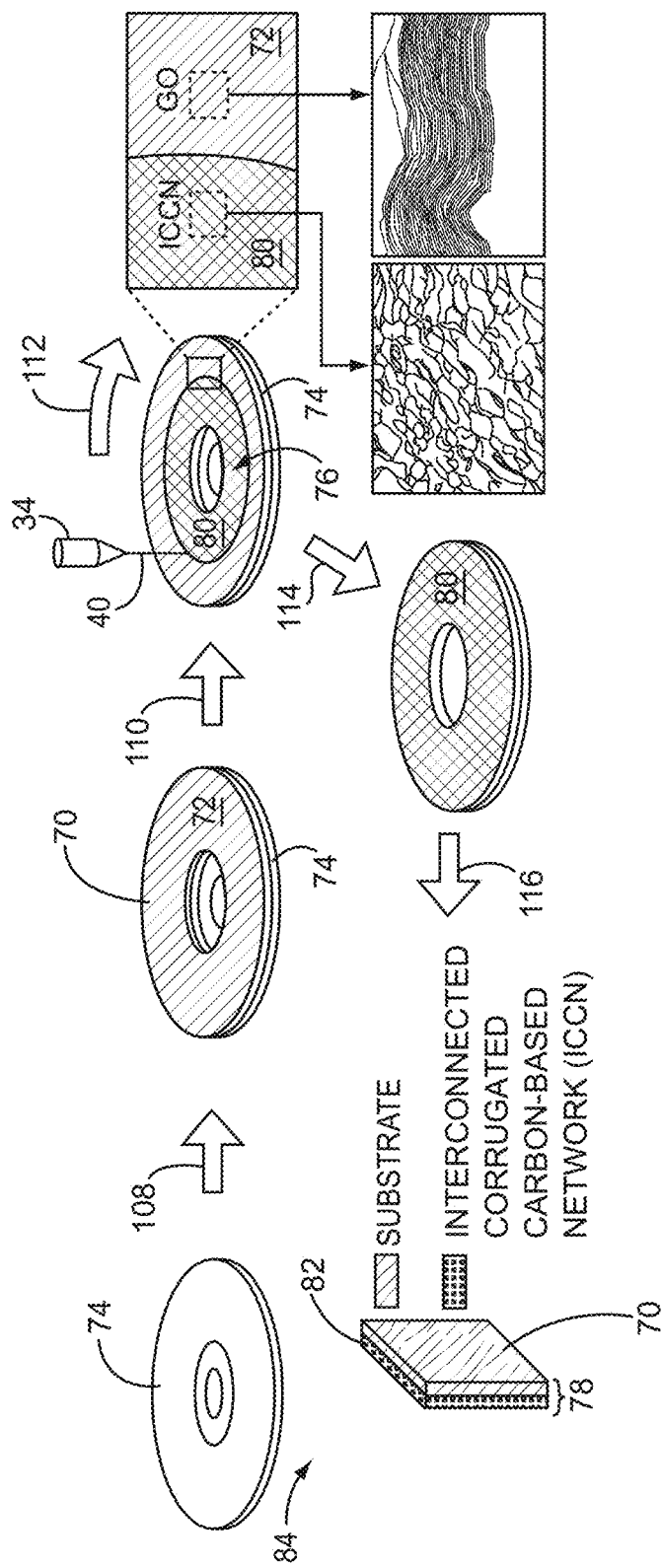
FIG. 4 is a process diagram for laser scribing an interconnected corrugated carbon-based network and then fabricating electrical components from the interconnected corrugated carbon-based network.

Referring to FIG. 4, individual ones of the GO film(s) 72 are then affixed to a substrate carrier 74, which has dimensions similar to the CD/DVD disc 10 (FIG. 1) (step 108). The substrate carrier 74 carrying the substrate 70 with the GO film 72 is loaded into the optical disc drive system 26 (FIG. 2) such that the GO film 72 faces the LWL 34 for laser treatment (step 110). In this way, the present embodiments use the GO film 72 in place of the dye film 18 (FIG. 1). It is to be understood that the substrate carrier 74 can be a rigid or semi-rigid disc onto which the GO film 72 can be fabricated directly. In that case, the substrate carrier 74 replaces the function of the substrate 70.

Images 76 for realizing electrical components 78 are patterned in concentric circles, moving outward from the center of the substrate carrier 74 (step 112). The laser irradiation process results in the removal of oxygen species and the reestablishment of $sp^2$ carbons. This causes a change in the conductivity of the GO film 72 with a typical resistance of >20 MΩ/sq to become a relatively highly conducting plurality of expanded and interconnected carbon layers that make up an interconnected corrugated carbon-based network 80. The number of times the GO film 72 is laser treated results in a significant and controllable change in the conductivity of the interconnected corrugated carbon-based network 80. The interconnected corrugated carbon-based network 80 has a combination of properties that include high surface area and high electrical conductivity in an expanded interconnected network of carbon layers. In one embodiment the plurality of expanded and interconnected carbon layers has a surface area of greater than 1400 $m^2/g$. In another embodiment, the plurality of expanded and interconnected carbon layers has a surface area of greater than 1500 $m^2/g$. In yet another embodiment, the surface area is around about 1520 $m^2/g$. In one embodiment, the plurality of expanded and interconnected carbon layers yields an electrical conductivity that is greater than about 1500 S/m. In another embodiment, the plurality of expanded and interconnected carbon layers yields an electrical conductivity that is greater than about 1600 S/m. In yet another embodiment, the plurality of expanded and interconnected carbon layers yields an electrical conductivity of around about 1650 S/m. In still another embodiment, the plurality of expanded and interconnected carbon layers yields an electrical conductivity that is greater than about 1700 S/m. In yet one more embodiment, the plurality of expanded and interconnected carbon layers yields an electrical conductivity of around about 1738 S/m. Moreover, in one embodiment, the plurality of expanded and interconnected carbon layers yields an electrical conductivity that is greater than about 1700 S/m and a surface area that is greater than about 1500 m$^2$/g. In another embodiment, the plurality of expanded and interconnected carbon layers yields an electrical conductivity of around about 1650 S/m and a surface area of around about 1520 m$^2$/g.

The electrical components 78 comprising electrodes 82 used in the fabrication of a device 84 are laser irradiated 6 times before reaching the relatively high conductivity of around about 1738 S/m. The laser irradiation process takes about 20 minutes per cycle. Afterwards, the substrate 70 carrying the interconnected corrugated carbon-based network 80 and any remaining GO film 72 is removed from the substrate carrier 74 (step 114). Next, the interconnected corrugated carbon-based network 80 is fabricated into the electrical components 78 that make up the device 84 (step 116). In this exemplary case, portions of the interconnected corrugated carbon-based network 80 on the substrate 70 are cut into rectangular sections to make the electrical components 78, which include the electrodes 82 formed from the interconnected corrugated carbon-based network 80.

Figure 5:
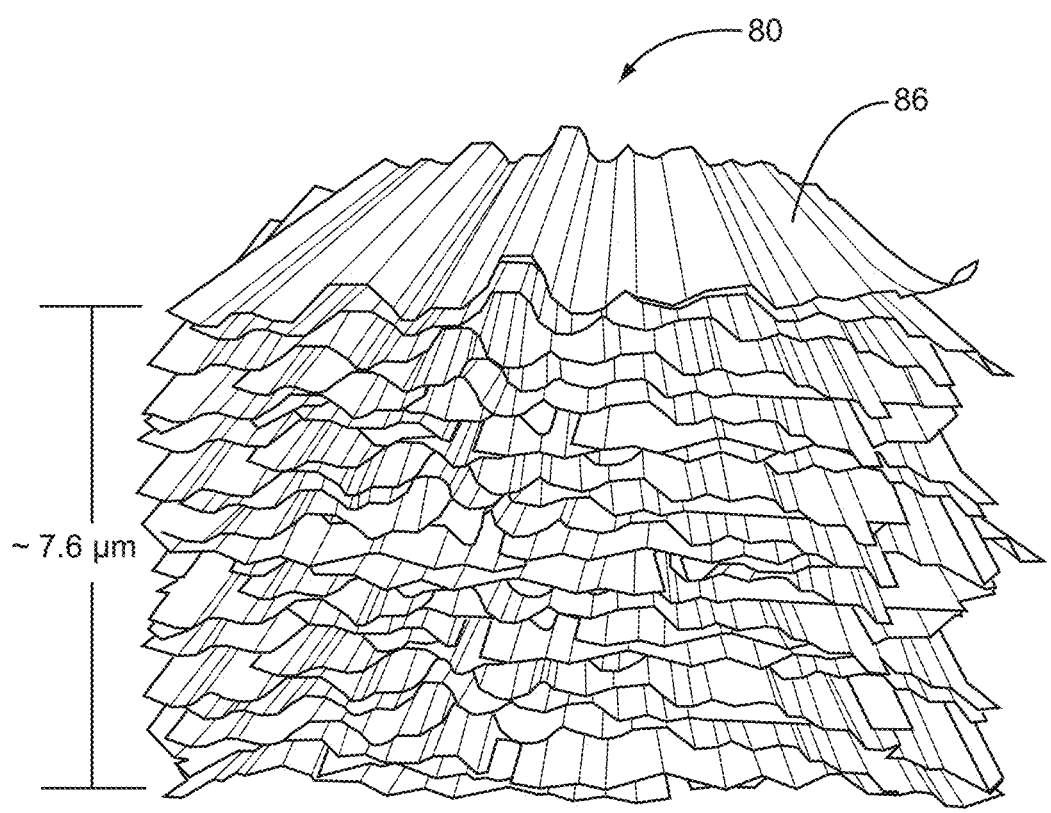
FIG. 5 is a line drawing of a sample of the interconnected corrugated carbon-based network of the present embodiments.

The interconnected corrugated carbon-based network 80 possesses a very low oxygen content of only 3.5%. In other embodiments, the oxygen content of the expanded and interconnected carbon layers ranges from around about 1% to around about 5%. FIG. 5 is a line drawing of a sample of the interconnected corrugated carbon-based network 80, which is made up of the plurality of expanded and interconnected carbon layers that include corrugated carbon layers such as a single corrugated carbon sheet 86. In one embodiment, each of the expanded and interconnected carbon layers comprises at least one corrugated carbon sheet that is one atom thick. In another embodiment, each of the expanded and interconnected carbon layers comprises a plurality of corrugated carbon sheets that are each one atom thick. The thickness of the interconnected corrugated carbon-based network 80, as measured from cross-sectional scanning electron microscopy (SEM) and profilometry, was found to be around about 7.6 µm. In one embodiment, a range of thickness of the plurality of expanded and interconnected carbon layers making up the interconnected corrugated carbon-based network 80 is from around 7 µm to 8 µm.

Figures 6A, 6B:
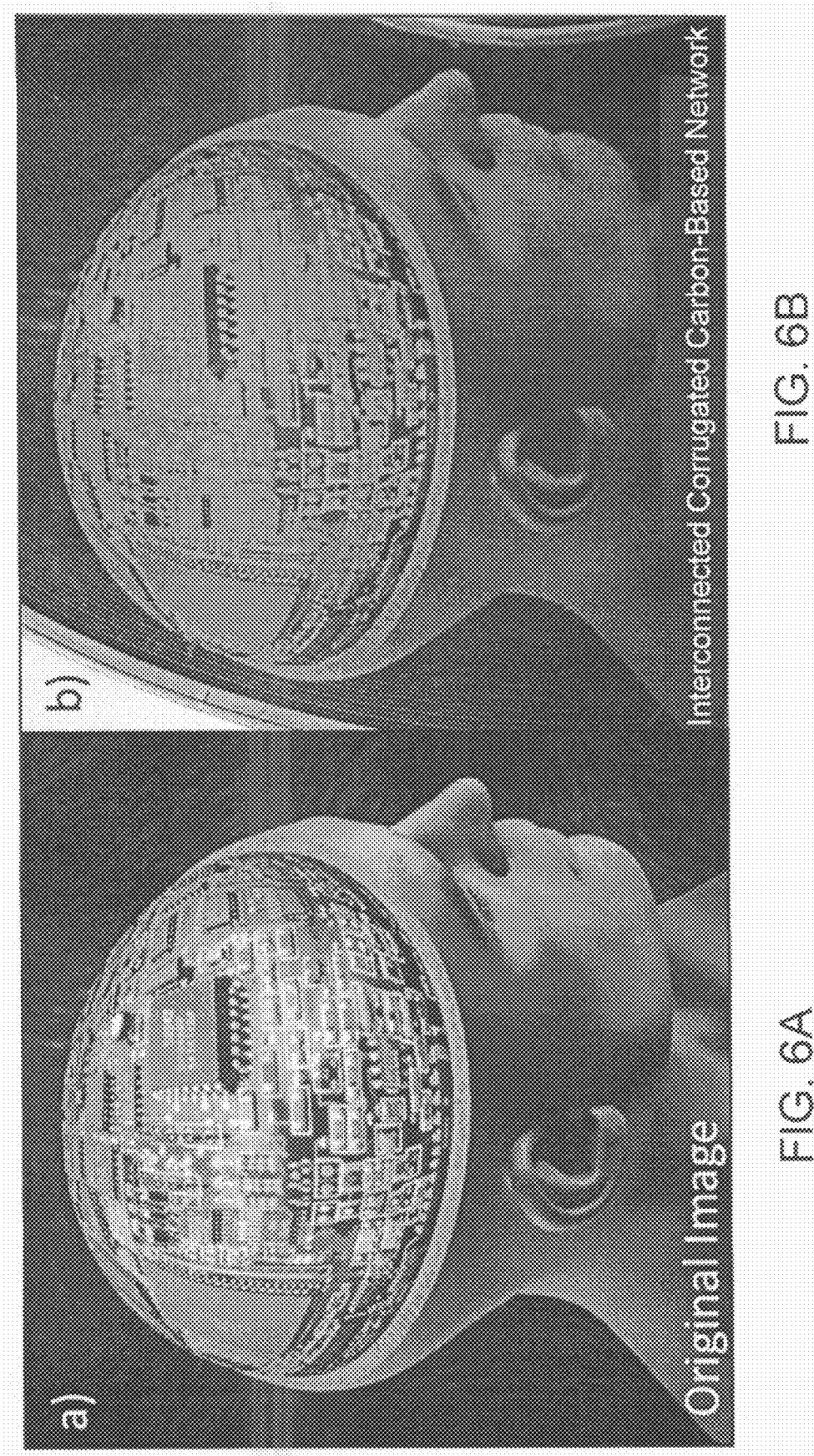
FIG. 6A is an artwork image of a man's head covered with circuits.
FIG. 6B is a photograph of a GO film after the artwork image of FIG. 6A is directly patterned on the GO film using the laser scribing technique of the present disclosure.
Figure 7:
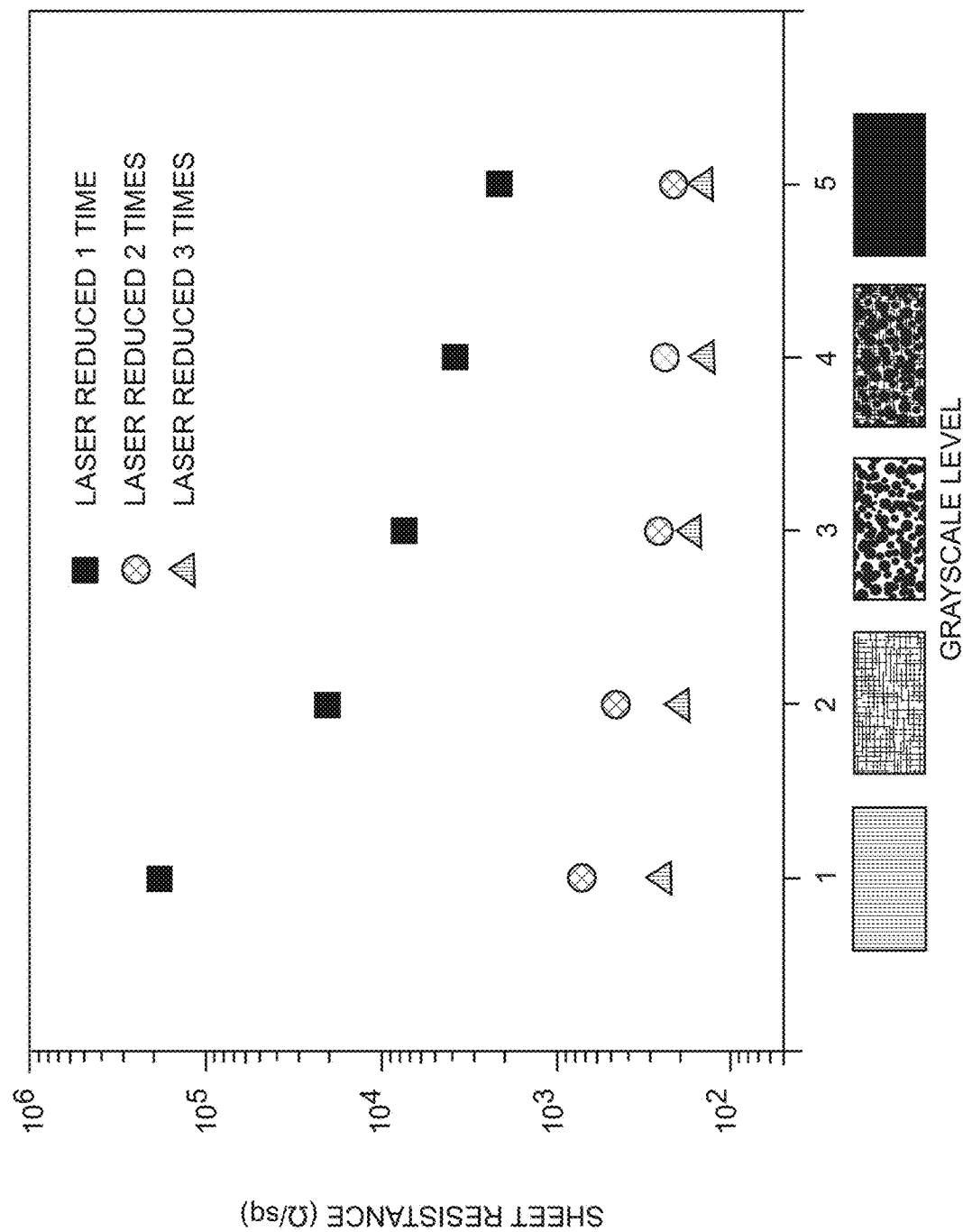
FIG. 7 is a graph that provides a comparison between changes in electrical conductivity by reducing the GO film of FIG. 6B by using various grayscale levels to laser scribe the artwork of FIG. 6A to produce the patterned GO film of FIG. 6B.

As an illustration of the diversity in image patterning that is possible, a complex image formed by the direct laser reduction of GO is shown in FIGS. 6A and 6B. FIG. 6A is an artwork image of a man's head covered with circuits. FIG. 6B is a photograph of a GO film after the artwork image of FIG. 6A is directly patterned on the GO film using the laser scribing technique of the present disclosure. Essentially, any part of the GO film that comes in direct contact with the 780 nm infrared laser is effectively reduced to an interconnected corrugated carbon-based network, with the amount of reduction being controlled by the laser intensity; a factor that is determined by power density of the laser beam impinging on the GO film. The resulting image of FIG. 6B is an effective print of the original image of FIG. 6A. However, in this case the image of FIG. 6B is made up of various reductions of the GO film. As expected, the darkest black areas indicate exposure to the strongest laser intensities, while the lighter gray areas are only partially reduced. Since different grayscale levels directly correlate with the laser's intensity, it is possible to tune the electrical properties of the generated interconnected corrugated carbon-based network over five to seven orders of magnitude in sheet resistance (Ω/sq) by simply changing the grayscale level used during the patterning process. As illustrated in FIG. 7, there is a clear relationship between sheet resistance, grayscale level and the number of times the GO film is laser irradiated. Control over conductivity from a completely insulating GO film, with a typical sheet resistance value of >20 MΩ/sq, to a conducting interconnected corrugated carbon-based network that registers a sheet resistance value of approximately 80 Ω/sq, which translates to a conductivity of ~1650 S/m, is possible. This method is sensitive enough to differentiate between similar grayscale levels as shown in the graph of FIG. 7, where the sheet resistance varies significantly with only a small variation in grayscale level. In addition, the number of times a GO film is laser treated results in a significant and controllable change in sheet resistance. Each additional laser treatment lowers the sheet resistance as seen in FIG. 7, where a film is laser irradiated once (black squares), twice (circles) and three times (triangles) with respect to the grayscale level. Therefore, the film's sheet resistance is tunable both by controlling the grayscale level used and the number of times the film is reduced by the laser, a property that has so far been difficult to control through other methods.

Figure 8A:
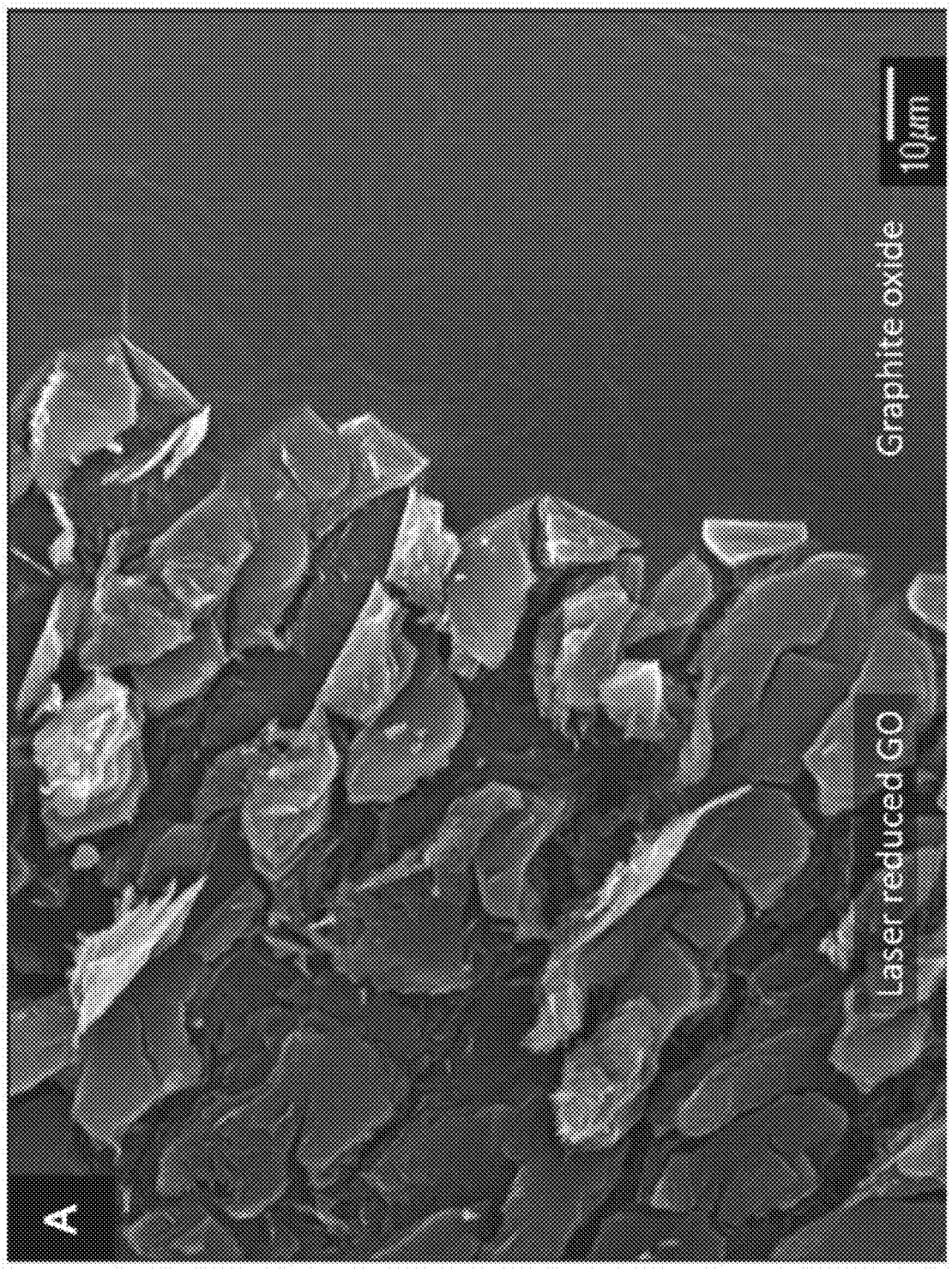
FIG. 8A is a scanning electron microscope (SEM) image that illustrates an infrared laser's effect on GO film prior to laser treatment on the right side of the image in contrast to an aligned, interconnected corrugated carbon-based network on the left side of the image.

Scanning electron microscope (SEM) techniques are usable to understand the effects a low energy infrared laser has on the structural properties of GO film by comparing the morphological differences between an interconnected corrugated carbon-based network and untreated graphite oxide GO film. FIG. 8A is an SEM image that illustrates the infrared laser's effect on GO film prior to laser treatment on the right side of the image in contrast to an aligned, interconnected corrugated carbon-based network on the left side of the image that occurs after being reduced with the infrared laser. The image not only gives a clear definition between the interconnected corrugated carbon-based network and untreated GO regions, but also demonstrates the level of precision possible when using this method as a means to pattern and reduce GO. The regions of interconnected corrugated carbon-based network, which result from the laser treatment, can be further analyzed through cross-sectional SEM.

Figure 8B:
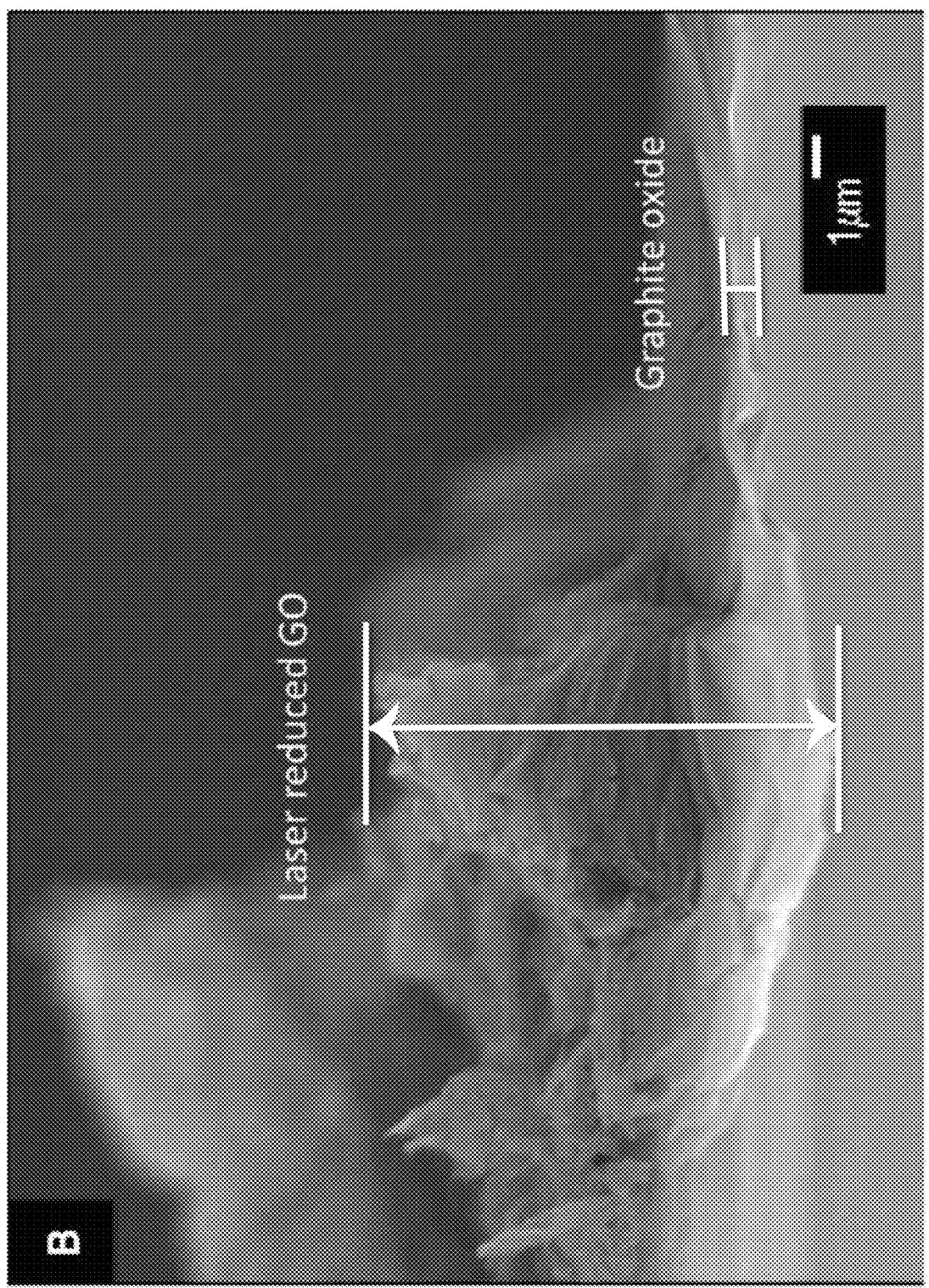
FIG. 8B is an SEM image showing that an interconnected corrugated carbon-based network has a thickness that is approximately 10 times larger in comparison to that of untreated GO film.
Figure 8C:
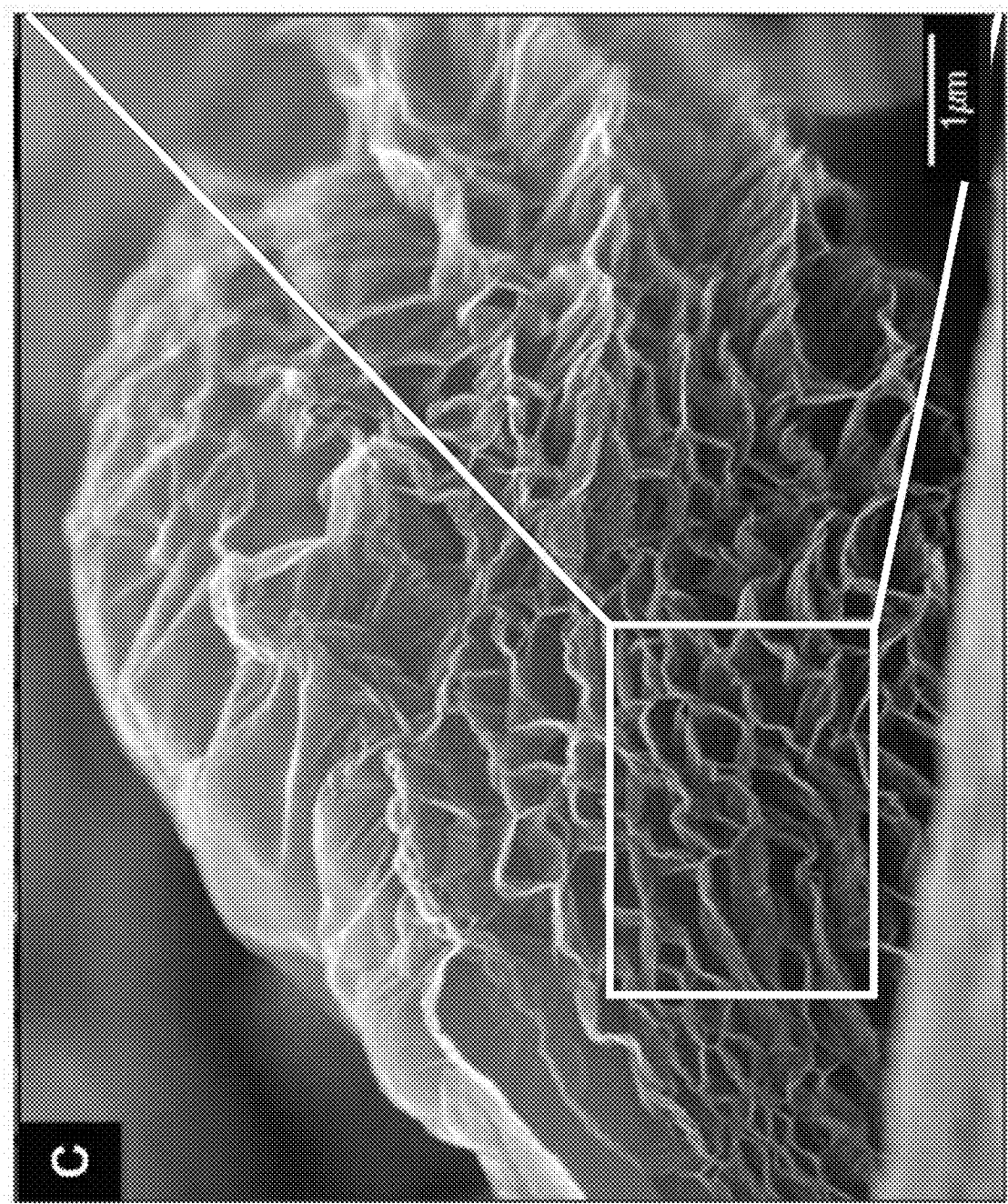
FIG. 8C is an SEM image showing a cross-sectional view of a single laser converted interconnected corrugated carbon-based network.

FIG. 8B is an SEM image showing a cross-sectional view of a free standing film of laser treated and untreated GO film, which shows a significant difference between GO film thicknesses. As indicated by the white brackets in FIG. 8B, an interconnected corrugated carbon-based network increases in thickness by approximately 10 times in comparison to that of untreated GO film. Moreover, a range of thickness of the plurality of expanded and interconnected carbon layers is from around 7 µm to around 8 µm. In one embodiment, an average thickness of the plurality of expanded and interconnected carbon layers is around 7.6 µm. The increased thickness stems from rapid degassing of gases generated and released during laser treatment, similar to thermal shock, which effectively causes the reduced GO to expand and exfoliate as these gases rapidly pass through the GO film. FIG. 8C is an SEM image showing a cross-sectional view of a single interconnected corrugated carbon-based network, which shows an expanded structure that is a characteristic of the interconnected corrugated carbon-based network of the present disclosure.

Figure 8D:
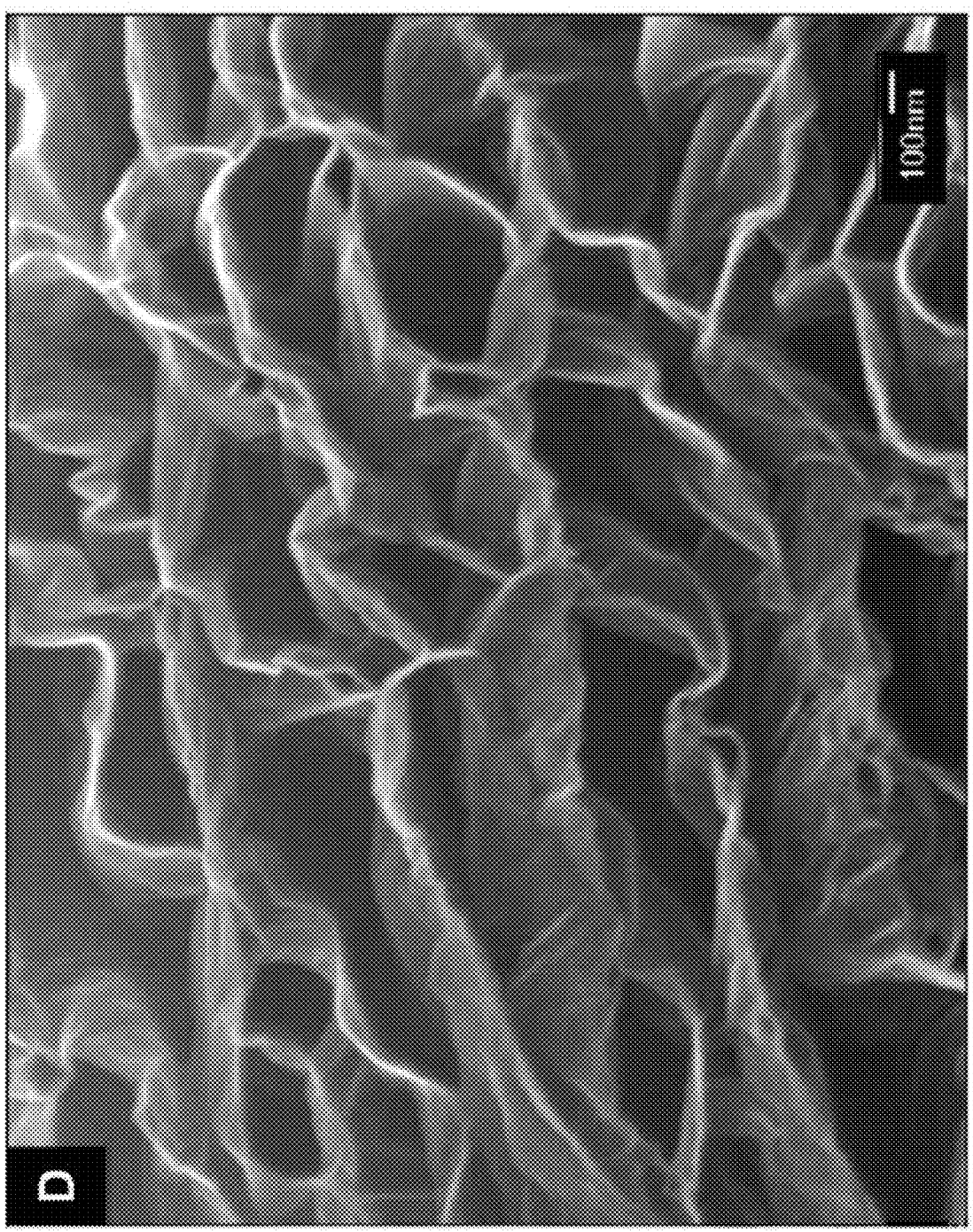
FIG. 8D is an SEM image showing a greater magnification of a selected area within the interconnected corrugated carbon-based network in FIG. 8C.

FIG. 8D is an SEM image showing a greater magnification of a selected area within the corrugated carbon-based network in FIG. 8C. The SEM image of FIG. 8D allows the thickness of the plurality of expanded and interconnected carbon layers to be calculated to be between 5-10 nm. However, the number of carbon layers in the plurality of expanded and interconnected carbon layers making up the interconnected corrugated carbon-based network is above 100. In another embodiment the number of carbon layers in the plurality of expanded and interconnected carbon layers is greater than 1000. In yet another embodiment the number of carbon layers in the plurality of expanded and interconnected carbon layers is greater than 10,000. In still another embodiment, the number of carbon layers in the plurality of expanded and interconnected carbon layers is greater than 100,000. The SEM analysis shows that although an infrared laser emission is only marginally absorbed by GO, enough power and focus (i.e., power density) can cause sufficient thermal energy to efficiently reduce, deoxygenate, expand, and exfoliate the GO film. Moreover, the surface area of the interconnected corrugated carbon-based network is greater than about 1500 $m^2/g$.

Since each of the carbon layers have a theoretical surface area of 2630 $m^2/g$, a surface greater than 1500 $m^2/g$ indicates that almost all surfaces of the carbon layers are accessible. The interconnected corrugated carbon-based network has an electrical conductivity that is greater than 17 S/cm. The interconnected corrugated carbon-based network forms when some wavelength of light hits the surface of the GO, and is then absorbed to practically immediately convert to heat, which liberates carbon dioxide ($CO_2$). Exemplary light sources include but are not limited to a 780 nm laser, a green laser, and a flash lamp. The light beam emission of the light sources may range from near infrared to ultraviolet wavelengths. The typical carbon content of the interconnected corrugated carbon-based network is greater than 97% with less than 3% oxygen remaining. Some samples of the interconnected corrugated carbon-based network are greater than 99% carbon even though the laser reduction process is conducted in the air.

Figure 9:
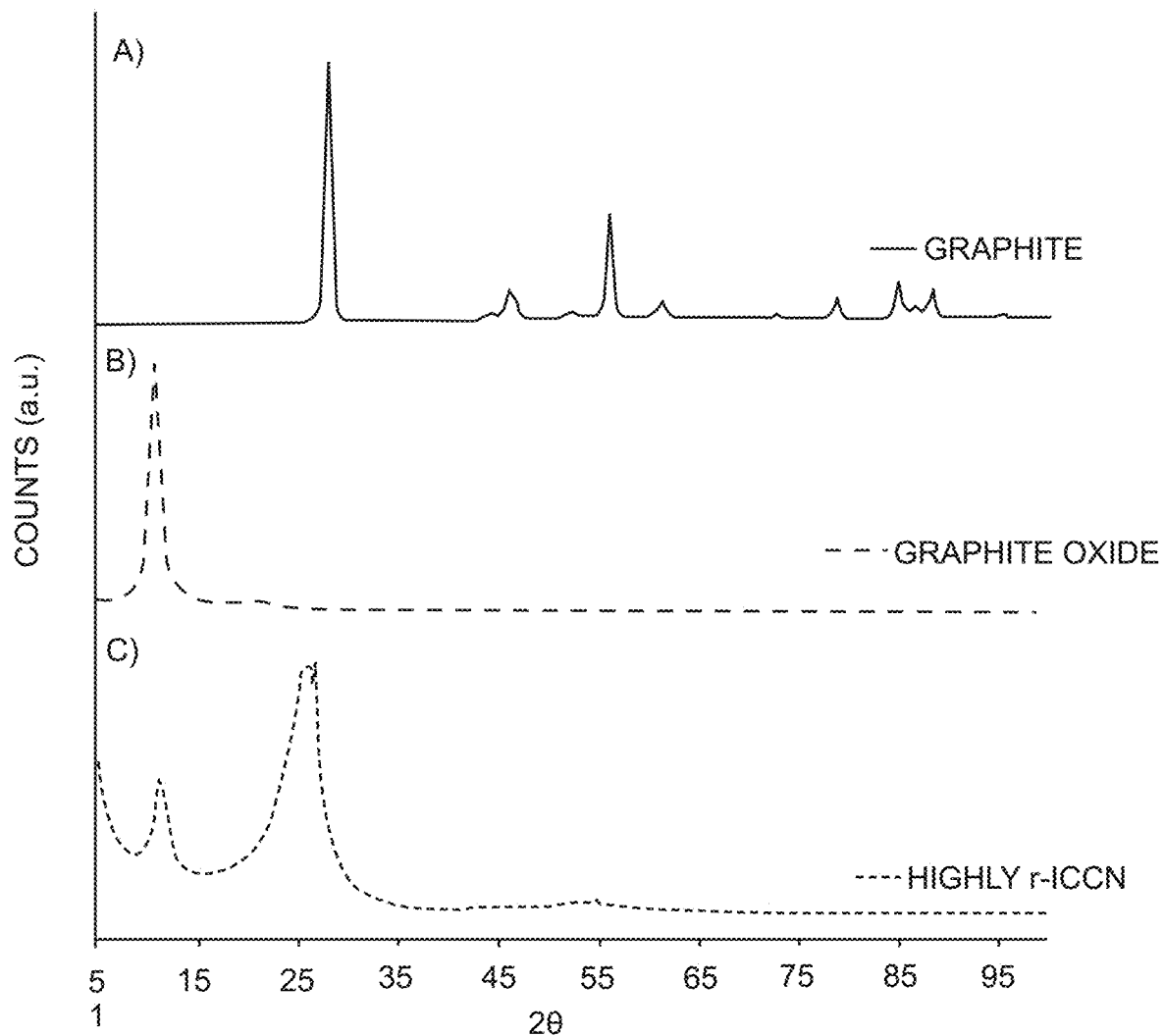
FIG. 9 compares a powder X-ray diffraction (XRD) pattern of the interconnected corrugated carbon-based network with both graphite and graphite oxide diffraction patterns.
Figure 10:
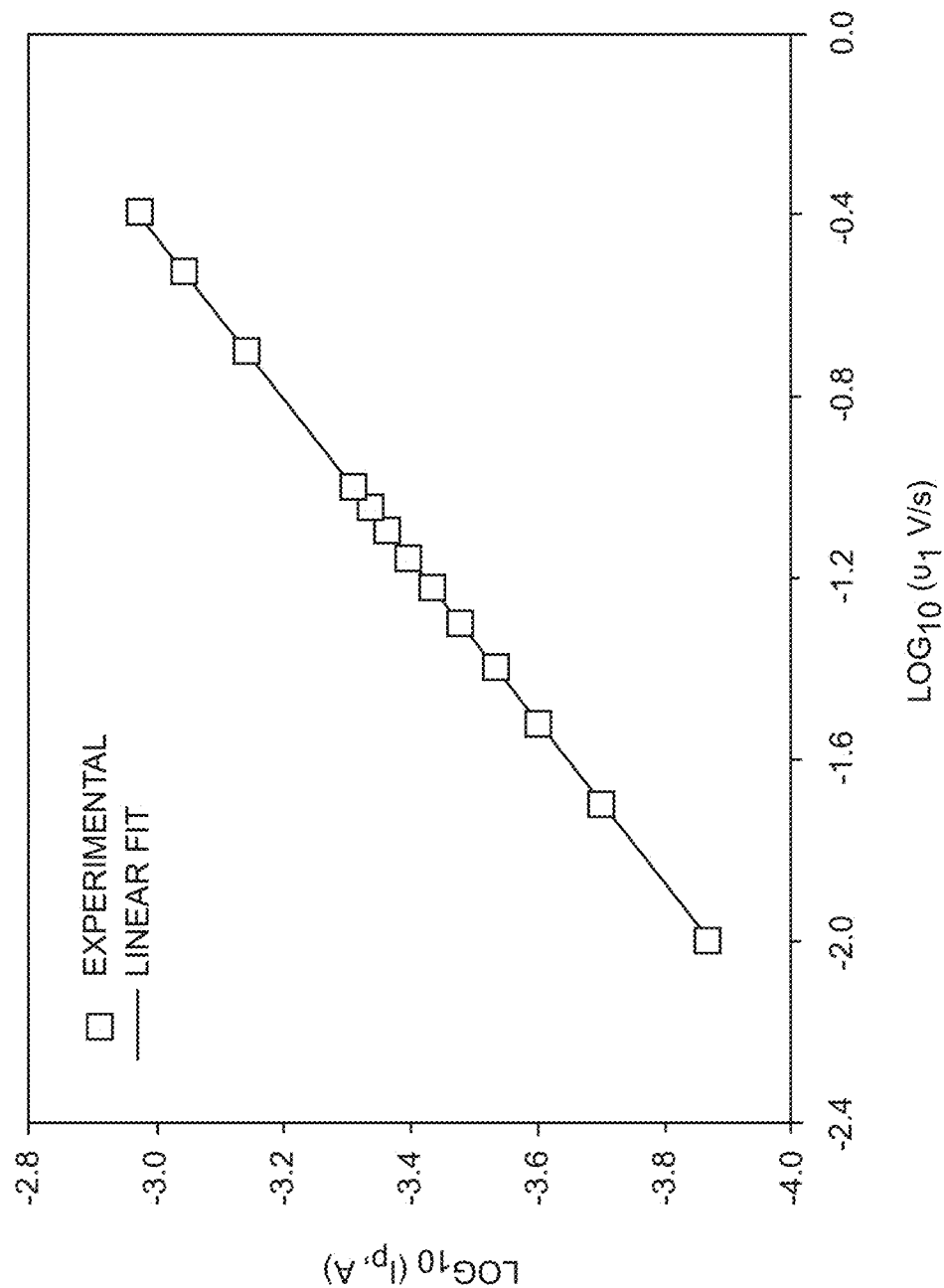
FIG. 10 is a plot of $\log_{10}$ of peak current versus $\log_{10}$ of an applied voltammetric scan rate.

FIG. 9 compares a powder X-ray diffraction (XRD) pattern of the corrugated carbon-based network with both graphite and graphite oxide diffraction patterns. A typical XRD pattern for graphite, shown in FIG. 9 trace A, displays the characteristic peak of $2\theta=27.8°$ with a d-spacing of 3.20 Å. An XRD pattern (FIG. 9, trace B) for GO, on the other hand, exhibits a single peak of $2\theta=10.76°$, which corresponds to an interlayer d-spacing of 8.22 Å. The increased d-spacing in GO is due to the oxygen containing functional groups in graphite oxide sheets, which tend to trap water molecules between the basal planes, causing the sheets to expand and separate. The XRD pattern of the corrugated carbon-based network (FIG. 9, trace C) shows the presence of both GO (10.76° $2\theta$) and a broad graphitic peak at 25.97° $2\theta$ associated with a d-spacing of 3.43 Å, (FIG. 10). The GO presence in the corrugated carbon-based network is expected since the laser has a desirable penetration depth, which results in the reduction of only the top portion of the film with the bottom layer being unaffected by the laser. The small presence of GO is more prominent in thicker films, but begins to diminish in thinner films. In addition, one can also observe a partially obstructed peak at 26.66° $2\theta$, which shows a similar intensity to the broad 25.97° $2\theta$ peak. Both of these peaks are considered graphitic peaks, which are associated to two different lattice spacing between basal planes.

It has been previously shown that the immobilization of carbon nanotubes (CNTs) on glassy carbon electrodes will result in a thin CNT film, which directly affects the voltammetric behavior of the CNT modified electrodes. In a ferri/ferrocyanide redox couple, the voltammetric current measured at the CNT modified electrode will likely have two types of contributions. The thin layer effect is a significant contributor to the voltammetric current. The thin layer effect stems from the oxidation of ferrocyanide ions, which are trapped between the nanotubes. The other contribution results from the semi-infinite diffusion of ferrocyanide towards the planar electrode surface. Unfortunately, the mechanistic information is not easily de-convoluted and requires knowledge of the film thickness.

In contrast, no thin layer effect is observed in association with the interconnected corrugated carbon-based network of the present disclosure. FIG. 10 is a plot of $\log_{10}$ of peak current versus $\log_{10}$ of an applied voltammetric scan rate. In this case, no thin layer effect is observed since the plot has a consistent slope of 0.53 and is linear. The slope of 0.53 is relatively close to theoretical values calculated using a semi-infinite diffusion model governed by the Randles-Sevcik equation:

$$i_p = 0.3443 A C_o^* \sqrt{\frac{D_o v (nF)^3}{RT}}$$

Figure 11A:
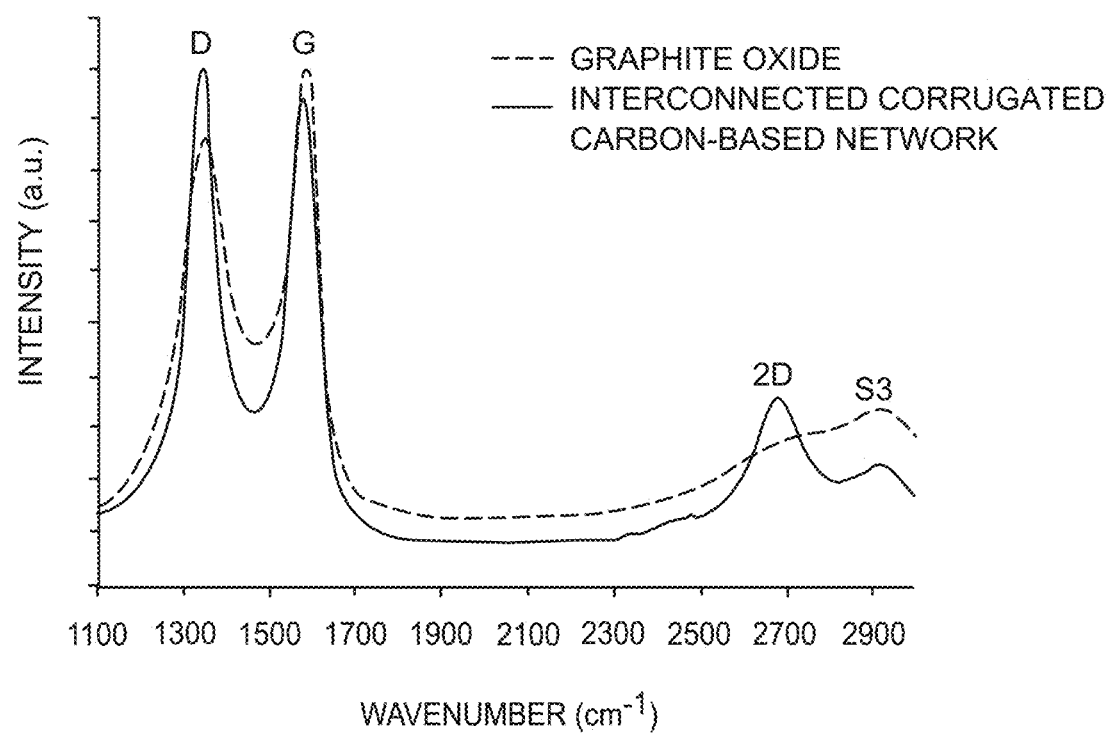
FIGS. 11A-11E are graphs related to Raman spectroscopy analysis.

Raman spectroscopy is used to characterize and compare the structural changes induced by laser treating GO film. FIGS. 11A-11E are graphs related to Raman spectroscopic analysis. As can be seen in FIG. 11A, characteristic D, G, 2D and S3 peaks are observed in both GO and the interconnected corrugated carbon-based network. The presence of the D band in both spectra suggests that carbon $sp^3$ centers still exist after reduction. Interestingly, the spectrum of the interconnected corrugated carbon-based network shows a slight increase in the D band peak at $\sim$1350 $cm^{-1}$. This unexpected increase is due to a larger presence of structural edge defects and indicates an overall increase in the amount of smaller graphite domains. The result is consistent with SEM analysis, where the generation of exfoliated accordion-like graphitic regions (FIG. 5) caused by the laser treatment creates a large number of edges. However the D band also shows a significant overall peak narrowing, suggesting a decrease in the types of defects in the interconnected corrugated carbon-based network. The G band experiences a narrowing and a decrease in peak intensity as well as a peak shift from 1585 to 1579 $cm^{-1}$. These results are consistent with the re-establishment of $sp^2$ carbons and a decrease in structural defects within the basal planes. The overall changes in the G band indicate a transition from an amorphous carbon state to a more crystalline carbon state. In addition, a prominent and shifted 2D peak from around about 2730 to around about 2688 $cm^{-1}$ is seen after GO is treated with the infrared laser, indicating a considerable reduction of the GO film and strongly points to the presence of a few-layer interconnected graphite structure. In one embodiment, the 2D Raman peak for the interconnected corrugated carbon-based network shifts from around about 2700 $cm^{-1}$ to around about 2600 $cm^{-1}$ after the interconnected corrugated carbon-based network is reduced from a carbon-based oxide. Moreover, as a result of lattice disorder, the combination of D-G generates an S3 second order peak, which appears at ~2927 cm$^{-1}$ and, as expected, diminishes with decreasing disorder after infrared laser treatment. In some embodiments, the plurality of expanded and interconnected carbon layers has a range of Raman spectroscopy S3 second order peak that ranges from around about 2920 cm$^{-1}$ to around about 2930 cm$^{-1}$. The Raman analysis demonstrates the effectiveness of treating GO with an infrared laser as a means to effectively and controllably produce the interconnected corrugated carbon-based network.

Figure 11B:
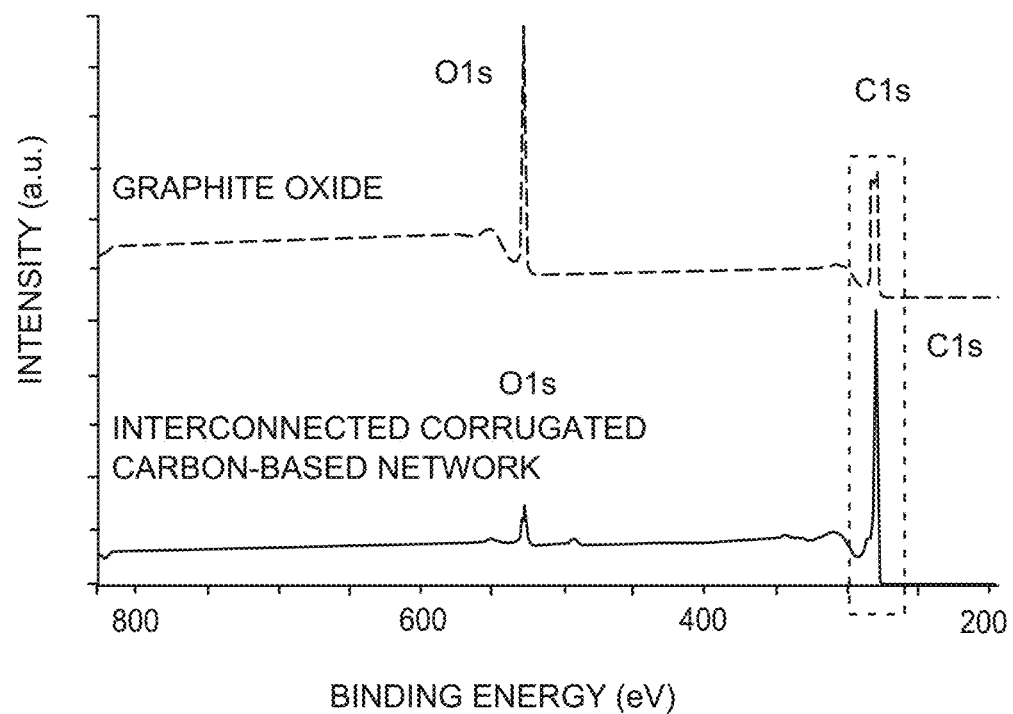

X-ray photoelectron spectroscopy (XPS) was employed to correlate the effects of laser irradiation on the oxygen functionalities and to monitor the structural changes on the GO film. Comparing the carbon to oxygen (C/O) ratios between GO and the interconnected corrugated carbon-based network provides an effective measurement of the extent of reduction achieved using a simple low energy infrared laser. FIG. 11B illustrates the significant disparity between the C/O ratios before and after laser treatment of the GO films. Prior to laser reduction, typical GO films have a C/O ratio of approximately 2.6:1, corresponding to a carbon/oxygen content of ~72% and 38%. On the other hand, the interconnected corrugated carbon-based network has an enhanced carbon content of 96.5% and a diminished oxygen content of 3.5%, giving an overall C/O ratio of 27.8:1. Since the laser reduction process takes place under ambient conditions, it is postulated that some of the oxygen present in the interconnected corrugated carbon-based network film is a result of the film having a static interaction with oxygen found in the environment.

Figure 11C:
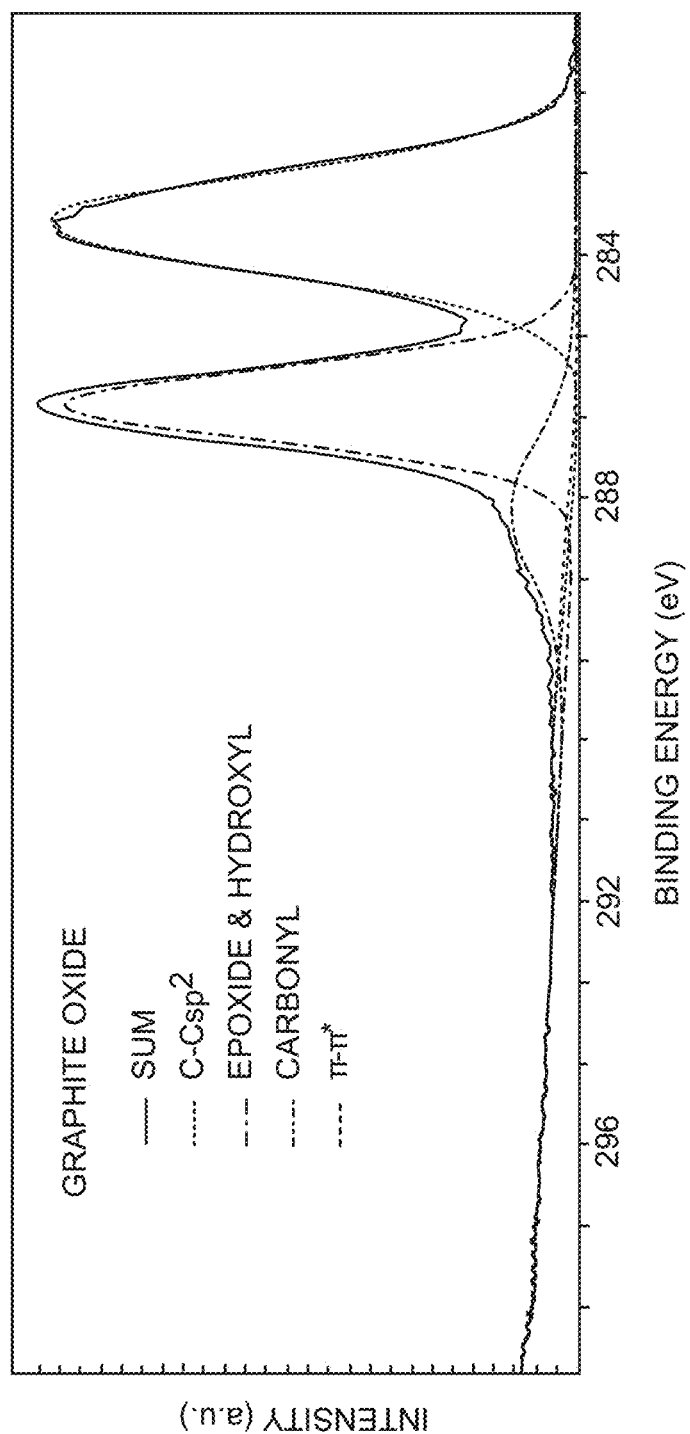

FIG. 11C shows that the C1s XPS spectrum of GO displays two broad peaks, which can be resolved into three different carbon components corresponding to the functional groups typically found on the GO surface, in addition to a small $\pi$ to $\pi^*$ peak at 290.4 eV. These functional groups include carboxyl, sp$^3$ carbons in the form of epoxide and hydroxyl, and sp$^2$ carbons, which are associated with the following binding energies: approximately 288.1, 286.8 and 284.6 eV, respectively.

Figure 11D:
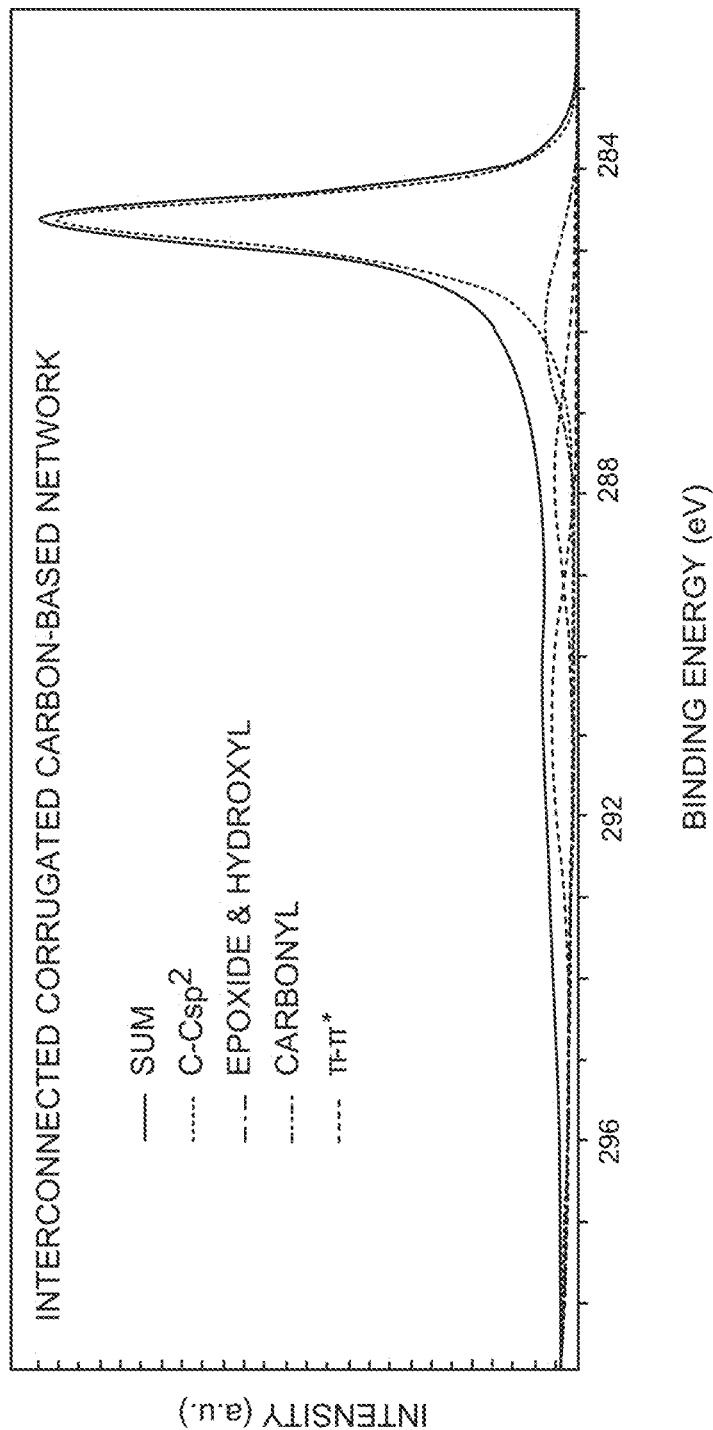

FIG. 11D shows expected results, in that the large degree of oxidation in GO results in various oxygen components in the GO C1s XPS spectrum. These results are in contrast to the interconnected corrugated carbon-based network, which shows a significant decrease in oxygen containing functional groups and an overall increase in the C—C sp$^2$ carbon peak. This points to an efficient deoxygenating process as well as the re-establishment of C=C bonds in the interconnected corrugated carbon-based network. These results are consistent with the Raman analysis. Thus, an infrared laser such as LWL 34 (FIG. 2) is powerful enough to remove a majority of the oxygen functional groups, as is evident in the XPS spectrum of the interconnected corrugated carbon-based network, which only shows a small disorder peak and a peak at 287.6 eV. The latter corresponds to the presence of sp$^3$ type carbons suggesting that a small amount of carboxyl groups remain in the final product. In addition, the presence of a $\pi$ to $\pi^*$ satellite peak at ~290.7 eV indicates that delocalized $\pi$ conjugation is significantly stronger in the interconnected corrugated carbon-based network as this peak is miniscule in the GO XPS spectrum. The appearance of the delocalized $\pi$ peak is a clear indication that conjugation in the GO film is restored during the laser reduction process and adds support that an sp$^2$ carbon network has been re-established. The decreased intensity of the oxygen containing functional groups, the dominating C=C bond peak and the presence of the delocalized $\pi$ conjugation all indicate that a low energy infrared laser is an effective tool in the generation of the interconnected corrugated carbon-based network.

Figure 11E:
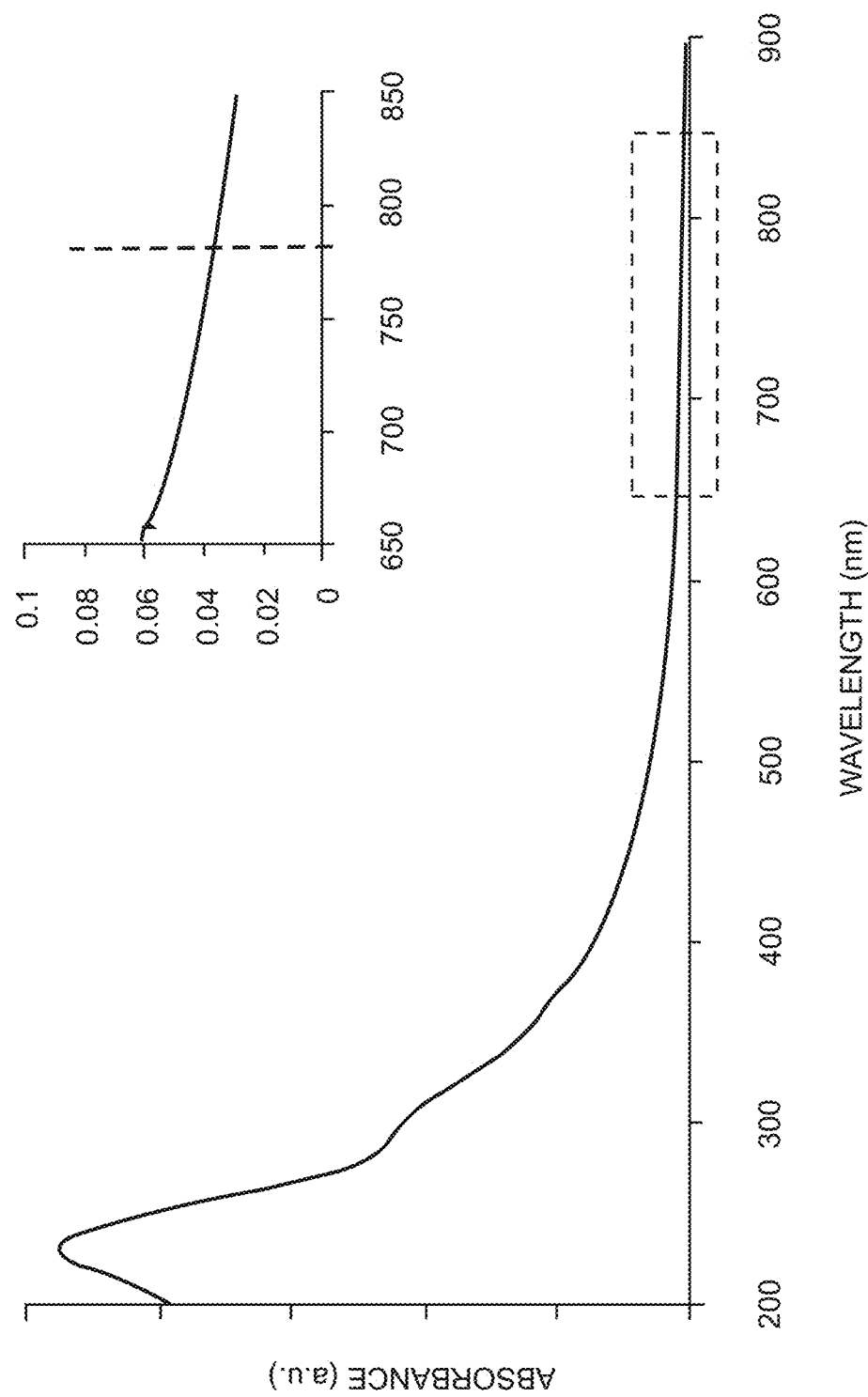

FIG. 11E depicts UV-visible light absorbance spectra of GO shown in black. The inset shows a magnified view of the boxed area showing the absorbance of GO with respect to a 780 nm infrared laser in the 650 to 850 nm region.

The future development of multifunctional flexible electronics such as roll-up displays, photovoltaic cells, and even wearable devices presents new challenges for designing and fabricating lightweight, flexible energy storage devices.

Figure 12A:
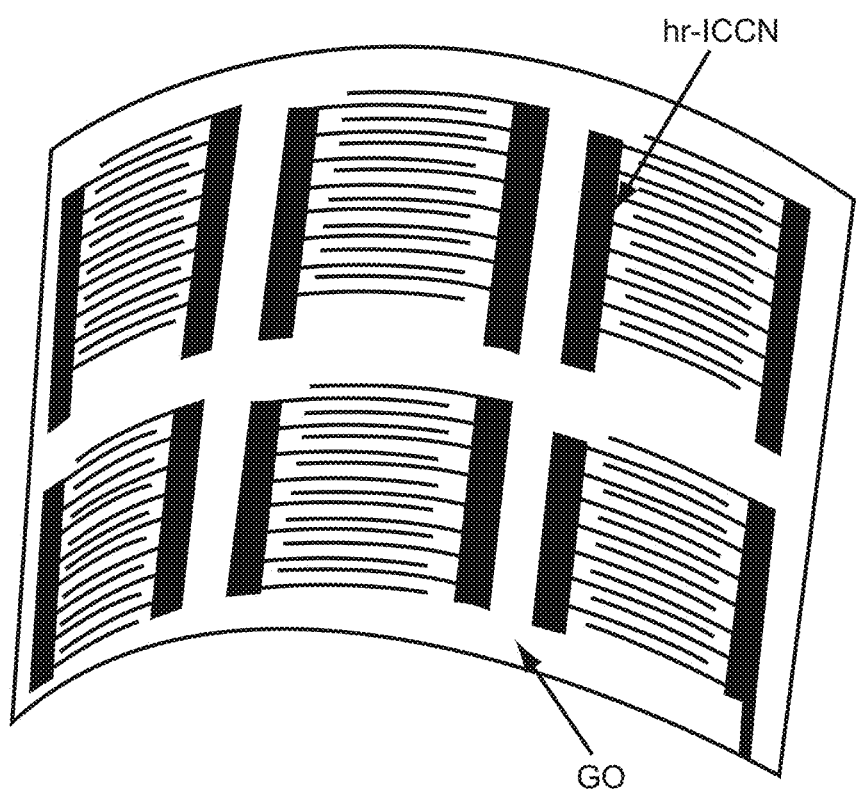
FIG. 12A is a structural diagram showing a set of interdigitated electrodes made of interconnected corrugated carbon-based networks with dimensions of 6 mm×6 mm, spaced at ~500 µm, that are directly patterned onto a thin film of GO.
Figure 12B:
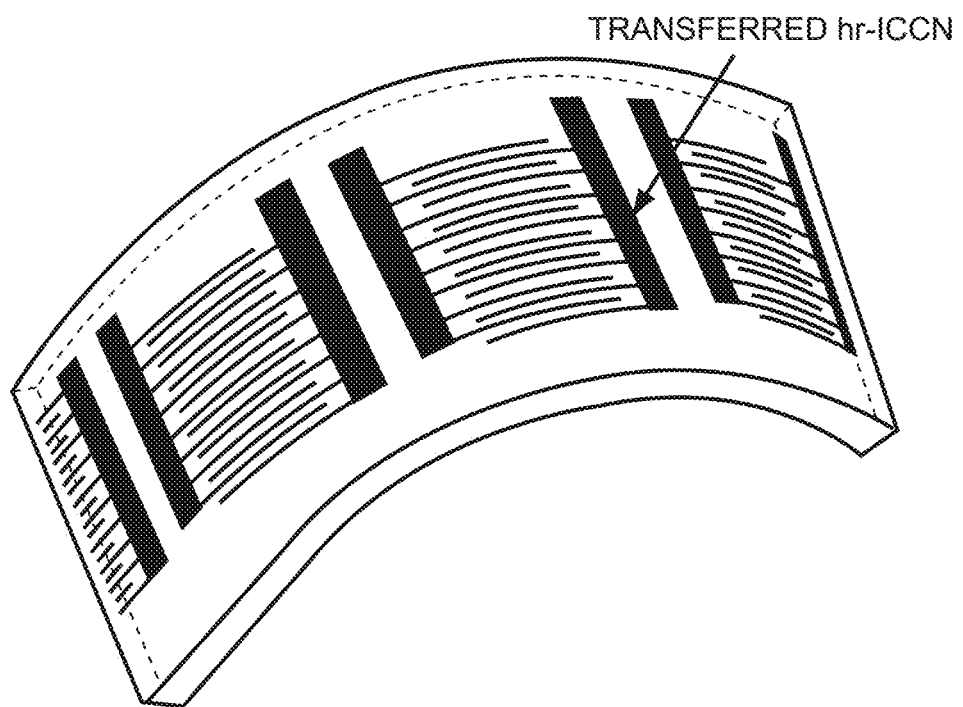
FIG. 12B is a structural diagram showing the set of interdigitated electrodes transferred onto another type of substrate.

Embodiments of the present disclosure also include other types of electrical and electronic devices. For example, FIG. 12A shows a set of interdigitated electrodes with dimensions of 6 mm×6 mm, spaced at ~500 µm, that are directly patterned onto a thin film of GO. Prior to being patterned, the GO film was deposited on a thin flexible substrate, polyethylene terephthalate (PET), in order to fabricate a set of electrodes that are mechanically flexible. The top arrow points to the region of the interconnected corrugated carbon-based network that makes up the black interdigitated electrodes, while the bottom arrow points to the un-reduced golden colored GO film. Since the electrodes are directly patterned onto the GO film on a flexible substrate, the need for post-processing such as transferring the film to a new substrate is unnecessary. Although, if desired, a peel and stick method could be used to selectively lift-off the black interdigitated electrodes made of interconnected corrugated carbon-based networks with e.g. polydimethylsiloxane (PDMS) and transfer it onto other types of substrates (FIG. 12B). The simplicity of this method allows substantial control over pattern dimensions, substrate selectivity and electrical properties of the interconnected corrugated carbon-based network by controlling the laser intensity and thereby the amount of reduction in each film.

Figure 13:
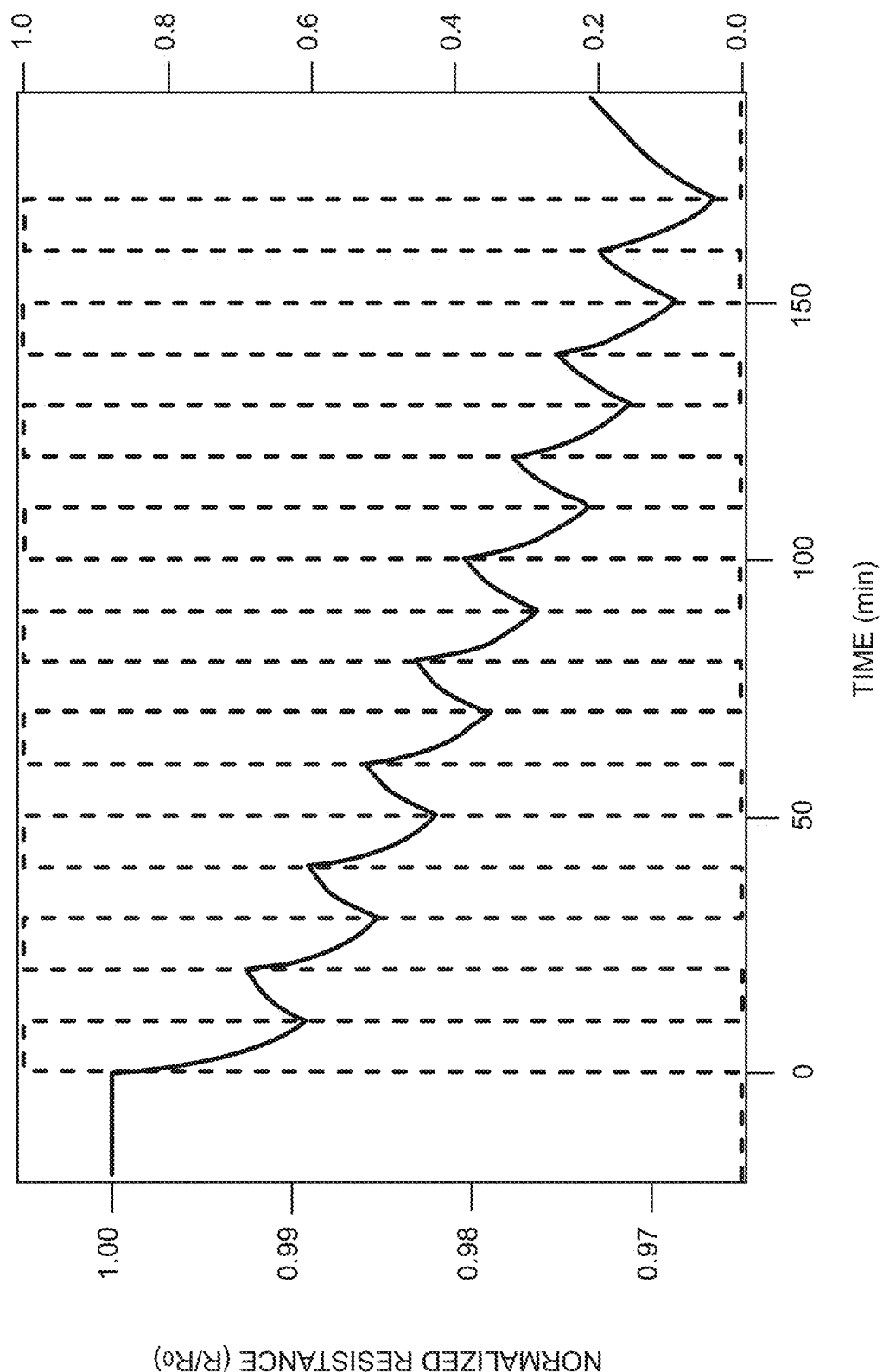
FIG. 13 shows the sensor response for a patterned flexible set of interdigitated electrodes that are made of interconnected corrugated carbon-based networks that are exposed to 20 ppm of nitrous oxide ($NO_2$) in dry air.

These interdigitated electrodes can, in turn, be used as an all-organic flexible gas sensor for the detection of NO$_2$. FIG. 13 shows the sensor response for a patterned flexible set of interdigitated electrodes made of interconnected corrugated carbon-based networks that are exposed to 20 ppm of NO$_2$ in dry air. This sensor was fabricated by patterning interconnected corrugated carbon-based networks to fabricate the active electrode and marginally reducing the area in between the electrodes to have a consistent sheet resistance of ~7775 ohms/sq. In this way, it is possible to bypass the use of metal electrodes and directly pattern both the electrode and the sensing material on the flexible substrate simultaneously. The plot relates NO$_2$ gas exposure to R/R$_0$, where R$_0$ is the sheet resistance at the initial state and R is the resistance of the interconnected corrugated carbon-based networks film after exposure to the gas. The film was exposed to NO$_2$ gas for 10 min followed immediately by purging with air for another 10 min. This process was then repeated nine more times for a total of 200 min. Even with a slightly lower sensitivity than more sophisticated and optimized sensors, the un-optimized sensor made up of interconnected corrugated carbon-based networks still shows good, reversible sensing for NO$_2$ and its easy fabrication makes it quite advantageous for these systems. The sensor made up of interconnected corrugated carbon-based networks for NO$_2$ holds promise for improving the fabrication of all-organic flexible sensor devices, at low cost by using inexpensive starting materials directly patterned with an inexpensive laser.

Figure 14A:
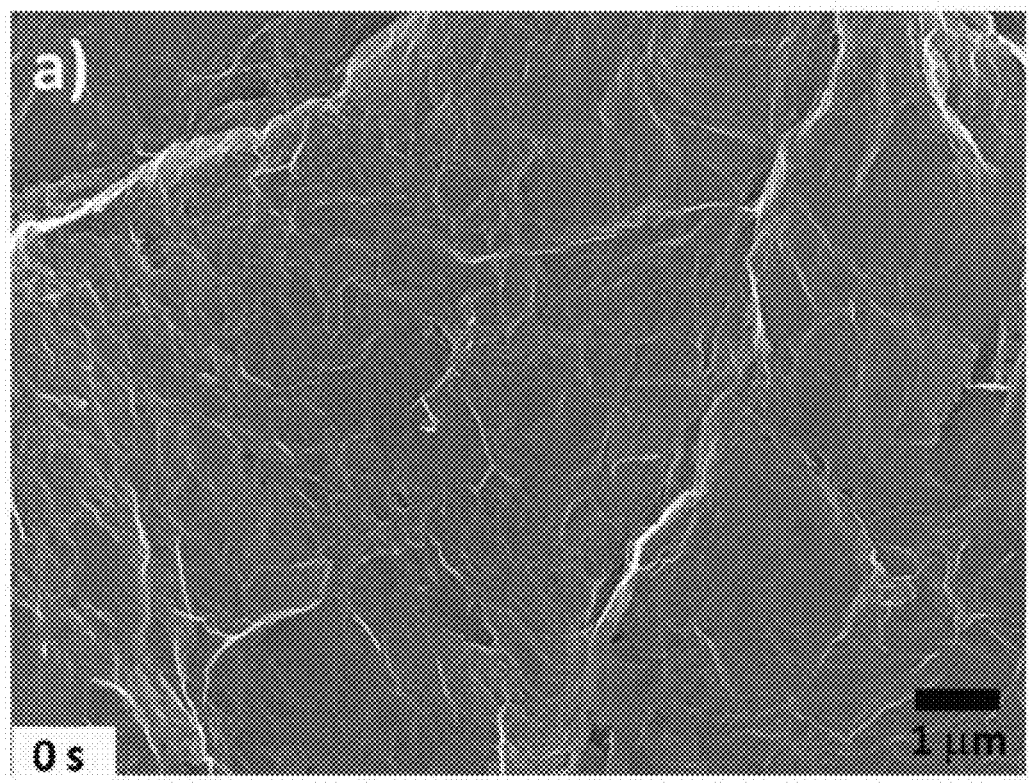
FIGS. 14A-14D shows SEM images illustrating the growth of platinum (Pt) nanoparticles onto a scaffold made of an interconnected corrugated carbon-based network with respect to electrodeposition times corresponding to 0, 15, 60 and 120 seconds.
Figure 14B:
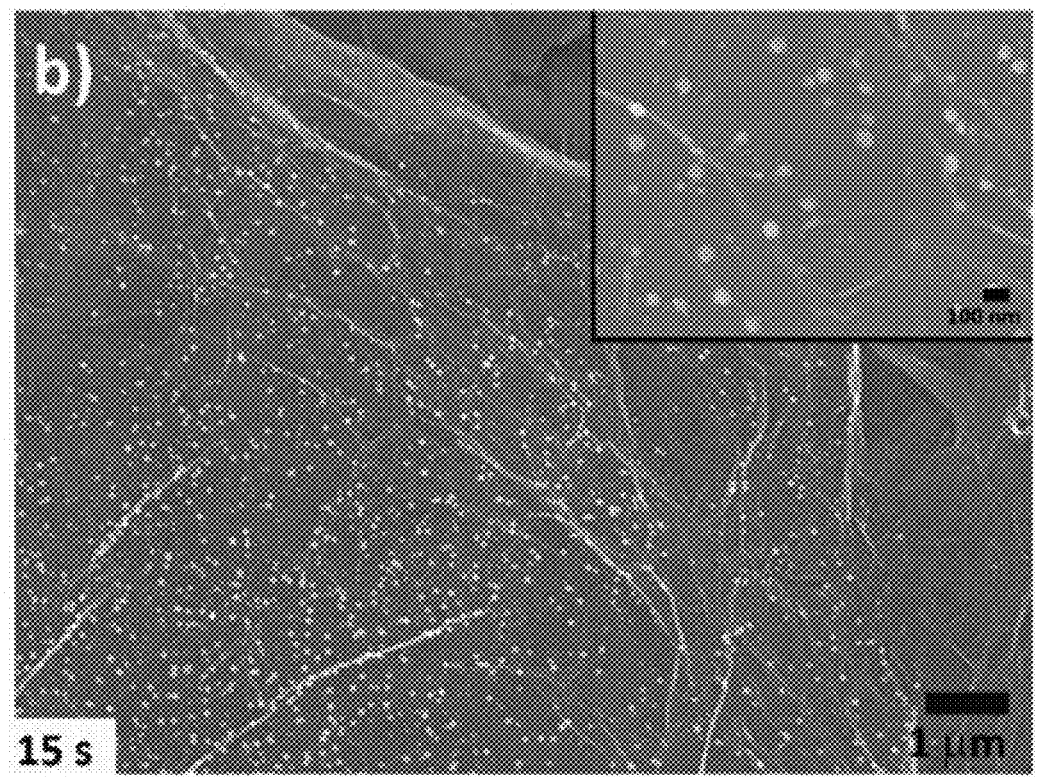
Figure 14C:
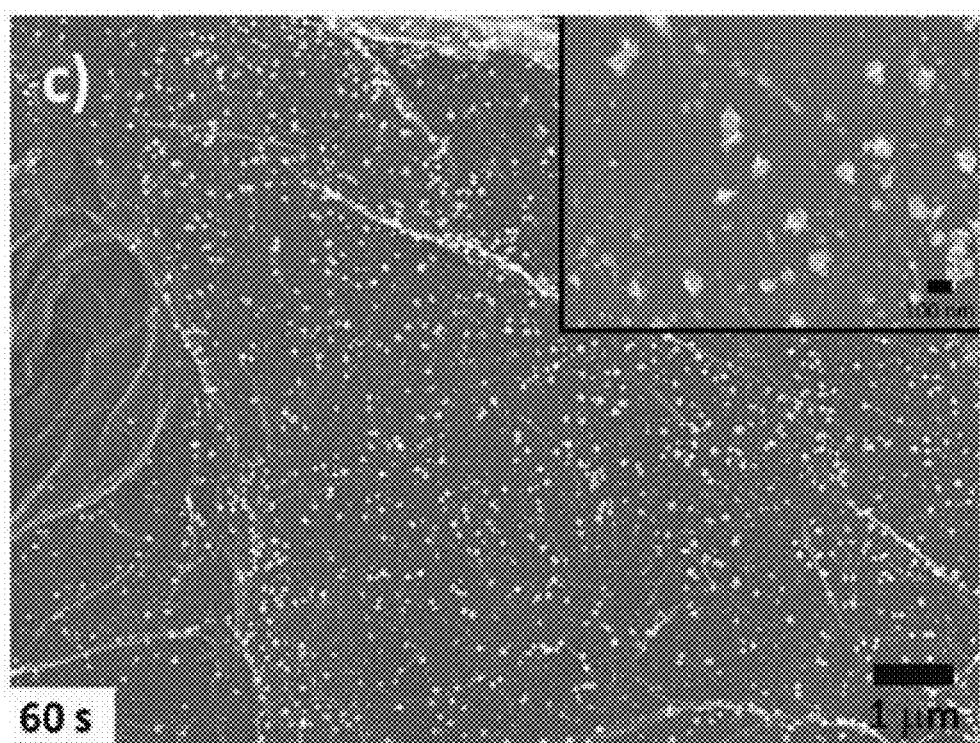
Figure 14D:
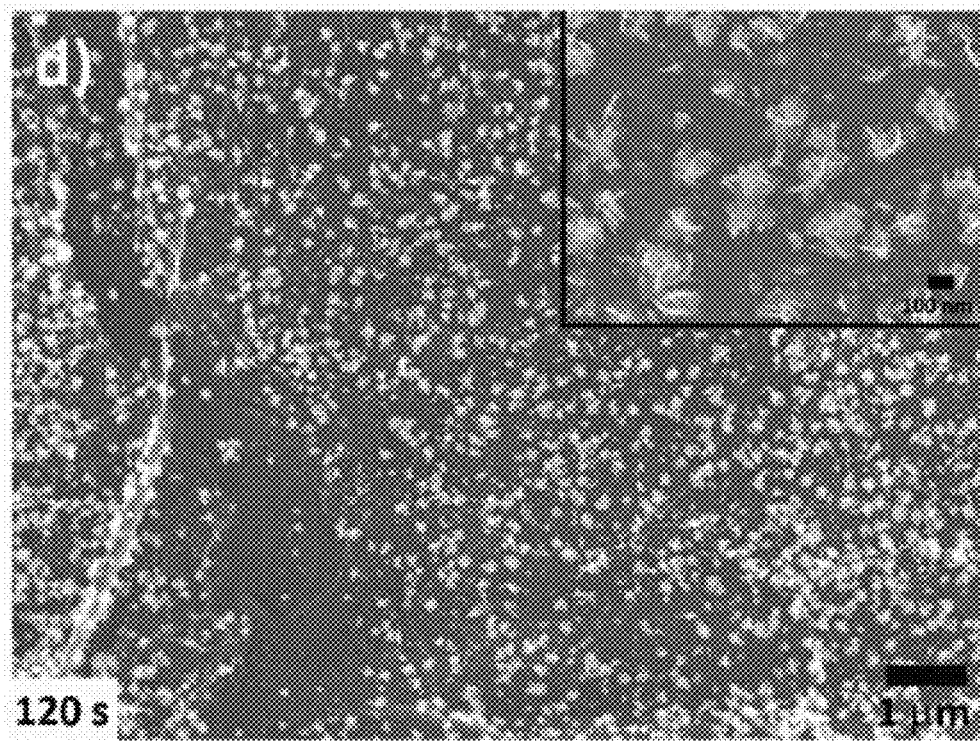

The high conductivity and increased surface area resulting from the plurality of expanded and interconnected carbon layers, makes interconnected corrugated carbon-based networks a viable candidate for use as a heterogeneous catalyst support for metal nanoparticles. In particular, the direct growth of Pt nanoparticles on interconnected corrugated carbon-based networks could aid in the improvement of methanol based fuel cells, which have shown enhanced device performance from large surface area and conducting carbon-based scaffolds. This disclosure demonstrates that an interconnected corrugated carbon-based network is a viable scaffold for the controllable growth of Pt nanoparticles. By electrochemically reducing 1 mM of $K_2PtCl_4$ with 0.5 M $H_2SO_4$ at −0.25 V for different periods of time, it is possible to actively control the Pt particle size that is electrodeposited on the interconnected corrugated carbon-based network film. FIGS. 14A-14D shows scanning electron microscopy images illustrating the growth of Pt nanoparticles with respect to electrodeposition times corresponding to 0, 15, 60 and 120 seconds. As expected, there are no Pt particles present at 0 seconds of electrodeposition (FIG. 14A), but small Pt nanoparticles are clearly visible after just 15 seconds (FIG. 14B) with nanoparticle sizes ranging from 10-50 nm (FIG. 14B, inset). After 60 seconds of electrodeposition, larger Pt nanoparticles grow with particle sizes averaging 100 to 150 nm (FIG. 14C). Finally, after 120 seconds, 200 to 300 nm particles are found evenly distributed across the surface of the interconnected corrugated carbon-based networks (FIG. 14D). The active growth of Pt nanoparticles at controllable diameters on interconnected corrugated carbon-based networks could make a potentially useful hybrid material for applications that require metal nanoparticles, such as methanol fuel cells and gas phase catalysts. Moreover, if palladium (Pd) is deposited a sensor made of an interconnected corrugated carbon-based network could be used for sensors that detect hydrogen or for catalysis such as Suzuki coupling or Heck coupling.

Carbon electrodes have attracted tremendous interest for various electrochemical applications because of their wide potential window and good electrocatalytic activity for many redox reactions. Given its high surface area and flexibility and the fact that it is an all-carbon electrode, interconnected corrugated carbon-based networks could revolutionize electrochemical systems by making miniaturized and fully flexible devices. Here, understanding the electrochemical properties of interconnected corrugated carbon-based networks is highly beneficial to determining its potential for electrochemical applications. Recently, graphene's electrocatalytic properties have been demonstrated to stem, in large part, from the efficient electron transfer at its edges rather than its basal planes. In fact, it has been reported that graphene exhibits in certain systems electrocatalytic activity similar to that of edge plane highly ordered pyrolytic graphite. In addition to having a highly expanded network, an interconnected corrugated carbon-based network also displays a large amount of edge planes (Refer back to FIG. 5), making it an ideal system for studying the role of edge planes on the electrochemistry of graphene-based nanomaterials.

Figure 15:
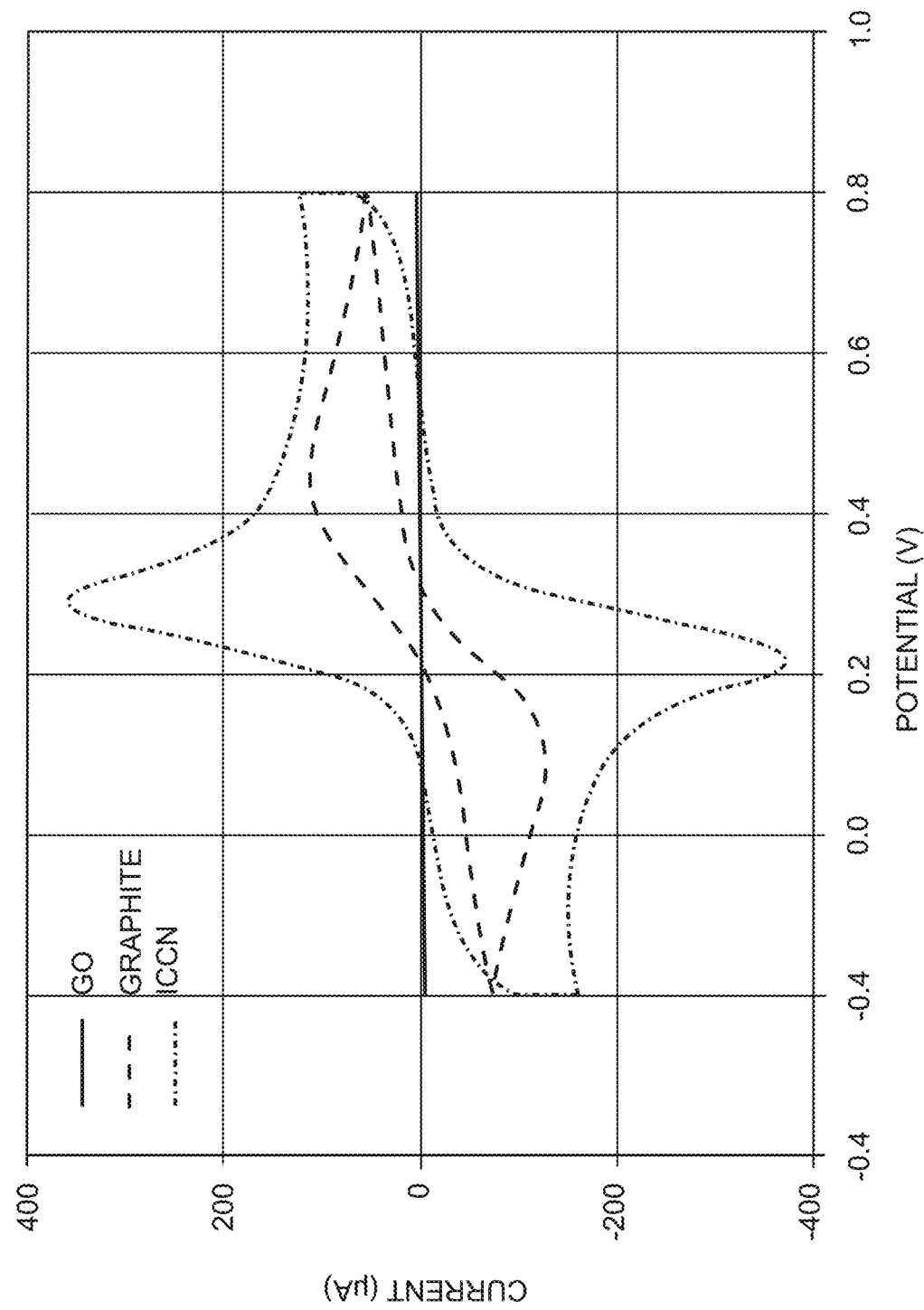
FIG. 15 compares the CV profiles of GO, graphite and electrodes made of interconnected corrugated carbon-based networks in an equimolar mixture of 5 mM $K_3[Fe(CN)_6]$/$K_4[Fe(CN)_6]$ dissolved in 1.0 M KCl solution at a scan rate of 50 mV/s.

In this regard, the electrochemical behavior associated with the electron transfer of flexible electrodes made of interconnected corrugated carbon-based networks using a $[Fe(CN)_6]^{3-/4-}$ couple as a redox probe is characterized. For example, FIG. 15 compares the CV profiles of GO, graphite and electrodes made of interconnected corrugated carbon-based networks in an equimolar mixture of 5 mM $K_3[Fe(CN)_6]/K_4[Fe(CN)_6]$ dissolved in 1.0 M KCl solution at a scan rate of 50 mV/s. Unlike GO and graphite, the electrode made of interconnected corrugated carbon-based networks approaches the behavior of a perfectly reversible system with a low $\Delta E_p$ (peak-to-peak potential separation) of 59.5 mV at a scan rate of 10 mV/s to 97.6 mV at a scan rate 400 mV/s. The low $\Delta E_p$ values approaches the calculated theoretical value of 59 mV. Given that $\Delta E_p$ is directly related to the electron transfer rate constant ($k^0_{obs}$), the low experimental value of $\Delta E_p$ indicates a very fast electron transfer rate. The calculated $k^0_{obs}$ values vary from $1.266 \times 10^4$ cm s$^{-1}$ for graphite and, as expected, increases for an interconnected corrugated carbon-based network to $1.333 \times 10^{-2}$ cm s$^{-1}$.

The redox system that was used for the evaluation of the electron transfer kinetics was 5 mM $K_3[Fe(CN)_6]/K_4[Fe(CN)_6]$ (1:1 molar ratio) dissolved in 1.0 M KCl solution. To ensure a stable electrochemical response, the electrodes were first cycled for at least 5 scans before collecting the experimental data. The heterogeneous electron transfer rate constant ($k^0_{obs}$) was determined using a method developed by Nicholson, which relates the peak separation ($\Delta E_p$) to a dimensionless kinetic parameter $\psi$, and consequently to $k^0_{obs}$ according to the following equation:

$$k^0_{obs} = \psi \left[ \sqrt{D_O \pi v \left(\frac{nF}{RT}\right)} \right] \left(\frac{D_R}{D_O}\right)^{\frac{\alpha}{2}}$$

where $D_O$ and $D_R$ are the diffusion coefficients of the oxidized and reduced species, respectively. The other variables include v—the applied scan rate, n—the number of electrons transferred in the reaction, F—the Faraday constant, R—the gas constant, T—the absolute temperature and α—the transfer coefficient. The diffusion coefficients of the oxidized and reduced species are typically similar; therefore, the term $(D_R/D_O)^{\alpha/2}$ is ~1. A diffusion coefficient ($D_O$) of $7.26 \times 10^{-6}$ cm$^2$ s$^{-1}$ was used for $[[Fe(CN)_6]^{3-/4-}$ in 1.0 M KCl.

In addition to the relatively large increase in the electron transfer rate at the electrode made of interconnected corrugated carbon-based networks (~two orders of magnitude times faster than a graphite electrode), there is also substantial electrochemical activity for the electrode made of interconnected corrugated carbon-based networks as seen by an increase of ~268% in the voltammetric peak current. These drastic improvements are attributed to the expanded architecture of interconnected corrugated carbon-based network films, which provide large open areas for the effective diffusion of the electroactive species and allow a better interfacial interaction with the interconnected corrugated carbon-based network surface. Additionally, it is surmised that the amount of edge-like surface per unit mass is thus, much higher than graphite, and therefore contributes to the higher electron transfer rates, as seen here. Given the large number of exposed edge sites in interconnected corrugated carbon-based networks, it is not surprising to find that it not only has a higher $k^0_{obs}$ value than graphite, but surpasses that of carbon nanotube based electrodes and that of stacked graphene nanofibers.

Note that the electrodes made of interconnected corrugated carbon-based networks are fabricated on flexible PET substrates covered with GO which, when laser reduced, serves as both the electrode and the current collector, thus making this particular electrode not only lightweight and flexible, but also inexpensive. In addition, the low oxygen content in interconnected corrugated carbon-based networks (~3.5%) as shown through XPS analysis is quite advantageous to the electrochemical activity seen here, since a higher oxygen content at the edge plane sites have been shown to limit and slow down the electron transfer of the ferri-/ferrocyanide redox couple. As such, embodiments of the present disclosure provides methodologies for making highly electroactive electrodes for potential applications in vapor sensing, biosensing, electrocatalysis and energy storage.

The present disclosure relates to a facile, solid-state and environmentally safe method for generating, patterning, and electronic tuning of graphite-based materials at a low cost. Interconnected corrugated carbon-based networks are shown to be successfully produced and selectively patterned from the direct laser irradiation of GO films under ambient conditions. Circuits and complex designs are directly patterned on various flexible substrates without masks, templates, post-processing, transferring techniques, or metal catalysts. In addition, by varying the laser intensity and laser irradiation treatments the electrical properties of interconnected corrugated carbon-based networks are precisely tuned over five orders of magnitude, a feature that has proven difficult with other methods. This new mode of generating interconnected corrugated carbon-based networks provides a new venue for manufacturing all organic based devices such as gas sensors, and other electronics. The relatively inexpensive method for generating interconnected corrugated carbon-based networks on thin flexible organic substrates makes it a relatively ideal heterogeneous scaffold for the selective growth of metal nanoparticles. Moreover, the selective growth of metal nanoparticles has the potential in electrocatalyzing methanol fuel cells. Further still, films made of interconnected corrugated carbon-based networks show exceptional electrochemical activity that surpasses other carbon-based electrodes in the electron charge transfer of ferri-/ferrocyanide redox couple. The simultaneous reduction and patterning of GO through the use of an inexpensive laser is a new technique, which offers significant versatility for the fabrication of electronic devices, all organic devices, asymmetric films, microfluidic devices, integrated dielectric layers, batteries, gas sensor, and electronic circuitry.

In contrast to other lithography techniques, this process uses a low-cost infrared laser in an unmodified, commercially available CD/DVD optical disc drive with LightScribe technology to pattern complex images on GO and has the additional benefit to simultaneously produce the laser converted corrugated carbon network. A LightScribe technology laser is typically operated with a 780 nm wavelength at a power output within a range of around 5 mW to around 350 mW. However, it is to be under stood that as long as the carbon-based oxide absorbs within the spectrum of the laser's emission, the process is achievable at any wavelength at a given power output. This method is a simple, single step, low cost, and maskless solid-state approach to generating interconnected corrugated carbon-based networks that can be carried out without the necessity of any post-processing treatment on a variety of thin films. Unlike other reduction methods for generating graphite-based materials, this method is a non-chemical route and a relatively simple and environmentally safe process, which is not limited by chemical reducing agents.

The technique described herein is inexpensive, does not require bulky equipment, displays direct control over film conductivity and image patterning, can be used as a single step for fabricating flexible electronic devices, all without the necessity for sophisticated alignment or producing expensive masks. Also, due to the conductive nature of the materials used, it is possible to control the resulting conductivity by simply patterning at different laser intensities and power, a property that has yet to been shown by other methods. Working circuit boards, electrodes, capacitors, and/or conducting wires are precisely patterned via a computerized program. The technique allows control over a variety of parameters, and therefore provides a venue for simplifying device fabrication and has the potential to be scaled, unlike other techniques that are limited by cost or equipment. This method is applicable to any photothermically active material, which includes but is not limited to GO, conducting polymers, and other photothermically active compounds such as carbon nanotubes.

As described above, a method has been presented for producing graphite-based materials that is not only facile, inexpensive and versatile, but is a one step environmentally safe process for reducing and patterning graphite films in the solid state. A simple low energy, inexpensive infrared laser is used as a powerful tool for the effective reduction, subsequent expansion and exfoliation and fine patterning of GO. Aside from the ability to directly pattern and effectively produce large areas of highly reduced laser converted graphite films, this method is applicable to a variety of other thin substrates and has the potential to simplify the manufacturing process of devices made entirely from organic materials. A flexible all organic gas sensor has been fabricated directly by laser patterning of GO deposited on thin flexible PET. An interconnected corrugated carbon-based network is also shown to be an effective scaffold for the successful growth and size control of Pt nanoparticles via a simple electrochemical process. Finally, a flexible electrode made of interconnected corrugated carbon-based networks was fabricated, which displays a textbook-like reversibility with an impressive increase of ~238% in electrochemical activity when compared to graphite towards the electron transfer between the ferri-/ferrocyanide redox couple. This proof-of concept process has the potential to effectively improve applications that would benefit from the high electrochemical activity demonstrated here including batteries, sensors and electrocatalysis.

Those skilled in the art will recognize improvements and modifications to the embodiments of the present disclosure. All such improvements and modifications are considered within the scope of the concepts disclosed herein and the claims that follow.

What is claimed is:

1. A method of producing a patterned interconnected corrugated carbon-based network, comprising:
   a) receiving a substrate having a carbon-based oxide film;
   b) generating a light beam having a power of about 5 mW to about 350 mW and a frequency of about 660 nm to about 780 nm with a laser to reduce and expand portions of the carbon-based oxide film to form a plurality of expanded and interconnected carbon layers that are electrically conductive, wherein electrical conductivity of the plurality of expanded and interconnected carbon layers is tuned according to the power of the light beam; and
   c) directing the light beam across the carbon-based oxide film in a predetermined pattern of the plurality of expanded and interconnected carbon layers via a computerized control system.

2. The method of claim 1, wherein the plurality of expanded and interconnected carbon layers has a sheet resistance that is tunable within a range of 20 megaohms per square to 80 ohms per square.

3. The method of claim 1, wherein the carbon-based oxide film is a graphite oxide film.

4. The method of claim 3, wherein the light beam forms the predetermined pattern of the plurality of expanded and interconnected carbon layers within the carbon-based oxide film that is repeated over predetermined portions of the predetermined pattern to increase a graphite oxide to a carbon-based oxide ratio.

5. The method of claim 1, wherein the plurality of expanded and interconnected carbon layers has a carbon-to-oxygen (C/O) ratio that ranges from 100:1 to 25:1.

6. The method of claim 1, wherein the light beam is a laser beam.

7. The method of claim 1, wherein a light beam emission ranges from near infrared to ultraviolet wavelengths.

8. The method of claim 1, further including loading the substrate into an automated laser patterning system before generating the light beam having the power density sufficient to reduce portions of the carbon-based oxide film to the patterned interconnected corrugated carbon-based network.

9. The method of claim 1, further including an initial step of drop-casting a carbon-based oxide solution onto the substrate.

10. The method of claim 1, wherein the substrate is polyethylene terephthalate (PET).

11. The method of claim 1, further including exposing the substrate with oxygen plasma for about three minutes.

12. The method of claim 1, wherein each of the expanded and interconnected carbon layers is a single corrugated carbon sheet.

13. The method of claim 1, wherein the plurality of expanded and interconnected carbon layers yields an electrical conductivity that is greater than about 1500 S/m.

14. The method of claim 1, wherein a range of thickness of the plurality of expanded and interconnected carbon layers is from about 7 μm to about 8 μm.

15. The method of claim 1, wherein a number of expanded and interconnected carbon layers in the plurality of expanded and interconnected carbon layers is greater than about 100.

16. The method of claim 1, wherein the predetermined pattern defines a scaffold for direct growth of nanoparticles.

17. The method of claim 16, wherein the nanoparticles are platinum (Pt) nanoparticles.

18. A method of producing a patterned interconnected corrugated carbon-based network, comprising:
 a) receiving a substrate having a carbon-based oxide film;
 b) generating a light beam having a power of about 5 mW to about 350 mW and a diameter of about 0.7 μm to about 1 μm with a laser to reduce and expand portions of the carbon-based oxide film to form a plurality of expanded and interconnected carbon layers that are electrically conductive, wherein electrical conductivity of the plurality of expanded and interconnected carbon layers is tuned according to the power of the light beam; and
 c) directing the light beam across the carbon-based oxide film in a predetermined pattern of the plurality of expanded and interconnected carbon layers via a computerized control system.

* * * * *